United States Patent
Tsunoda et al.

(10) Patent No.: US 9,458,447 B2
(45) Date of Patent: Oct. 4, 2016

(54) MPHOSPH1 PEPTIDES AND VACCINES INCLUDING THE SAME

(75) Inventors: Takuya Tsunoda, Kanagawa (JP); Ryuji Osawa, Kanagawa (JP); Sachiko Yoshimura, Kanagawa (JP); Tomohisa Watanabe, Kanagawa (JP); Yusuke Nakamura, Tokyo (JP)

(73) Assignee: OncoTherapy Science, Inc., Kanagawa (JP)

( * ) Notice: Subject to any disclaimer, the term of this patent is extended or adjusted under 35 U.S.C. 154(b) by 217 days.

(21) Appl. No.: 14/131,019

(22) PCT Filed: Aug. 9, 2012

(86) PCT No.: PCT/JP2012/005076
§ 371 (c)(1),
(2), (4) Date: Feb. 12, 2014

(87) PCT Pub. No.: WO2013/024582
PCT Pub. Date: Feb. 21, 2013

(65) Prior Publication Data
US 2014/0154281 A1 Jun. 5, 2014

Related U.S. Application Data

(60) Provisional application No. 61/522,991, filed on Aug. 12, 2011.

(51) Int. Cl.
| | |
|---|---|
| *C07K 7/00* | (2006.01) |
| *A61K 38/10* | (2006.01) |
| *C12N 9/00* | (2006.01) |
| *A61K 39/00* | (2006.01) |
| *C07K 14/47* | (2006.01) |
| *C12N 9/14* | (2006.01) |
| *G01N 33/50* | (2006.01) |
| *C12N 5/0784* | (2010.01) |
| *C12N 5/10* | (2006.01) |
| *G01N 33/574* | (2006.01) |
| *A61K 38/00* | (2006.01) |

(52) U.S. Cl.
CPC ............... *C12N 9/93* (2013.01); *A61K 39/00* (2013.01); *A61K 39/0011* (2013.01); *C07K 14/4738* (2013.01); *C12N 5/0639* (2013.01); *C12N 5/10* (2013.01); *C12N 9/14* (2013.01); *C12Y 306/04004* (2013.01); *G01N 33/505* (2013.01); *G01N 33/57407* (2013.01); *A61K 38/00* (2013.01); *C12N 2502/1114* (2013.01); *G01N 2440/14* (2013.01)

(58) Field of Classification Search
CPC ................................................ A61K 39/0011
See application file for complete search history.

(56) References Cited

U.S. PATENT DOCUMENTS

| | | | |
|---|---|---|---|
| 6,294,663 | B1 | 9/2001 | O'Brien et al. |
| 7,998,695 | B2 | 8/2011 | Nakamura et al. |
| 8,552,146 | B2 | 10/2013 | Fujioka et al. |
| 8,557,955 | B2 | 10/2013 | Fujioka et al. |
| 2006/0024692 | A1 | 2/2006 | Nakamura et al. |
| 2007/0099251 | A1 | 5/2007 | Zhang et al. |
| 2008/0207497 | A1 | 8/2008 | Ramakrishna et al. |
| 2012/0014996 | A1 | 1/2012 | Nakamura et al. |
| 2012/0282286 | A1 | 11/2012 | Fujioka et al. |
| 2013/0011933 | A1 | 1/2013 | Nakamura et al. |
| 2013/0129759 | A1 | 5/2013 | Fujioka et al. |

FOREIGN PATENT DOCUMENTS

| | | |
|---|---|---|
| RU | 94038427 A | 10/1996 |
| WO | 93/03764 A1 | 3/1993 |
| WO | 02/46416 A2 | 6/2002 |
| WO | 03/040165 A2 | 5/2003 |
| WO | 03/064609 A2 | 8/2003 |
| WO | 2004/031413 A2 | 4/2004 |
| WO | 2006/085684 A2 | 8/2006 |

(Continued)

OTHER PUBLICATIONS

Janeway et al., Immunobiology—The Immune System in Health and Disease, 3rd ed, pp. 130-131, Tokyo: Nankodo Co., Ltd. (1998), with translation by T. Saszuki.

Zaremba, et al., "Identification of an Enhancer Agonist Cytotoxic T Lymphocytes Peptide from Human Carcinoembryonic Antigen", *Cancer Res.*, vol. 57, No. 20, pp. 4570-4577 (1997).

Yamaue, "Antigenic peptide therapy for tumors 3 (Ayumi) cancer immunotherapy using CEA antigenic peptides", Igaku No Ayumi., vol. 190, No. 2, p. 135-138 (1999), with English Translation, 10 pages.

(Continued)

Primary Examiner — Prema Mertz
(74) Attorney, Agent, or Firm — Kilpatrick Townsend & Stockton LLP

(57) ABSTRACT

As discussed in greater detail herein, isolated epitope peptides derived from MPHOSPH1 bind to an HLA antigen and induce cytotoxic T lymphocytes (CTL) and thus are suitable for use in the context of cancer immunotherapy, more particularly cancer vaccines. The inventive peptides encompass both the above-mentioned MPHOSPH1-derived amino acid sequences and modified versions thereof, in which one, two, or several amino acids are substituted, deleted, inserted or added, provided such modified versions retain the requisite CTL inducibility of the original sequences. Further provided are polynucleotides encoding any of the aforementioned peptides as well as pharmaceutical agents or compositions that include any of the aforementioned peptides or polynucleotides. The peptides, polynucleotides, and pharmaceutical agents or compositions of this invention find particular utility in either or both of the treatment and prevention of cancers and tumors, including, for example, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

10 Claims, 5 Drawing Sheets

(56) References Cited

FOREIGN PATENT DOCUMENTS

| WO | 2008/023842 A1 | 2/2008 |
|---|---|---|
| WO | 2008/047473 A1 | 4/2008 |

OTHER PUBLICATIONS

Nishiu, et al, "Microarray Analysis of Gene-expression Profiles in Diffuse Large B-cell Lymphoma: Identification of Genes Related to Disease Progression", *Jpn J Cancer Res*, vol. 93, No. 8, pp. 894-901 (2002).
Obara, et al, "Cancer Peptide Vaccine Therapy Developed from Oncoantigens Identified through Genome-wide Expression Profile Analysis for Bladder Cancer", *Jpn J Clin Oncol*, vol. 42, No. 7, pp. 591-600 (2012).
Boon, "Tumor Antigens Recognized by Cytolytic T Lymphocytes: Present Perspectives for Specific Immunotherapy," *Int J. Cancer*, vol. 54, No. 2, pp. 177-180 (1993).
Boon, et al., "Human Tumor Antigens Recognized by T Lymphocytes", *J. Exp. Med.*, vol. 183, No. 3, pp. 725-729 (1996).
Harris, "Structure and Function of the p53 Tumor Suppressor Gene: Clues for Rational Cancer Therapeutic Strategies", *J. Natl. Cancer Inst.*, vol. 88, No. 20, pp. 1442-1455 (1996).
Butterfield, et al, "Generation of Human T-cell responses to an HLA-2.1 restricted Peptide Epitope Derived from α-Fetoprotein", *Cancer Res.*, vol. 59, No. 13, pp. 3134-3142 (1999).
Vissers, et al., "The Renal Cell Carcinoma-associated Antigen G250 Encodes a Human Leukocyte Antigen (HLA)-A2.1-restricted Epitope Recognized by Cytotoxic T Lymphocytes", *Cancer Res.*, vol. 59, No. 21, pp. 5554-5559 (1999).
Van Der Burg, et al., "Immunogenicity of Peptides Bound to MHC Class I Molecules Depends on the MHC-Peptide Complex Stability," *J. Immunol.*, vol. 156, No. 9, pp. 3308-3314 (1996).
Tanaka, et al., "Induction of Antitumor Cytotoxic T Lymphocytes with a MAGE-3-encoded Synthetic Peptide Presented by Human Leukocytes Antigen-A24", *Cancer Res.*, vol. 57, No. 20, pp. 4465-4468 (1997).
Fujie, et al., "A Mage-1-Encoded HLA-A24-Binding Synthetic Peptide Induces Specific Anti-tumor Cytotoxic T Lymphocytes", *Int. J. Cancer.*, vol. 80, No. 2, pp. 169-172 (1999).
Kikuchi, et al., "Identification of a Sart-1-Derived Peptide Capable of Inducing HLA-A24-Restricted and Tumor-Specific Cytotoxic T Lymphocytes", *Int. J Cancer*, vol. 81, No. 3, pp. 459-466 (1999).
Oiso, et al., "A Newly Identified *Mage-3*-Derived Epitope Recognized by HLA-A24-Restricted Cytotoxic T Lymphocytes", *Int J Cancer*, vol. 81, No. 3, pp. 387-394 (1999).
Belli, et al., "Vaccination of Metastatic Melanoma Patients with Autologous Tumor-Derived Heat Shock Protein gp96-Peptide complexes: Clinical and Immunologic Findings", *J Clin Oncol.*, vol. 20, No. 20, pp. 4169-4180 (2002).
Coulie, et al., "Cytolytic T-cell Responses of cancer patients vaccinated with a MAGE antigen", *Immunol Rev.*, vol. 188, pp. 33-42 (2002).
Rosenberg, et al., "Cancer immunotherapy: moving beyond current vaccines", *Nat. Med.* vol. 10, No. 9, pp. 909-915 (2004).
Abaza, et al, "M Phase Phosphoprotein 1 Is a Human Plus-end-directed Kinesin-related Protein Required for Cytokinesis", *J Biol Chem.*, vol. 278, No. 30, pp. 27844-278852 (2003).
Kamimoto, et al., "Identification of a Novel Kinesin-related Protein, KRMP1, as a Target for Mitotic Peptidyl-prolyl Isomerase Pin1", *J Biol Chem.*, vol. 276, No. 40, pp. 37520-37528 (2001).
Kanehira, et al., "Oncogenic Role of MPHOSPH1, a Cancer-Testis Antigen Specific to Human Bladder Cancer", *Cancer Res.*, vol. 67, No. 7, pp. 3276-3285 (2007).
U.S. Appl. No. 12/438,651, filed Feb. 24, 2009, 62 pages.
Kangawa, et al, "Neuromedin K: A Novel Mammalian Tachykinin Identified in Porcine Spinal Cord", *Biochem Biophys Res Commun.*, vol. 114, No. 2, pp. 533-540 (1983).
Murray, et al., *Human Biochemistry*, publishing house MIR, 1:34 (1993), with English Translation, 6 pages.
Harig, et al., "Induction of cytotoxic T-cell responses against immunoglobulin V region-derived peptides modified at human leukocyte antigen-A2 binding residues", *Blood*, vol. 98, No. 10, pp. 2999-3005 (2001).
Dionne, et al., "Functional characterization of CTL against gp100 altered ligands", *Cancer Immunol Immunother*. vol. 52, No. 4, pp. 199-206 (2003).
Dionne, et al., "Her-2/neu altered peptide ligand-induced CTL responses: implications for peptides with increased HLA affinity and T-cell-receptor interaction", *Cancer Immunol Immunother*. vol. 53, No. 4, pp. 307-314 (2004).
Zarema, et al., "Identification of an Enhancer Agonist Cytotoxic T Lymphocytes Peptide from Human Carcinoembryonic Antigen", *Cancer Res.*, vol. 57, No. 20, pp. 4570-4577 (1997).
Uchida, et al., "Ring Finger Protein 43 as a New Target for Cancer Immunotherapy", *Clin Cancer Res.*, vol. 10, vol. 24, pp. 8577-8586 (2004).
Komori, et al., "Identification of HLA-A2- or HLA-A24-Restricted CTL Epitopes Possibly Useful for Glypican-3-Specific Immunotherapy of Hepatocellular Carcinoma", *Clin Cancer Res.*, vol. 12, No. 9, pp. 2689-2697 (2006).
Schartz, et al., "From the antigen-presenting cell to the antigen-presenting vesicle: The exosomes", *Curr Opin Mol Ther.*, vol. 4, No. 4, pp. 372-381 (2002).
Rammensee, et al., "MHC ligands and peptide motifs: first listing", *Immunogenetics*, vol. 41, No. 4, pp. 178-228 (1995).
Ito, et al., "Identification of Bladder Cancer Antigens Reconigized by IgG Antibodies of a Patient with Metastatic Bladder Cancer", *Int J Cancer*, vol. 108, No. 5, pp. 712-724 (2004).
Adams, et al., "Prediction of binding to MHC class I molecules", *J Immunol Methods*, vol. 185, No. 2, pp. 181-190 (1995).
Kubo, et al., "Definition of Specific Petptide Motifs for Four Major HLA-A Alleles", *J Immunol*, vol. 152, No. 8, pp. 3913-3924 (1994).
Parker, et al., "Scheme for Ranking Potential HLA-A2 Binding Peptides Based on Independent Binding of Individual Peptide Side-Chains", *J Immunol.*, vol. 152, No. 1, pp. 163-175 (1994).
Kondo, et al., "Prominent Roles of Secondary Anchor Residues in Peptide Binding to HLA-A24 Human Class I Molecules", *J Immunol.* vol. 155, No. 9, pp. 4307-4312 (1995).
Hoffmann, et al., "The Ability of Variant Peptides to Reverse the Nonresponsiveness of T Lymphocytes to the Wild-Type Sequence p53264-272 Epitope", *J Immunol.* vol. 168, No. 3, pp. 1338-1347 (2002).
Lutgendorf, et al., "Diurnal Control Variations and Symptoms in Patients with Interstitial Cystitis", *J. Urol.*, vol. 167, No. 3, pp. 1338-1343 (2002).
Falk, et al., "Allele-specific motifs revealed by sequencing of self-peptides eluted from MHC molecules", *Nature*, vol. 351, No. 6324, pp. 290-296 (1991).
Schueler-Furman, et al., "Structure-based prediction of binding peptides to MHC class I molecules: Application to a broad range of MHC alleles", *Protein Sci.*, vol. 9, No. 9, pp. 1838-1846 (2000).
Yamagami, "Antigenic peptide therapy for tumors 3 (Ayumi) cancer immunotherapy using CEA antigenic peptides", *Igaku No Ayumi.*, vol. 190, No. 2, p. 135-138 (1999), with English Translation, 10 pages.
Akiyoshi, "Antigenic peptide therapy for tumors 4 (Ayumi) vaccine therapy using MAGE antigenic peptides", *Igaku No Ayumi.*, vol. 190, No. 2, pp. 139-142 (1999), , with English Translation, 10 pages.
Akiyoshi, "Current Cancer Vaccine Therapy Research—Trials Using Peptide Derived from Tumor-Rejected Antigen", *Gan To Kagakuryouho.*, vol. 24, No. 5, pp. 511-519 (1997), with English Translation, 20 pages.
Mao, et al, Geneseq Accession No. ABB05654 Apr. 29, 2002 "Human DNA binding protein RFX2-89 N-terminal peptide SEQ ID No. 7" (2001).
Uger, et al, Geneseq Accession No. ADB39054 Dec. 4, 2003 "Human tumour derived peptide Tyr 171" (2003).

(56) References Cited

OTHER PUBLICATIONS

Rammensee, et al., Geneseq Accession No. AEG71129 Jun. 1, 2006 "Human tumor associated T-helper cell peptide epitope SEQ ID No. 89" (2006).

International Search Report dated Oct. 2, 2012 for International Patent Application No. PCT/JP2012/005076, 2 pages.

U.S. Appl. No. 14/667,560, filed Mar. 24, 2015, 98 pages.

Ishizaki et al. "Inhibition of Tumor Growth with Antiangiogenic Cancer Vaccine Using Epitope Peptides Derived from Human Vascular Endothelial Growth Factor Receptor 1," Clin Cancer Res 2006;12(19) Oct. 1, 2006, pp. 5841-5849.

Lee et al., "Increased Vaccine-Specific T Cell Frequency After Peptide-based Vaccination Correlates with Increased Susceptibility to In Vitro Stimulation but Does not Lead to Tumor Regression," J Immunol. Dec. 1, 1999;163(11):6292-300.

Mayfield, "Progression-free survival: patient benefit or lower standard," NCI Cancer Bulletin, May 13, 2008 5(10), pp. 8-9.

Schwartzentruber et al., "gp100 Peptide Vaccine and Interleukin-2 in Patients with Advanced Melanoma," New England Journal of Medicine, Jun. 2, 2011 364(22):2119-27.

"Guidance for Industry Clinical Considerations for Therapeutic Cancer Vaccines" U.S. Department of Health and Human Services, Food and Drug Administration, Center for Biologics Evaluation and Research, Oct. 2011, pp. 1-16.

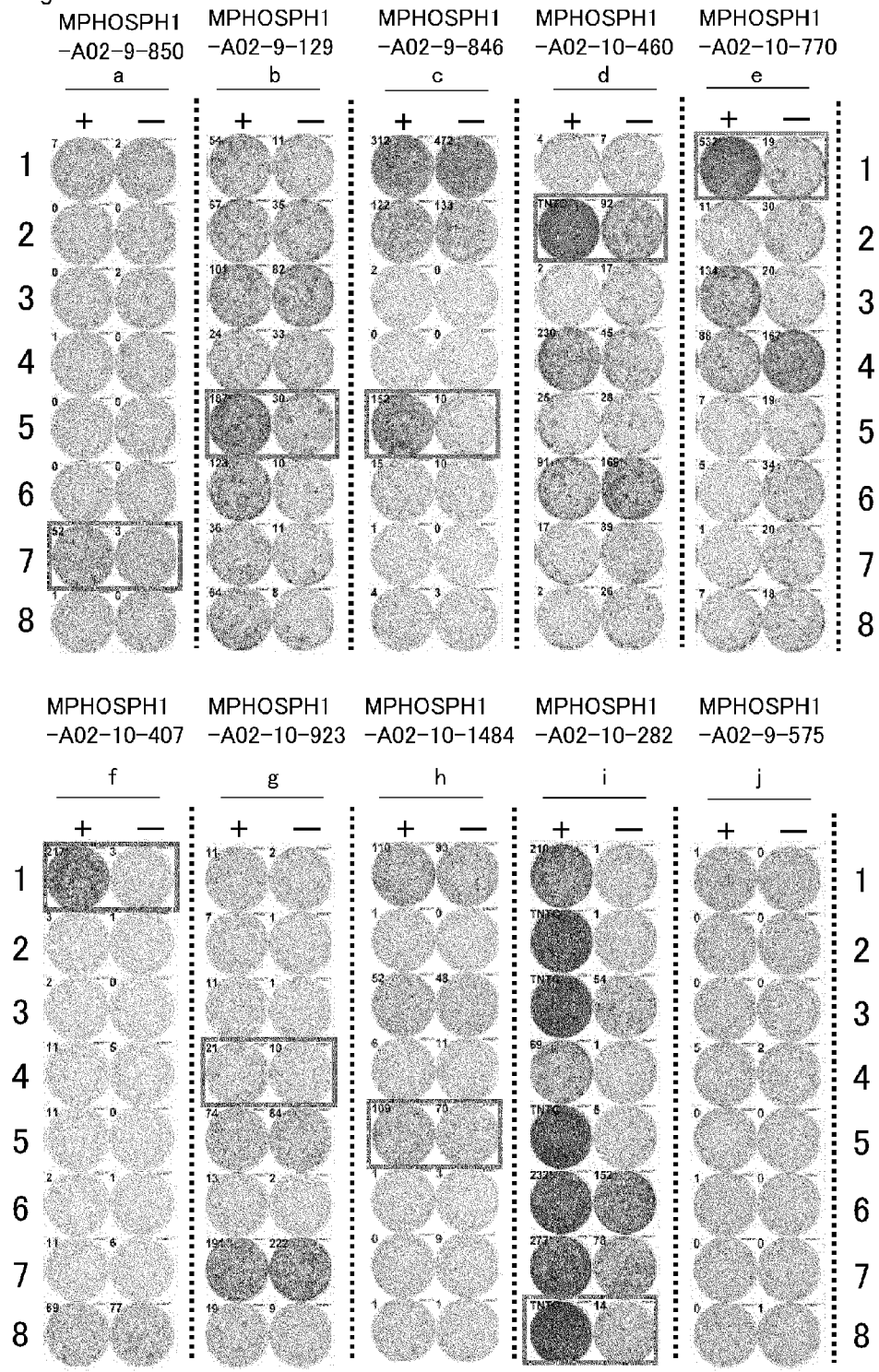

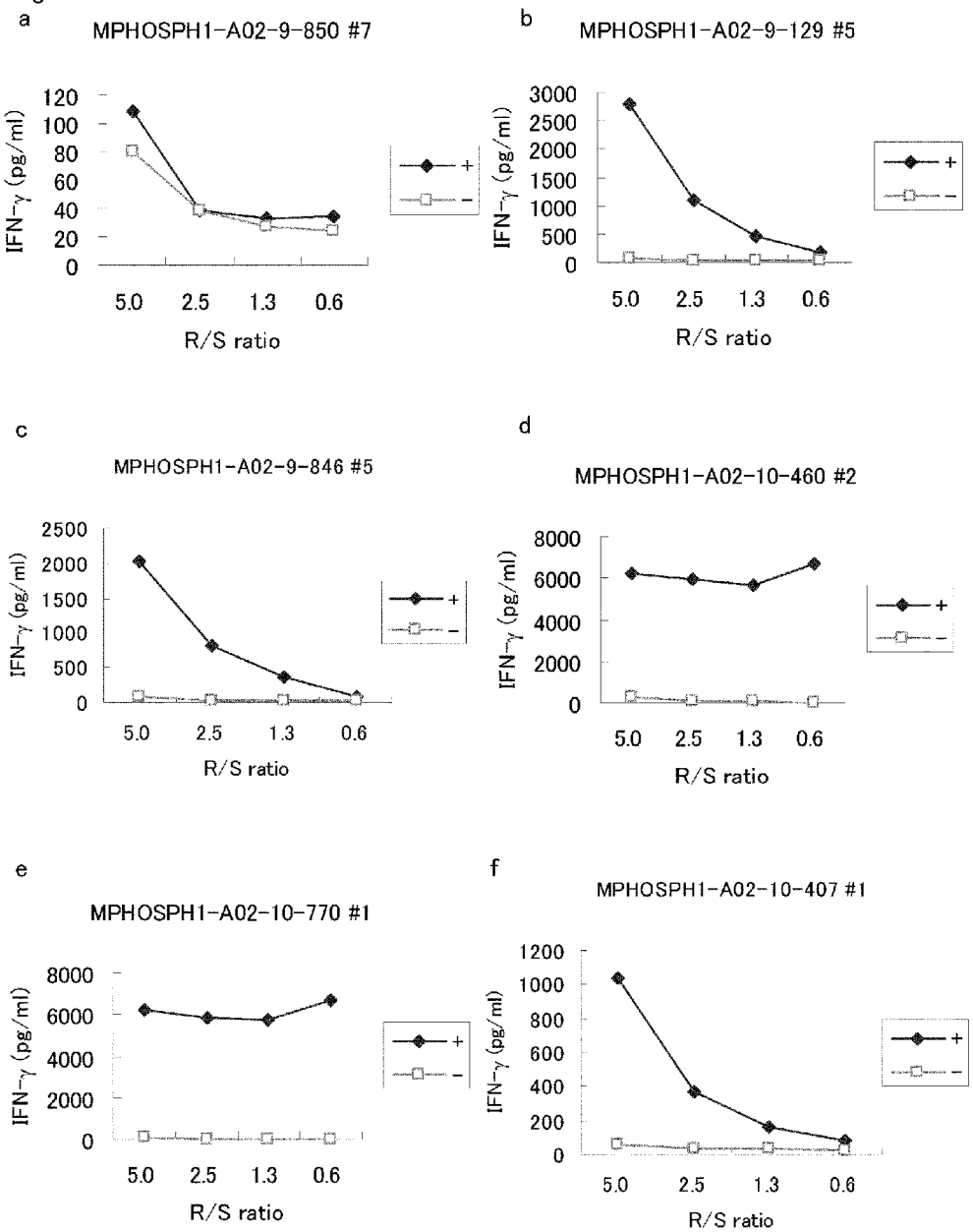
Fig. 2a-f

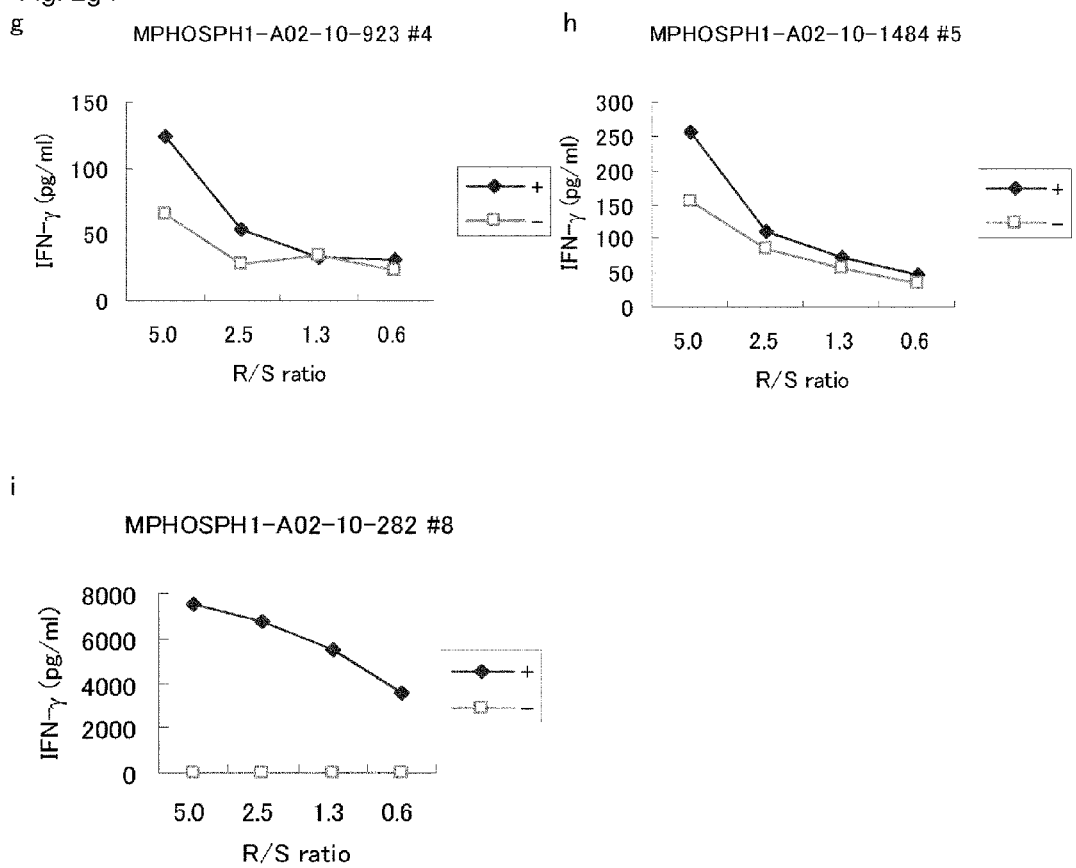

Fig. 3
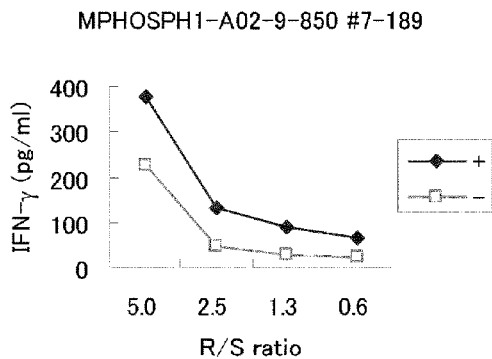
a
MPHOSPH1-A02-9-850 #7-189
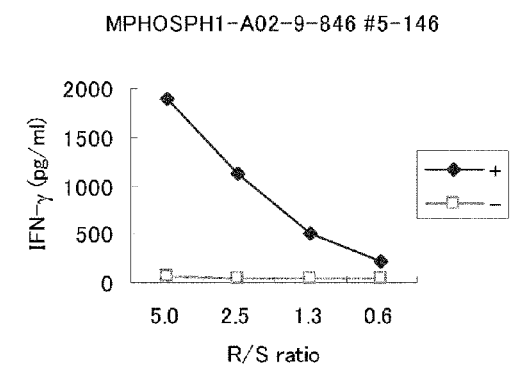
b
MPHOSPH1-A02-9-846 #5-146
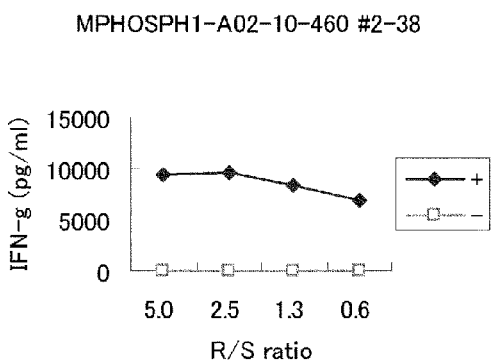
c
MPHOSPH1-A02-10-460 #2-38
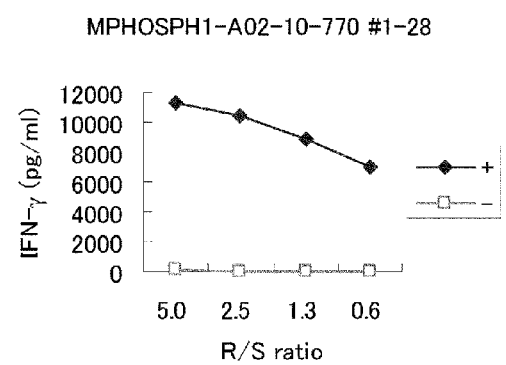
d
MPHOSPH1-A02-10-770 #1-28
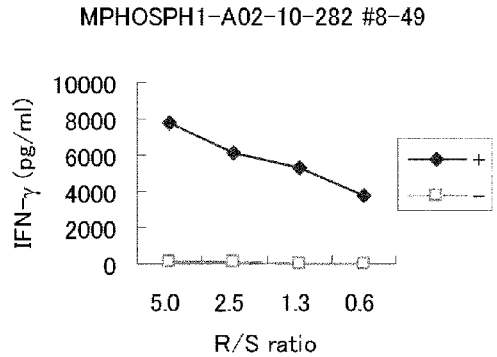
e
MPHOSPH1-A02-10-282 #8-49

MPHOSPH1 PEPTIDES AND VACCINES INCLUDING THE SAME

PRIORITY

The present application is a U.S. National Phase of PCT/JP2012/005076, filed Aug. 9, 2012, which claims the benefit of U.S. Provisional Application No. 61/522,991, filed on Aug. 12, 2011, the entire contents of which are incorporated by reference herein in their entirety.

TECHNICAL FIELD

The present invention relates to the field of biological science, more specifically to the field of cancer therapy. In particular, the present invention relates to novel peptides that are effective as cancer vaccines, as well as drugs for either or both of treating and preventing tumors.

REFERENCE TO SEQUENCE LISTING

This application includes a Sequence Listing as a text file named "87331-026810US-895080_SEQ_LIST.txt" created Dec. 16, 2013, and containing 70,527 bytes. The material contained in this text file is incorporated by reference in its entirety for all purposes.

BACKGROUND ART

Cytotoxic T lymphocytes (CTLs) have been shown to recognize epitope peptides derived from tumor-associated antigens (TAAs) found on major the histocompatibility complex (MHC) class I molecule, and then kill the tumor cells. Since the discovery of the melanoma antigen (MAGE) family, many other TAAs have been discovered through immunological approaches (NPL 1, Boon T, Int J Cancer 1993 May 8, 54(2): 177-80; NPL 2, Boon T & van der Bruggen P, J Exp Med 1996 Mar. 1, 183(3): 725-9). Some of these TAAs are currently undergoing clinical development as immunotherapeutic targets.

Favorable TAAs are indispensable for the proliferation and survival of cancer cells. The use of such TAAs as targets for immunotherapy may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses, warrants further development and thus the clinical application of peptide vaccination strategies for various types of cancer is ongoing (NPL 3, Harris C C, J Natl Cancer Inst 1996 Oct. 16, 88(20): 1442-55; NPL 4, Butterfield L H et al., Cancer Res 1999 Jul. 1, 59(13): 3134-42; NPL 5, Vissers J L et al., Cancer Res 1999 Nov. 1, 59(21): 5554-9; NPL 6, van der Burg S H et al., J Immunol 1996 May 1, 156(9): 3308-14; NPL 7, Tanaka F et al., Cancer Res 1997 Oct. 15, 57(20): 4465-8; NPL 8, Fujie T et al., Int J Cancer 1999 Jan. 18, 80(2): 169-72; NPL 9, Kikuchi M et al., Int J Cancer 1999 May 5, 81(3): 459-66; NPL 10, Oiso M et al., Int J Cancer 1999 May 5, 81(3): 387-94). To date, several clinical trials using these tumor-associated antigen derived peptides have been reported. Unfortunately, many of the current cancer vaccine trial have shown only a low objective response rate (NPL 11, Belli F et al., J Clin Oncol 2002 Oct. 15, 20(20): 4169-80; NPL 12, Coulie P G et al., Immunol Rev 2002 October, 188: 33-42; NPL 13, Rosenberg S A et al., Nat Med 2004 September, 10(9): 909-15). Accordingly, there remains a need in the art for new TAAs as immunotherapeutic targets.

MPHOSPH1 (M-phase phosphoprotein 1; GenBank Accession No. NM_016195 and NP_057279, SEQ ID NO: 125 and 126), was identified as one of the proteins specifically phosphorylated at the G2/M transition and characterized as a plus-end-directed kinesin related protein (NPL 14, Abaza A et al., J Biol Chem 2003, 278: 27844-52.). More particularly, MPHOSPH1 has been reported to be a plus-end-directed molecular motor that plays a crucial role in cytokinesis, and accumulates in the midzone of the spindle during anaphase to telophase in HeLa cells (NPL 14, Abaza A et al., J Biol Chem 2003, 278: 27844-52; NPL 15, Kamimoto T et al., J Biol Chem 2001, 276: 37520-8). In the course of gene expression profile analyses using a genome-wide cDNA microarray containing 23,040 genes, MPHOSPH1 was identified as a novel molecule up-regulated in bladder cancer (NPL 16, Kanehira M et al., Cancer Res. 2007 Apr. 1; 67(7):3276-85; PTL 1, WO2006/085684). Furthermore, through northern blot analysis, expression of the MPHOSPH1 gene products were found to be limited to the testis and absent from the normal vital organs.

Some peptide fragments derived from MPHOSPH1 having cytotoxic T lymphocyte (CTL) inducibility were previously identified (PTL 2, WO2008/047473). These peptide fragments demonstrated the ability to induce CTLs against cells stimulated with the cognate peptide fragments. However, previous studies failed to confirm whether the peptide fragments had the ability to induce CTLs targeting tumor cells expressing the MPHOSPH1 gene and HLA-A2 antigen.

CITATION LIST

Patent Literature

[PTL 1] WO2006/085684
[PTL 2] WO2008/047473

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] Abaza A et al., J Biol Chem 2003, 278: 27844-52.

[NPL 15] Kamimoto T et al., J Biol Chem 2001, 276: 37520-8

[NPL 16] Kanehira M et al., Cancer Res. 2007 Apr. 1; 67(7):3276-85.

SUMMARY OF INVENTION

The present invention is based, at least in part, on the discovery of novel peptides that may serve as suitable targets of immunotherapy. Because TAAs are generally perceived by the immune system as "self" and therefore often have no immunogenicity, the discovery of appropriate targets is of extremely importance. As noted above, MPHOSPH1 (for example, SEQ ID NO: 126 encoded by the gene of GenBank Accession No. NM_016195 (SEQ ID NO: 125)) has been identified as up-regulated in cancers, examples of which include, but are not limited to, bladder cancer, breast cancer, cervical cancer, cholangiocellular carcinoma, chronic myeloid leukemia (CML), colorectal cancer, gastric cancer, non-small cell lung cancer (NSCLC), lymphoma, osteosarcoma, prostate cancer, renal cancer and soft tissue tumor. Thus, the present invention focuses on MPHOSPH1 as a candidate target of cancer/tumor immunotherapy, more particularly novel MPHOSPH1 epitope peptides that may serve as suitable immunotherapeutic targets.

To that end, the present invention is directed, at least in part, to the identification of specific epitope peptides that possess the ability to induce CTLs specific to MPHOSPH1 among peptides derived from MPHOSPH1. As discussed in greater detail below, peripheral blood mononuclear cells (PBMCs) obtained from a healthy donor were stimulated using HLA-A*0201 binding candidate peptides derived from MPHOSPH1. CTL lines were then established with specific cytotoxicity against the HLA-A2 positive target cells pulsed with each of candidate peptides. The results herein demonstrate that these peptides are HLA-A2 restricted epitope peptides that may induce potent and specific immune responses against cells expressing MPHOSPH1. These results further indicate that MPHOSPH1 is strongly immunogenic and the epitopes thereof are effective targets for cancer/tumor immunotherapy.

Accordingly, it is an object of the present invention to provide isolated peptides that bind HLA antigen and induce CTLs, wherein the peptides include an immunologically active fragment of MPHOSPH1 (SEQ ID NO: 126). Such peptides can be used to induce CTLs in vitro or ex vivo, or to be administered directly to a subject so as to induce in vivo immune responses against cancers, examples of which include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

The peptides of the present invention are generally less than 15, 14, 13, 12, 11, or 10 amino acids in length. Preferred peptides of the present invention are nonapeptides or decapeptides. Particularly preferred peptides have an amino acid sequence selected from among SEQ ID NOs: 5, 14, 64, 73, 77, 79, 97, 103 and 120, since those peptides demonstrated to bind to the HLA-A2 antigen and induce CTL.

Thus, in some embodiments, the peptides of the present invention are peptides of less than 15, 14, 13, 12, 11, or 10 amino acids in length that have an amino acid sequence selected from among SEQ ID NOs: 5, 14, 64, 73, 77, 79, 97, 103 and 120. In typical embodiments, the peptides of the present invention are nonapeptides or decapeptides having an amino acid sequence selected from among SEQ ID NOs: 5, 14, 64, 73, 77, 79, 97, 103 and 120. Furthermore, as demonstrated herein, a peptide having the amino acid sequence of SEQ ID NO: 120 was confirmed to induce CTLs targeting tumor cells expressing the MPHOSPH1 and HLA-A2 antigen. Thus, in preferred embodiments, the peptides of the present invention are peptides having an amino acid sequence of SEQ ID NO: 120.

When contacted with antigen presenting cells (APCs) in vitro, ex vivo or in vivo, the peptides of the present invention will bind with HLA-A2 antigens on APCs and be presented on APCs as complexes with HLA-A2 antigens. Alternatively, the peptides of the present invention may be taken into by APCs, processed to fragments composed of an amino acid sequence selected from among SEQ ID NOs: 5, 14, 64, 73, 77, 79, 97, 103 and 120 in APCs, and presented on APCs as complexes with HLA-A2 antigens. Consequently, CTLs specific to such peptides are induced and such CTLs are considered to be as elements of the present invention.

The present invention also contemplates modified peptides having an amino acid sequence in which one, two or several amino acids are substituted, deleted, inserted and/or added in the amino acid sequence selected from among SEQ ID NOs: 5, 14, 64, 73, 77, 79, 97, 103 and 120, so long as the modified peptides retain the CTL inducibility equivalent to that of the original unmodified peptide. To that end, the present invention provides an isolated peptide of less than 15, 14, 13, 12, 11, or 10 amino acids in length, which has CTL inducibility and comprises the amino acid sequence selected from the group consisting of:

(i) an amino acid sequence that 1, 2, or several amino acid(s) are substituted in the amino acid sequence selected from the group consisting of SEQ ID NOs: 5, 14 and 64, and (ii) the amino acid sequence of (i), wherein the amino acid sequence has one or both of the following characteristics:

(a) the second amino acid from the N-terminus of said SEQ ID NO is selected from the group consisting of leucine and methionine; and (b) the C-terminal amino acid of said SEQ ID NO is selected from the group consisting of valine and leucine.

Moreover, the present invention also provides an isolated peptide of less than 15, 14, 13, 12, or 11 amino acids in length, which has CTL inducibility and comprises the amino acid sequence selected from the group consisting of:

(i') an amino acid sequence that 1, 2, or several amino acid(s) are substituted in the amino acid sequence selected from the group consisting of SEQ ID NOs: 73, 77, 79, 97, 103 and 120, and (ii') the amino acid sequence of (i'), wherein the amino acid sequence has one or both of the following characteristics:

(a) the second amino acid from the N-terminus of said SEQ ID NO is selected from the group consisting of leucine and methionine; and (b) the C-terminal amino acid of said SEQ ID NO is selected from the group consisting of valine and leucine.

As demonstrated herein, such peptides may bind with HLA-A2 antigens on APCs and be presented on APCs as complexes with HLA-A2 antigens. Alternatively, such peptides may be taken into by APCs, processed to fragments composed of an amino acid sequence selected from among (i), (ii), (i'), and (ii') in APCs, and presented on APCs as complexes with HLA-A2 antigens, when those peptides are contacted with APCs. Consequently, CTLs specific to such peptides are induced and such CTLs are considered to be as elements of the present invention.

The present invention further encompasses isolated polynucleotides that encode any of the peptides of the present invention. These polynucleotides can be used to induce or prepare APCs having CTL inducibility. Like above-described peptides of the present invention, such APCs can be administered to a subject for inducing immune responses against cancers.

When administered to a subject, the peptides of the present invention are presented on the surface of APCs so as to induce CTLs targeting the respective peptides. Therefore, one object of the present invention is to provide agents or compositions that include one or more peptide(s) or polynucleotide(s) provided by the present invention for inducing either or both of APCs and CTLs. Such agents or compositions can be also used for one or more purpose(s) selected from among the treatment of cancer, the prophylaxis of cancer, and the prevention of postoperative recurrence of cancer. Examples of targeted cancers include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor. Thus, it is yet another object of the present invention is to provide pharmaceutical agents or compositions for either or both of the treatment of cancer and the prophylaxis of cancer, such pharmaceutical agents or compositions formulated to include one or more peptides or polynucleotides of the present invention. Instead of or in addition to the peptides or polynucleotides of the present invention, the pharmaceutical agents or compositions of the present invention may include as active ingredients APCs or exosomes that present any of the peptides of the present invention.

The peptides or polynucleotides of the present invention may be used to induce APCs that present on the surface a complex of an HLA antigen and a present peptide, for example, by contacting APCs with the peptide of the present invention or introducing a polynucleotide encoding a peptide of the present invention into APCs. Such APCs have the ability of inducing CTLs that specifically recognize cells that presents target peptides on their surface and find use in cancer immunotherapy. Accordingly, the present invention encompasses the methods for inducing APCs having CTL inducibility as well as the APCs obtained by such methods. In addition, the present invention also encompasses the agents or compositions for use in inducing APCs, such agents or compositions including any peptides or polynucleotides of the present invention.

It is further object of the present invention to provide a method for inducing CTLs, such method including the step of co-culturing CD8 positive T cells with APCs or exosomes presenting the peptide of the present invention on its surface or the step of introducing a polynucleotide encoding both of T cell receptor (TCR) subunits or polynucleotides encoding each of TCR subunits, wherein the TCR can binds to a complex of the peptide of the present invention and HLA antigen presented on cell surface. CTLs obtained by such methods can find use in either or both of the treatment of cancer and the prevention of cancer. Examples of cancers include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

Yet another object of the present invention is to provide isolated APCs that present on the surface a complex of an HLA antigen and a peptide of the present invention. The present invention further provides isolated CTLs that target peptides of the present invention. These APCs and CTLs find utility in the context of cancer immunotherapy.

It is yet another object of the present invention to provide methods for inducing an immune response against a cancer in a subject in need thereof, such methods including the step of administering an agent or composition that include at least one component selected from among the peptides of the present invention, polynucleotides encoding such peptides, exosomes or APCs presenting such peptides and CTLs that recognize cells presenting such peptides on their surface.

The applicability of the present invention extends to any of a number of the diseases relating to or arising from MPHOSPH1 over-expression, such as cancer, examples of which include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

More specifically, the present invention provides followings:

[1] An isolated peptide of the following (a) or (b):

(a) a peptide comprising an amino acid sequence selected from the group consisting of SEQ ID NOs: 5, 14, 64, 73, 77, 79, 97, 103 and 120;

(b) a peptide comprising an amino acid sequence that 1, 2, or several amino acid(s) are substituted, deleted, inserted, and/or added in the amino acid sequence selected from the group consisting of SEQ ID NOs: 5, 14, 64, 73, 77, 79, 97, 103 and 120, and wherein the peptide has cytotoxic T lymphocyte (CTL) inducibility,

[2] The isolated peptide of [1], wherein the peptide has one or both of the following characteristics:

(a) the second amino acid from the N-terminus of the amino acid sequence selected from the group consisting of SEQ ID NOs: 5, 14, 64, 73, 77, 79, 97, 103 and 120 is selected from the group consisting of leucine and methionine; and (b) the C-terminal amino acid of the amino acid sequence selected from the group consisting of SEQ ID NOs: 5, 14, 64, 73, 77, 79, 97, 103 and 120 is selected from the group consisting of valine and leucine,

[3] The isolated peptide of [1] or [2], wherein the peptide is a nonapeptide or decapeptide,

[4] An isolated polynucleotide encoding the peptide of any one of [1] to [3],

[5] A composition for inducing a CTL, wherein the composition comprises one or more peptide(s) of any one of [1] to [3], or one or more polynucleotide(s) of [4],

[6] A composition for inducing an APC having CTL inducibility, wherein the composition comprises one or more peptide(s) of any one of [1] to [3], or one or more polynucleotide(s) of [4],

[7] A pharmaceutical composition comprising at least one active ingredient selected from the group consisting of:

(a) one or more peptides of any one of [1] to [3];

(b) one or more polynucleotides encoding the peptide of any one of [1] to [3];

(c) one or more APCs or exosomes that present a complex of the peptide of any one of [1] to [3] and an HLA antigen on their surface; and (d) one or more CTLs that recognize a cell presenting a complex of the peptide of any one of [1] to [3] and an HLA antigen on its surface,

[8] The pharmaceutical composition of [7] for use in either or both of the treatment and the prophylaxis of cancer, or inducing an immune response against cancer in a subject,

[9] The pharmaceutical composition of [7] or [8], wherein the pharmaceutical composition is formulated for administration to a subject whose HLA antigen is HLA-A2,

[10] A method for inducing an antigen-presenting cell (APC) having CTL inducibility, said method comprising a step selected from the group consisting of:
(a) contacting an APC with the peptide of any one of [1] to [3] in vitro, ex vivo or in vivo, and
(b) introducing a polynucleotide encoding the peptide of any one of [1] to [3] into an APC,

[11] A method for inducing a CTL, said method comprising a step selected from the group consisting of:
(a) co-culturing a CD8 positive T cell with an APC that presents on its surface a complex of an HLA antigen and the peptide of any one of [1] to [3];
(b) co-culturing a CD8 positive T cell with an exosome that presents on its surface a complex of an HLA antigen and the peptide of any one of [1] to [3]; and
(c) introducing a polynucleotide encoding both of T cell receptor (TCR) subunits or polynucleotides encoding each of TCR subunits into a CD8 positive T cell, wherein the TCR can bind to a complex of an HLA antigen and the peptide of any one of [1] to [3] presented on a cell surface,

[12] An isolated APC that presents on its surface a complex of an HLA antigen and the peptide of any one of [1] to [3],

[13] The APC of [12], which is induced by the method of [10],

[14] An isolated CTL that recognizes a cell presenting on its surface a complex of an HLA antigen and the peptide of any one of [1] to [3],

[15] The CTL of [14], wherein said CTL is induced by the method of [11],

[16] A method of either or both of the treatment and prophylaxis of cancer in a subject, wherein the method comprises the step of administering to the subject (a) pharmaceutically effective amount(s) of:
(a) one or more peptides of any one of [1] to [3];
(b) one or more polynucleotides encoding the peptide of any one of [1] to [3];
(c) one or more APCs or exosomes that present a complex of the peptide of any one of [1] to [3] and an HLA antigen on their surface; or
(d) one or more CTLs that recognize a cell presenting a complex of the peptide of any one of [1] to [3] and an HLA antigen on its surface,

[17] A method of inducing an immune response against cancer in a subject in need thereof, said method comprising the step of administering to the subject a composition comprising a peptide of any one of [1] to [3] or a polynucleotide encoding the peptide,

[18] An antibody or immunologically active fragment thereof against the peptide of any one of [1] to [3],

[19] A vector comprising a nucleotide sequence encoding the peptide of any one of [1] to [3],

[20] A host cell transformed or transfected with the vector of [19], and

[21] A diagnostic kit comprising the peptide of any one of [1] to [3], the polynucleotide of [4] or the antibody of [18].

Objects and features of the invention will become more fully apparent when the following detailed description is read in conjunction with the accompanying figures and examples. It is to be understood that both the foregoing summary of the present invention and the following detailed description are of exemplified embodiments, and not restrictive of the present invention or other alternate embodiments of the present invention.

In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn there from, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments that follow.

FIG. 1 is composed of a series of photographs, (a) to (j), depicting the results of IFN-gamma ELISPOT assays on CTLs that were induced with peptides derived from MPHOSPH1. The CTLs in well number #7 stimulated with MPHOSPH1-A02-9-850 (SEQ ID NO: 5) (a), in #5 stimulated with MPHOSPH1-A02-9-129 (SEQ ID NO: 14) (b), in #5 stimulated with MPHOSPH1-A02-9-846 (SEQ ID NO: 64) (c), in #2 stimulated with MPHOSPH1-A02-10-460 (SEQ ID NO: 73) (d), in #1 stimulated with MPHOSPH1-A02-10-770 (SEQ ID NO: 77) (e), in #1 stimulated with MPHOSPH1-A02-10-407 (SEQ ID NO: 79) (f), in #4 stimulated with MPHOSPH1-A02-10-923 (SEQ ID NO: 97) (g), in #5 stimulated with MPHOSPH1-A02-10-1484 (SEQ ID NO: 103) (h) and in #8 stimulated with MPHOSPH1-A02-10-282 (SEQ ID NO: 120) (i) showed potent IFN-gamma production as compared with the control, respectively. The square on the well of these pictures indicates that the cells from corresponding well were expanded to establish CTL lines. In contrast, as typical case of negative data, specific IFN-gamma production from the CTL stimulated with MPHOSPH1-A02-9-575 (SEQ ID NO: 1) (j) was not shown. In the figures, "+" indicates the IFN-gamma production against target cells pulsed with the appropriate peptide, and "−" indicates the IFN-gamma production against target cells not pulsed with any peptides.

FIG. 2a-f is composed of a series of line graphs, (a) to (f), depicting the results of an IFN-gamma ELISA assay demonstrating the IFN-gamma production of CTL lines stimulated with MPHOSPH1-A02-9-850 (SEQ ID NO: 5) (a), MPHOSPH1-A02-9-129 (SEQ ID NO: 14) (b), MPHOSPH1-A02-9-846 (SEQ ID NO: 64) (c), MPHOSPH1-A02-10-460 (SEQ ID NO: 73) (d), MPHOSPH1-A02-10-770 (SEQ ID NO: 77) (e), and MPHOSPH1-A02-10-407 (SEQ ID NO: 79) (f). The quantity of IFN-gamma which CTL lines produced was measured by IFN-gamma enzyme-linked immunosorbent assay (ELISA). The results demonstrate that CTL lines established by stimulation with each peptide show potent IFN-gamma production as compared with the control. In the figures, "+" indicates the IFN-gamma production against target cells pulsed with the appropriate peptide, and "−" indicates the IFN-gamma production against target cells not pulsed with any peptides. R/S ratio indicates the ratio of the number of responder cells (CTL line) and stimulator cells.

FIG. 2g-i is composed of a series of line graphs, (g) to (i), depicting the results of an IFN-gamma ELISA assay demonstrating the IFN-gamma production of CTL lines stimulated with MPHOSPH1-A02-10-923 (SEQ ID NO: 97) (g), MPHOSPH1-A02-10-1484 (SEQ ID NO: 103) (h) and MPHOSPH1-A02-10-282 (SEQ ID NO: 120) (i). The quantity of IFN-gamma which CTL lines produced was measured by IFN-gamma enzyme-linked immunosorbent assay (ELISA). The results demonstrate that CTL lines established by stimulation with each peptide show potent IFN-gamma production as compared with the control. In the figures, "+" indicates the IFN-gamma production against target cells pulsed with the appropriate peptide, and "−" indicates the IFN-gamma production against target cells not pulsed with any peptides. R/S ratio indicates the ratio of the number of responder cells (CTL line) and stimulator cells.

FIG. 3 is composed of a series of line graphs, (a) to (e), depicting the IFN-gamma production of the CTL clones established by limiting dilution from the CTL lines stimulated with MPHOSPH1-A02-9-850 (SEQ ID NO: 5) (a), MPHOSPH1-A02-9-846 (SEQ ID NO: 64) (b), MPHOSPH1-A02-10-460 (SEQ ID NO: 73) (c), MPHOSPH1-A02-10-770 (SEQ ID NO: 77) (d) and MPHOSPH1-A02-10-282 (SEQ ID NO: 120) (e). The results demonstrate that the CTL clones established by stimulation with each peptide show potent IFN-gamma production as compared with the control. In the figure, "+" indicates the IFN-gamma production against target cells pulsed with the appropriate peptide and "−" indicates the IFN-gamma production against target cells not pulsed with any peptides. R/S ratio indicates the ratio of the number of responder cells (CTL clone) and stimulator cells.

DESCRIPTION OF EMBODIMENTS

Figure 4:
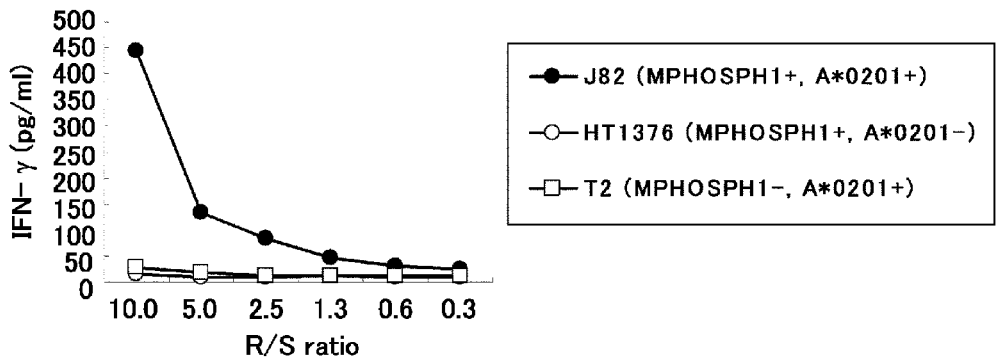
FIG. 4 is a line graph depicting specific CTL activity against the tumor cell lines. J82 cells which express both MPHOSPH1 and HLA-A*0201, HT1376 cells which express MPHOSPH1 but not HLA-A*0201 and T2 cells which express HLA-A*0201 but not MPHOSPH1 were used as stimulator cells. The CTL clone established with MPHOSPH1-A02-10-282 (SEQ ID NO: 120) showed specific CTL activity against J82 cells. On the other hand, no significant specific CTL activity was detected against HT1376 and T2 cells. R/S ratio indicates the ratio of the number of the responder cells (CTL clone) and the stimulator cells.

Although any methods and materials similar or equivalent to those described herein can be used in the practice or testing of embodiments of the present invention, the preferred methods, devices, and materials are now described. However, before the present materials and methods are described, it should be understood that these descriptions are merely illustrative only and not intended to be limiting. It should also be understood that the present invention is not limited to the particular sizes, shapes, dimensions, materials, methodologies, protocols, etc. described herein, as these may vary in accordance with routine experimentation and/or optimization. Furthermore, the terminology used in the description is for the purpose of describing the particular versions or embodiments only, and is not intended to limit the scope of the present invention that will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

I. DEFINITIONS

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to peptide that are substantially free of cellular material such as carbohydrate, lipid, or other contaminating proteins from the cell or tissue source from which the peptide is derived, or substantially free of chemical precursors or other chemicals when chemically synthesized. The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "oligopeptide" sometimes used in the present specification is used to refer to peptides of the present invention which are 20 residues or fewer, typically 15 residues or fewer in length and is typically composed of between about 8 and about 11 residues, often 9 or 10 residues. The latter are referred to herein as "nonapeptides" and "decapeptides", respectively.

The term "amino acid" as used herein refers to naturally occurring and synthetic amino acids, as well as amino acid analogs and amino acid mimetics that similarly function to the naturally occurring amino acids. Amino acid may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have one or more modified R group(s) or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotide" and "nucleic acid" are used interchangeably herein and, unless otherwise specifically indicated are similarly to the amino acids referred to by their commonly accepted single-letter codes.

The terms "agent" and "composition" are used interchangeably herein to refer to a product that includes the specified ingredients in the specified amounts, as well as any product that results, directly or indirectly, from combination of the specified ingredients in the specified amounts. Such terms, when used in relation to the modifier "pharmaceutical" (as in "pharmaceutical agent" and "pharmaceutical composition") are intended to encompass a product that includes the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the terms "pharmaceutical agent" and "pharmaceutical composition" refer to any product made by admixing a molecule or compound of the present invention and a pharmaceutically or physiologically acceptable carrier.

The phrase "pharmaceutically acceptable carrier" or "physiologically acceptable carrier", as used herein, means a pharmaceutically or physiologically acceptable material, composition, substance or vehicle, including but not limited to, a liquid or solid filler, diluent, excipient, solvent or encapsulating material.

The pharmaceutical agents or compositions of the present invention find particular use as vaccines. In the context of the present invention, the phrase "vaccine" (also referred to as an "immunogenic composition") refers to an agent or composition that has the function to induce anti-tumor immunity upon inoculation into animals.

The term "active ingredient" herein refers to a substance in an agent or composition that is biologically or physiologically active. Particularly, in the context of pharmaceutical agent or composition, the term "active ingredient" refers to a substance that shows an objective pharmacological effect. For example, in case of pharmaceutical agents or compositions for use in the treatment or prevention of cancer, active ingredients in the agents or compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effect of active ingredients is inductions of CTLs recognizing or killing cancer cells. Before being formulated, the "active ingredient" may also be referred to as "bulk", "drug substance" or "technical product".

Unless otherwise defined, the term "cancer" refers to the cancers that over-express MPHOSPH1 gene, examples of which include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the term "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "subject's (or patient's) HLA antigen is HLA-A2" refers to that the subject or patient homozygously or heterozygously possess HLA-A2 antigen gene as the MHC (major histocompatibility complex) Class I molecule, and HLA-A2 antigen is expressed in cells of the subject or patient as an HLA antigen.

To the extent that the methods and compositions of the present invention find utility in the context of the "treatment" of cancer, a treatment is deemed "efficacious" if it leads to clinical benefit such as a decrease in size, prevalence, or metastatic potential of the cancer in a subject, retarding progression of cancer, alleviation of a clinical symptom of cancer, prolongation of survival time, suppression of postoperative recurrence and so on. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of post operative recurrence thereof, include any activities that lead to, for example, the following events, such as the inhibition of the growth of cancerous cells, the involution or regression of a tumor, the induction of remission, the suppression of occurrence of cancer, the tumor regression, the reduction or inhibition of metastasis, the suppression of postoperative recurrence of cancer, and prolongation of survival time. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multi-specific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM).

II. PEPTIDES

Peptides of the present invention described in detail below may be referred to as "MPHOSPH1 peptide(s)" or "MPHOSPH1 polypeptide(s)".

To demonstrate that peptides derived from MPHOSPH1 function as an antigen recognized by CTLs, peptides derived from MPHOSPH1 (SEQ ID NO: 126) were analyzed to determine whether they were antigen epitopes restricted by HLA-A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A2 binding peptides derived from MPHOSPH1 were identified based on their binding affinities to HLA-A2.

Moreover, after in vitro stimulation of T-cells by dendritic cells (DCs) pulsed (loaded) with these peptides, CTLs were successfully established by stimulating the DCs with each of the following peptides:

MPHOSPH1-A2-9-850, (SEQ ID NO: 5)

MPHOSPH1-A2-9-129, (SEQ ID NO: 14)

MPHOSPH1-A2-9-846, (SEQ ID NO: 64)

MPHOSPH1- A2-10-460, (SEQ ID NO: 73)

MPHOSPH1-A2-10- 770, (SEQ ID NO: 77)

MPHOSPH1-A2-10- 407, (SEQ ID NO: 79)

MPHOSPH1-A2-10- 923, (SEQ ID NO: 97)

MPHOSPH1- A2-10-1484 and (SEQ ID NO: 103)

MPHOSPH1- A2-10-282. (SEQ ID NO: 120)

These established CTLs showed potent specific CTL activity against target cells pulsed with respective peptides. These results demonstrate that MPHOSPH1 is an antigen recognized by CTLs and that the peptides tested are epitope peptides of MPHOSPH1 restricted by HLA-A2; and therefore, the peptides may be effective as target antigens for cytotoxicity by CTLs. Furthermore, MPHOSPH1-A2-10-282 (SEQ ID NO: 120) induced CTLs having potent cytotoxic activity against cancer cells expressing both MPHOSPH1 and HLA-A2 antigen as the MHC Class I molecule. This result suggests that the MPHOSPH1-A2-10-282 peptide occurs naturally in vivo to be presented on cancer cells expressing MPHOSPH1 by HLA-A2 antigen (e.g., HLA-A*0201 or HLA-A*0206). According to the findings, a peptide comprising the amino acid sequence selected from the group consisting of SEQ ID NO: 5, 14, 64, 73, 77, 79, 97, 103 and 120, or derivatives, mutants, variants or modified peptides thereof—are useful in the context of immunological therapy for treating a cancer that expresses MPHOSPH1 and HLA-A2 antigen. In certain embodiments of the present invention, peptide composed of an amino acid sequence disclosed herein can be used for immunological therapy of cancer. Examples of cancers to be treated include, for example, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor. However, the peptides of the present invention can be applied to any cancers, so long as they express MPHOSPH1 and HLA-A2 antigen.

Since the MPHOSPH1 gene is over-expressed in cancer cells such as bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor, but is not expressed in most normal organs, it is a good target for immunotherapy. Thus, the present invention provides nonapeptides (peptides composed of nine amino acid residues) and decapeptides (peptides composed of ten amino acid residues) of CTL-recognized epitopes from MPHOSPH1. Alternatively, the present invention provides isolated peptides which bind to HLA antigens and induce cytotoxic T lymphocytes (CTLs), wherein the peptide is composed of an immunologically active fragment of MPHOSPH1 (SEQ ID NO: 126). More specifically, in some embodiments, the present invention provides peptides comprising an amino acid sequence selected from among SEQ ID NOs: 5, 14, 64, 73, 77, 79, 97, 103 and 120. In preferred embodiments, the peptides of the present invention are peptides that comprise an amino acid sequence of SEQ ID NO: 120.

Generally, software programs now available, for example, on the Internet, such as those described in Parker K C et al., J Immunol 1994 Jan. 1, 152(1): 163-75 and Nielsen M et al., Protein Sci 2003; 12: 1007-17 can be used to calculate the binding affinities between various peptides and HLA antigens in silico. Binding affinity with HLA antigens can be measured as described, for example, in Parker K C et al., J Immunol 1994 Jan. 1, 152(1): 163-75, Kuzushima K et al., Blood 2001, 98(6): 1872-81, Larsen M V et al. BMC Bioinformatics. 2007 Oct. 31; 8: 424, Buus S et al. Tissue Antigens., 62:378-84, 2003, Nielsen M et al., Protein Sci 2003; 12: 1007-17, and Nielsen M et al. PLoS ONE 2007; 2: e796, which are summarized in, e.g., Lafuente E M et al., Current Pharmaceutical Design, 2009, 15, 3209-3220. Methods for determining binding affinity are described, for example, in the Journal of Immunological Methods (1995, 185: 181-190) and Protein Science (2000, 9: 1838-1846). Therefore, one can utilize such software programs to select those fragments derived from MPHOSPH1 that have high binding affinity with HLA antigens. Accordingly, the present invention encompasses peptides composed of any fragments derived from MPHOSPH1, which would be determined to bind with HLA antigens by such known programs. Furthermore, such peptides may include the peptide composed of the full length sequence of MPHOSPH1.

The peptides of the present invention, particularly the nonapeptides and decapeptides of the present invention, may be flanked with additional amino acid residues so long as the peptides retain their CTL inducibility. The particular additional amino acid residues may be composed of any kind of amino acids so long as they do not impair the CTL inducibility of the original peptide. Thus, the present invention encompasses peptides having CTL inducibility, wherein the peptides include an amino acid sequence derived from MPHOSPH1. Such peptides are, for example, less than about 40 amino acids, often less than about 20 amino acids, usually less than about 15 amino acids.

It is generally known that modifications of one, two, several or more amino acids in a peptide do not influence the function of the peptide, or in some cases even enhance the desired function of the original peptide. In fact, modified peptides (i.e., peptides composed of an amino acid sequence modified by substituting, inserting, deleting and/or adding one, two or several amino acid residues to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment of the present invention, the peptide having CTL inducibility of the present invention may be composed of a peptide having an amino acid sequence selected from among SEQ ID NOs: 5, 14, 64, 73, 77, 79, 97, 103 and 120, in which one, two or several amino acids are added, deleted, inserted and/or substituted. In another embodiment, the peptides of the present invention may be peptides comprising an amino acid sequence in which one, two, or several amino acid(s) are substituted, deleted, inserted, and/or added in the amino acid sequence selected from among SEQ ID NOs: 5, 14, 64, 73, 77, 79, 97, 103 and 120, provided the modified peptide retain the CTL inducibility of the original peptide. In preferred embodiments, the peptide of the present invention may be peptides comprising an amino acid sequence in which one, two, or several amino acid(s) are substituted, deleted, inserted, and/or added in the amino acid sequence of SEQ ID NO: 120, provided the modified peptide retain the CTL inducibility of the original peptide.

Those of skill in the art will recognize that individual modifications (i.e., additions, insertions, deletions and/or substitutions) to an amino acid sequence that alter a single amino acid or a small percentage of the overall amino acid sequence tend to result in the conservation of the properties of the original amino acid side-chain; it is thus referred to as "conservative substitution" or "conservative modification", wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic group containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, the peptide of the present invention is not restricted thereto and may include non-conservative modifications, so long as the resulting modified peptide retains the CTL inducibility of the original unmodified peptide. Furthermore, the modified peptides should not exclude CTL inducible peptides derived from polymorphic variants, interspecies homologues, or alleles of MPHOSPH1.

Amino acid residues may be inserted, substituted, deleted and/or added to the peptides of the present invention or, alternatively, amino acid residues may be deleted therefrom to achieve a higher binding affinity. To retain the requisite CTL inducibility, one preferably modifies (inserts, deletes, adds and/or substitutes) only a small number (for example, 1, 2 or several) or a small percentage of amino acids. Herein, the term "several" means 5 or fewer amino acids, for example, 4 or 3 or fewer. The percentage of amino acids to be modified may be, for example, 20% or less, preferably 15% or less, more preferably 10% or less, even more preferably 1 to 5%.

When used in the context of cancer immunotherapy, the peptides of the present invention may be presented on the surface of a cell or exosome as a complex with an HLA antigen. Therefore, it is preferable to select peptides that not only induce CTLs but also possess high binding affinity to the HLA antigen. To that end, the peptides can be modified by substitution, insertion, deletion and/or addition of amino acid residues to yield a modified peptide having improved binding affinity. In addition to peptides that are naturally displayed, since the regularity of the sequences of peptides displayed by binding to HLA antigens has already been known (J Immunol 1994, 152: 3913; Immunogenetics 1995, 41: 178; J Immunol 1994, 155: 4307), modifications based on such regularity may be introduced into the immunogenic peptides of the present invention.

For example, peptides exhibiting high HLA-A2 binding affinity tend to have the second amino acid from the N-terminus substituted with leucine or methionine. Likewise, peptides in which the C-terminal amino acid is substituted with valine or leucine can also be favorably used. Thus, peptides having an amino acid sequence selected from among SEQ ID NOs: 5, 14, 64, 73, 77, 79, 97, 103 and 120 in which the second amino acid from the N-terminus of the amino acid sequence of the SEQ ID NO is substituted with leucine or methionine, and/or wherein the C-terminus of the amino acid sequence of the SEQ ID NO is substituted with valine or leucine are contemplated by the present invention. In another embodiment, the present invention encompasses peptides having an amino acid sequence in which the second amino acid from the N-terminus of the amino acid sequence selected from among of the SEQ ID NOs: 5, 14, 64, 73, 77, 79, 97, 103 and 120 is substituted with leucine or methionine, and/or the C-terminus of the amino acid sequence of the SEQ ID NO is substituted with valine or leucine. In preferred embodiments, the peptides of the present invention may comprise an amino acid sequence in which the second amino acid from the N-terminus of the amino acid sequence of SEQ ID NO: 120 is substituted with leucine or methionine, and/or the C-terminus of the amino acid sequence of the SEQ ID NO is substituted with valine or leucine.

In one embodiment, the present invention provides the peptides having CTL inducibility, wherein the peptides have general formula selected from the group consisting of (1) to (9) as follows:

(SEQ ID NO: 5)
(1) -corresponding to MPHOSPH1-A2-9-850-

F [X1] L T I E N E [X2], (SEQ ID NO: 14)
(2) -corresponding to MPHOSPH1-A2-9-129-

F [X1] G C I M Q P [X2], (SEQ ID NO: 64)
(3) -corresponding to MPHOSPH1-A2-9-846-

G [X1] R A F L L T [X2], (SEQ ID NO: 73)
(4) -corresponding to MPHOSPH1- A2-10-460-

Y [X1] A Y D E T L N [X2], (SEQ ID NO: 77)
(5) -corresponding to MPHOSPH1-A2-10- 770-

K [X1] I C N E T V E [X2]

(SEQ ID NO: 79)
(6) -corresponding to MPHOSPH1-A2-10- 407-

L [X1] T L G K C I N [X2]

(SEQ ID NO: 97)
(7) -corresponding to MPHOSPH1-A2-10- 923-

K [X1] S N E I E T A [X2]

(SEQ ID NO: 103)
(8) -corresponding to MPHOSPH1- A2-10-1484-

Q [X1] V A A L E I Q [X2],
and (SEQ ID NO: 120)
(9) -corresponding to MPHOSPH1- A2-10-282-

Y [X1] Y D L F V P V [X2].

In the general formula (1)-(9), [X1] is leucine or methionine, and [X2] is valine or leucine. In a particularly preferred embodiment of the present invention, the general formula may be (9), which corresponds to SEQ ID NO: 120. The present invention further provides isolated peptide represented by the general formula (1)-(9) defined above, to which one, two, or several amino acids are added at either or both of N-terminus and C-terminus thereof. In an alternative embodiment, the present invention provides isolated peptides represented by the general formula (1)-(9) from which one, two, or several amino acid residues are deleted at either or both of N-terminus and C-terminus thereof. The present invention also provides isolated peptide represented by the general formula (1)-(9), to which one, two, or several amino acids are inserted or deleted at anywhere of the sequence.

Substitutions may be introduced not only at the terminal amino acids but also at the positions of potential T cell receptor (TCR) recognition sites of peptides. Several studies have demonstrated that a peptide with amino acid substitutions may have equal to or better function than that of the original, for example, CAP1, p53$_{(264-272)}$, Her-2/neu$_{(369-377)}$ or gp 100$_{(209-217)}$ (Zaremba et al. Cancer Res. 57, 4570-4577, 1997, T. K. Hoffmann et al. J Immunol. (2002) Feb. 1; 168(3):1338-47., S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids may also be added to either or both of the N and C-terminus of the peptides of the present invention. Such modified peptides retaining CTL inducibility are also included in the present invention.

However, when the peptide sequence is identical to a portion of the amino acid sequence of an endogenous or exogenous protein having a different function, negative side effects such as autoimmune disorders or allergic symptoms against specific substances may be induced. Therefore, it may be desirable to perform homology searches using available databases to avoid situations in which the sequence of the peptide matches the amino acid sequence of another protein. When it becomes clear from the homology searches that no peptide identical to or having a 1 or 2 amino acid difference with respect to the objective peptide exists in nature, the objective peptide may be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility.

Herein, the phrase "CTL inducibility" indicates the ability of a peptide to induce a CTL when presented on an antigen-presenting cell (APC). Further, "CTL inducibility" includes the ability of a peptide to induce CTL activation, CTL proliferation, promote lysis of target cells by CTL, and to increase IFN-gamma production by CTL.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation of APCs with a test peptide, mixing APCs with CD8-positive cells to induce CTLs, and then measuring the IFN-gamma against the target cells produced and released by CTLs. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependent on MHC (HLA) class II restricted T(H) response) can be used. Alternatively, the target cells may be radiolabeled with $^{51}Cr$ and such, and cytotoxic activity of CTLs may be calculated from radioactivity released from the target cells. Alternatively, it may be examined by measuring IFN-gamma produced and released by CTLs in the presence of cells that carry immobilized peptides, and visualizing the inhibition zone on the media using anti-IFN-gamma monoclonal antibodies.

As a result of examining the CTL inducibility of the peptides as described above, it was discovered that nonapeptides and decapeptides selected from among those peptides having the amino acid sequence indicated by SEQ ID NOs: 5, 14, 64, 73, 77, 79, 97, 103 and 120 showed CTL inducibility as well as high binding affinity to an HLA antigen. Thus, these peptides are exemplified as preferred embodiments of the present invention.

Furthermore, homology analysis results demonstrated that such peptides do not share significant homology with peptides derived from any other known human gene products. This lowers the possibility of unknown or undesired immune responses when used for immunotherapy. Therefore, also from this aspect, these peptides are useful for eliciting immunity against MPHOSPH1 in cancer patients. Thus, peptides having an amino acid sequence selected from among SEQ ID NOs: 5, 14, 64, 73, 77, 79, 97, 103 and 120, are encompassed by the present invention.

In addition to modification as discussed above, the peptides of the present invention may be linked to other peptides, so long as the resulting linked peptide retains the CTL inducibility of the original peptide. Examples of suitable "other" peptides include: the peptides of the present invention or the CTL inducible peptides derived from other TAAs. The peptide of the present invention can be linked to a "other" peptide directly or indirectly via a linker. The linkers between the peptides are well known in the art, for example, AAY (P. M. Daftarian et al., J Trans Med 2007, 5:26), AAA, NKRK (R. P. M. Sutmuller et al., J Immunol. 2000, 165: 7308-7315) or K (S. Ota et al., Can Res. 62, 1471-1476, K. S. Kawamura et al., J Immunol. 2002, 168: 5709-5715).

For example, peptides derived from non-MPHOSPH1 tumor-associated antigens also can be used to increase immune response via HLA class I and/or class II. It is well-known in the art that cancer cells express more than one tumor associated gene. Some CTL inducible peptides derived from such TAAs have been isolated (for example, WO2008/047473, WO2010/047062, WO2008/102557, WO2009/025116). Accordingly, examples of "other" peptides that is linked to the peptide of the present invention include, but are not limited to, CTL inducible peptides derived from TAAs other than MHPOSPH1. In the present invention, "other" peptides may not be only MHC Class I restricted peptides but also MHC Class II restricted peptide. One of ordinary skill in the art can prepare polypeptides including one or more MPHOSPH1 peptides and one or more of the non-MPHOSPH1 peptides, or nucleic acids encoding such polypeptides, using conventional molecular biology procedures.

The above-described linked peptides are referred to herein as "polytopes", i.e., groups of two or more potentially immunogenic or immune response stimulating peptides that can be joined together in various arrangements (e.g., concatenated, overlapping). The polytope (or nucleic acid encoding the polytope) can be administered in accordance with standard immunization protocols, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci. USA 92(13):5845-5849, 1995; Gilbert et al., Nature Biotechnol. 15(12):1280-1284, 1997; Thomson et al., J Immunol. 157(2):822-826, 1996; Tarn et al., J Exp. Med. 171(1):299-306, 1990). Polytopes containing various numbers and combinations of epitopes can be prepared and tested for recognition by CTLs and for efficacy in increasing an immune response.

The peptides of the present invention may be further linked to other substances, so long as they retain the CTL inducibility. Illustrative examples of such "other" substances include, but are not limited to, peptides, lipids, sugar and sugar chains, acetyl groups, natural and synthetic polymers, etc. The peptides may contain modifications such as glycosylation, side chain oxidation, or phosphorylation, so long as the modifications do not destroy the biological activity of the peptides as described herein. These kinds of modifications may be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept may also be adopted for the present polypeptides. The stability of a polypeptide may be assayed in a number of ways. For instance, peptidases and various biological media, such as human plasma and serum, can be used to test stability (see, e.g., Verhoef et al., Eur J Drug Metab Pharmacokin 1986, 11: 291-302).

When the peptides of the present invention include a cysteine residue, the peptides tend to form dimers via a disulfide bond between SH groups of the cysteine residues. Therefore, dimers of the peptides of the present invention are also included in the peptides of the present invention.

Moreover, as noted above, among the modified peptides that are substituted, deleted, inserted and/or added by one, two or several amino acid residues, those having same or higher activity as compared to original peptides can be screened for or selected. The present invention, therefore, also provides the method of screening for or selecting modified peptides having same or higher activity as compared to originals. For example, the method may include steps of:

a: modifying (i.e., substituting, deleting, inserting or adding) at least one amino acid residue of a peptide of the present invention, b: determining the activity of the peptide modified in step (a), and c: selecting the peptide having same or higher activity as compared to the original peptide.

Herein, the activity may include MHC binding activity and APC or CTL inducibility. Preferably, the activity of the peptide is CTL inducibility.

III. PREPARATION OF MPHOSPH1 PEPTIDES

The peptides of the present invention may be prepared using well known techniques. For example, the peptides of the present invention may be prepared synthetically, by recombinant DNA technology or chemical synthesis. The peptides of the present invention may be synthesized individually or as longer polypeptides including two or more peptides. The peptides may be isolated, i.e., purified or isolated substantially free from other naturally occurring host cell proteins and fragments thereof, or any other chemical substances.

The peptides of the present invention may contain modifications, such as glycosylation, side chain oxidation, or phosphorylation, provided such modifications do not destroy the biological activity of the original peptides. Other illustrative modifications include incorporation of D-amino acids or other amino acid mimetics that may be used, for example, to increase the serum half-life of the peptides.

A peptide of the present invention may be obtained through chemical synthesis based on the selected amino acid sequence. For example, conventional peptide synthesis methods that may be adopted for the synthesis include:

(i) Peptide Synthesis, Interscience, New York, 1966;

(ii) The Proteins, Vol. 2, Academic Press, New York, 1976;

(iii) Peptide Synthesis (in Japanese), Maruzen Co., 1975;

(iv) Basics and Experiment of Peptide Synthesis (in Japanese), Maruzen Co., 1985;

(v) Development of Pharmaceuticals (second volume) (in Japanese), Vol. 14 (peptide synthesis), Hirokawa, 1991;

(vi) WO99/67288; and (vii) Barany G. & Merrifield R. B., Peptides Vol. 2, "Solid Phase Peptide Synthesis", Academic Press, New York, 1980, 100-118.

Alternatively, the peptides of the present invention may be obtained adopting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. Such vectors and host cells are also provided by the present invention. The host cell is then cultured to produce the peptide of interest. The peptide may also be produced in vitro adopting an in vitro translation system.

IV. POLYNUCLEOTIDES

The present invention provides polynucleotides that encode any of the afore-mentioned peptides of the present invention. The polynucleotides of the present invention may include polynucleotides derived from the natural occurring MPHOSPH1 gene (for example, GenBank Accession No. NM_001031702 (SEQ ID NO: 125)) or those having a conservatively modified nucleotide sequences thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon may be altered to any of the corresponding codons described without altering the encoded polypeptide. Such nucleic acid variations, referred to in the art as "silent variations," represent one species of conservatively modified variant. Every nucleic acid sequence described herein as encoding a peptide also describes every possible silent variation of the nucleic acid. One of skill in the art will readily recognize that each codon in a nucleic acid (except AUG, which is ordinarily the only codon for methionine, and TGG, which is ordinarily the only codon for tryptophan) may be modified to yield a functionally identical molecule. Accordingly, each disclosed peptide-encoding nucleotide sequence represents an implicit disclosure of the silent variations associated therewith.

The polynucleotide of the present invention may be composed of DNA, RNA, and derivatives thereof. As is well known in the art, a DNA molecule is suitably composed of bases such as the naturally occurring bases A, T, C, and G, and T is replaced by U in an RNA. One of skill in the art will recognize that non-naturally occurring bases be included in polynucleotides, as well.

The polynucleotide of the present invention may encode multiple peptides of the present invention with or without intervening amino acid sequences. For example, the intervening amino acid sequence may provide a cleavage site (e.g., enzyme recognition sequence) of the polynucleotide or the translated peptides. Furthermore, the polynucleotide of the present invention may include any additional sequences to the coding sequence encoding the peptide of the present invention. For example, the polynucleotide of the present invention may be a recombinant polynucleotide that includes regulatory sequences required for the expression of the peptide or may be an expression vector (plasmid) with marker genes and such. In general, such recombinant polynucleotides may be prepared by the manipulation of polynucleotides through conventional recombinant techniques using, for example, polymerases and endonucleases.

Both recombinant and chemical synthesis techniques may be used to produce the polynucleotides of the present invention. For example, the polynucleotide of the present invention may be produced by insertion of the polynucleotide having the coding sequence of the peptide of the present invention into an appropriate vector, which may be expressed when transfected into a competent cell. Alternatively, the polynucleotide of the present invention may be amplified using PCR techniques or replicated in a suitable host (see, e.g., Sambrook et al., Molecular Cloning: A Laboratory Manual, Cold Spring Harbor Laboratory, New York, 1989). Alternatively, the polynucleotide of the present invention may be synthesized using the solid phase techniques, as described in Beaucage S L & Iyer R P, Tetrahedron 1992, 48: 2223-311; Matthes et al., EMBO J 1984, 3: 801-5.

V. EXOSOMES

The present invention further provides intracellular vesicles called exosomes, which present complexes formed between the peptides of the present invention and HLA antigens on their surface. Exosomes may be prepared, for example by using the methods detailed in Japanese Patent Application Kohyo Publications No. Hei 11-510507 and WO99/03499, and may be prepared using APCs obtained from patients who are subject to treatment and/or prevention. The exosomes of the present invention may be inoculated as vaccines, similarly to the peptides of the present invention.

The type of HLA antigens included in the complexes must match that of the subject requiring treatment and/or prevention. For example, for Japanese, HLA-A2, particularly HLA-A*0201 and HLA-A*0206 are often appropriate. The use of HLA-A2 type that is highly expressed among the Japanese and Caucasian is favorable for obtaining effective results, and subtypes such as HLA-A*0201 and HLA-A*0206 find use. Typically, in the clinic, the type of HLA antigen of the patient requiring treatment is investigated in advance, which enables appropriate selection of peptides having high levels of binding affinity to this antigen, or having CTL inducibility by antigen presentation. Furthermore, in order to obtain peptides showing high binding affinity and CTL inducibility, substitution, deletion, or addition of 1, 2, or several amino acids may be performed based on the amino acid sequence of the naturally occurring MPHOSPH1 partial peptide.

When using the HLA-A2 type HLA antigen for the exosomes of the present invention, the peptides having an amino acid sequence of any one of SEQ ID NOs: 5, 14, 64, 73, 77, 79, 97, 103 and 120 have particular utility. In some embodiments, the exosomes of the present invention are exosomes that present a complex of the peptide of the present invention and HLA-A2 antigen on their surface. Typical examples of the HLA-A2 antigen contained in such complexes include, but are not limited to, HLA-A*0201 and HLA-A*0206.

VI. ANTIGEN-PRESENTING CELLS (APCS)

The present invention also provides isolated APCs that present complexes formed with HLA antigens and the peptides of the present invention on their surface. The APCs may be derived from patients who are subject to treatment and/or prevention, and may be administered as vaccines by themselves or in combination with other drugs including the peptides, exosomes, or CTLs of the present invention.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DCs are representative APCs having the strongest CTL inducing activity among APCs, DCs are suitable for the APCs of the present invention.

For example, the APCs of the present invention may be obtained by inducing DCs from peripheral blood monocytes and then contacting (stimulating) them with the peptides of the present invention in vitro, ex vivo or in vivo. When the peptides of the present invention are administered to a subject, APCs that present the peptides of the present invention are induced in the body of the subject. Therefore, the APCs of the present invention may be obtained by collecting the APCs from the subject after administering the peptides of the present invention to the subject. Alternatively, the APCs of the present invention may be obtained by contacting APCs collected from a subject with the peptide of the present invention.

The APCs of the present invention may be administered to a subject for inducing immune response against cancer in the subject by themselves or in combination with other drugs including the peptides, exosomes or CTLs of the present invention. For example, the ex vivo administration may include steps of:

a: collecting APCs from a first subject, b: contacting the APCs of step a, with the peptide of the present invention, and c: administering the APCs of step b to a second subject.

The first subject and the second subject may be the same individual, or may be different individuals. The APCs obtained by step b may be administered as a vaccine for treating and/or preventing cancer, examples of which include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

The present invention also provides a method or process for manufacturing a pharmaceutical composition for inducing APCs, wherein the method includes the step of admixing or formulating the peptide of the present invention with a pharmaceutically acceptable carrier.

According to an aspect of the present invention, the APCs of the present invention have CTL inducibility. In the context of the APCs, the phrase "having CTL inducibility" refers to showing higher CTL inducibility than those of APCs contacted with no peptides. Such APCs having CTL inducibility may be prepared by a method which includes the step of transferring a polynucleotide encoding the peptide of the present invention to APCs in vitro as well as the method mentioned above. The introduced genes may be in the form of DNA or RNA. Examples of methods for introduction include, without particular limitations, various methods conventionally performed in this field, such as lipofection, electroporation, or calcium phosphate method may be used. More specifically, it may be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present partial peptides.

In some embodiments, the APCs of the present invention are APCs that present complexes of HLA-A2 antigen and the peptide of the present invention on their surface. Typical examples of the HLA-A2 antigen contained in such complexes include, but are not limited to, HLA-A*0201 and HLA-A*0206.

VII. CYTOTOXIC T LYMPHOCYTES (CTLS)

A CTL induced against any of the peptides of the present invention strengthens the immune response targeting cancer cells in vivo and thus may be used as vaccines similar to the peptides. Thus, the present invention provides isolated CTLs that are specifically induced or activated by any of the present peptides of the present invention.

Such CTLs may be obtained by (1) administering the peptide(s) of the present invention to a subject, (2) contacting (stimulating) subject-derived APCs, and CD8 positive T cells, or peripheral blood mononuclear leukocytes in vitro with the peptide(s) of the present invention, (3) contacting CD8 positive T cells or peripheral blood mononuclear leukocytes in vitro with the APCs or exosomes presenting a complex of an HLA antigen and the peptide on their surface or (4) introducing a polynucleotide encoding both of T cell receptor (TCR) subunits or polynucleotides encoding each of TCR subunits, wherein the TCR can bind a complex of the peptide of the present invention and HLA-A2 antigen on a cell surface. Such APCs or exosomes to be used in preparation of CTLs may be prepared by the methods described above. Details of the method of (4) is described bellow in section "VIII. T Cell Receptor (TCR)".

The CTLs of the present invention may be derived from patients who are subject to treatment and/or prevention, and may be administered by themselves or in combination with other drugs including the peptides, APCs or exosomes of the present invention for the purpose of regulating effects. The obtained CTLs act specifically against target cells presenting the peptides of the present invention, for example, the same peptides used for induction. The target cells may be cells that endogenously express MPHOSPH1, such as cancer cells, or cells that are transfected with the MPHOSPH1 gene; and cells that present a peptide of the present invention on the cell surface due to stimulation by the peptide may also serve as targets of activated CTL attack.

In some embodiments, the CTLs of the present invention recognize cells presenting complexes of HLA-A2 antigen and the peptide of the present invention. In the context of the CTL, the phrase "recognize a cell" refers to binding a complex of HLA-A2 antigen and the peptide of the present invention on the cell surface via its TCR and showing specific cytotoxic activity against the cell. Herein, "specific cytotoxic activity" refers to showing cytotoxic activity against the cell presenting a complex of HLA-A2 antigen and the peptide of the present invention but not other cells. Typical examples of the HLA-A2 antigen contained in such complex include, but are not limited to, HLA-A*0201 and HLA-A*0206.

VIII. T CELL RECEPTOR (TCR)

The present invention also provides for compositions that include a polynucleotide encoding both of TCR subunits or polynucleotides encoding each of TCR subunits, wherein the TCR can bind to a complex of HLA-A2 antigen and the peptide of the present invention on a cell surface, and methods of using the same. Such TCR subunits have the ability to form TCRs that confer specificity to T cells against tumor cells expressing MPHOSPH1. By using the known methods in the art, the polynucleotides encoding each of alpha- and beta-chains of the TCR of the CTL induced with the peptide of the present invention can be identified (WO2007/032255 and Morgan et al., J Immunol, 171, 3288 (2003)). For example, the PCR method can be preferably used. The PCR primers for the analysis can be, for example, 5'-R primer (5'-gtctaccaggcattcgcttcat-3') (SEQ ID NO: 127) as a 5' side primer and 3-TRa-C primer (5'-tcagctggaccaca-gccgcagcgt-3') (SEQ ID NO: 128) specific to TCR alpha-chain C region, 3-TRb-C1 primer (5'-tcagaaatcctttctcttgac-3') (SEQ ID NO: 129) specific to TCR beta-chain C1 region or 3-TRbeta-C2 primer (5'-ctagcctctggaatccttctctt-3') (SEQ ID NO: 130) specific to TCR beta-chain C2 region as 3' side primers, but not limited thereto. The derivative TCRs can bind target cells presenting the peptide of the present invention with high avidity, and optionally mediate efficient killing of target cells presenting the peptide of the present invention in vivo and in vitro.

The polynucleotide encoding both of the TCR subunits or polynucleotides encoding each of the TCR subunits may be incorporated into suitable vectors, e.g., retroviral vectors. These vectors are well known in the art. The polynucleotides or the vectors including them usefully may be transferred into a T cell (e.g., CD8 positive T cell), for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

Specific TCRs against the peptides of the present invention should be capable of specifically recognizing a complex of the peptide of the present invention and HLA antigen, giving a T cell specific activity against a target cell presenting a complex of the peptide of the present invention and HLA antigen when the TCR is presented on the surface of the T cell. The requisite activity can be confirmed by any known methods that CTLs prepared by introducing the polypeptide(s) encoding such TCR subunits can be specifically recognize such target cells. Preferred examples of such methods include, for example, HLA multimer staining analysis using HLA molecules and the peptides of the present invention, and ELISPOT assay. By performing the ELISPOT assay, it can be confirmed that CTLs prepared by the above methods can specifically recognize the target cells, and that signals generated by such recognition can be transmitted intracellularly. Furthermore, it can be also confirmed by known methods that CTLs prepared by the above methods have specific cytotoxic activity against the target cells. Examples of such methods include, for example, Cr release assay using cells expressing both of HLA-A2 antigen and MPHOSPH1.

In one aspect, the present invention provides CTLs which are prepared by transduction with the polynucleotide encoding both of the TCR subunits or polynucleotides encoding each of the TCR subunits, wherein the TCR can bind to a complex of the peptide having an amino acid sequence selected from the group consisting of SEQ ID NOs: 5, 14, 64, 73, 77, 79, 97, 103 and 120 and HLA-A2 antigen on a cell surface.

The transduced CTLs are capable of homing to cancer cells in vivo, and may be expanded by well known culturing methods in vitro (e.g., Kawakami et al., J Immunol., 142, 3452-3461 (1989)). The CTLs of the present invention may be used to form an immunogenic composition useful in either or both of the treatment and the prevention of cancer in a patient in need of therapy or protection (WO2006/031221).

IX. PHARMACEUTICAL COMPOSITIONS

Since MPHOSPH1 expression is specifically elevated in cancer, examples of which include, but are not necessarily limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor, as compared with normal tissues, the peptides or polynucleotides of the present invention may be used for either or both of the treatment and the prophylaxis of cancer. Thus, the present invention provides a pharmaceutical agent or composition formulated for either or both of the treatment and prophylaxis of cancer, such agent or composition including one or more peptides, or polynucleotides of the present invention as active ingredients. Alternatively, any of the foregoing exosomes or APCs that present a complex of the peptide of the present invention and HLA antigen may be used as active ingredients for pharmaceutical agents or compositions. In addition, the afore-mentioned CTLs that can recognize a cell presenting a complex of the peptide of the present invention and HLA antigen may also be used as active ingredients for pharmaceutical agents or compositions of the present invention.

Accordingly, the present invention provides agents or compositions that include at least one active ingredient selected from among:
(a) one or more peptides of the present invention;
(b) one or more polynucleotides encoding such a peptide as disclosed herein in an expressible form;
(c) one or more APCs or exosomes of the present invention; and
(d) one or more CTLs of the present invention.

The pharmaceutical agents or compositions of the present invention find use as a vaccine. In the context of the present invention, the phrase "vaccine" (also referred to as an immunogenic composition) refers to a composition that has the function to improve, enhance and/or induce anti-tumor immunity upon inoculation into animals. In other words, the present invention provides the pharmaceutical agents or compositions of the present invention for inducing an immune response against cancer in a subject.

The pharmaceutical agents or compositions of the present invention can be used for either or both of the treatment and the prevention of cancer in a subject. Examples of such subjects to which the pharmaceutical agents or compositions may be applied include humans, as well as other mammal including, but not limited to, mouse, rat, guinea-pig, rabbit, cat, dog, sheep, goat, pig, cattle, horse, monkey, baboon, and chimpanzee, particularly a commercially important animal or a domesticated animal. In some embodiments, the pharmaceutical agents or compositions of the present invention can be formulated for the administration to a subject whose HLA antigen is HLA-A2.

In another embodiment, the present invention also provides the use of an active ingredient in the manufacture of a pharmaceutical agent or composition formulated for either or both of the treatment and the prevention of cancer or tumor, including the post-operative recurrence thereof, such active ingredient selected from among:
(a) a peptide of the present invention;
(b) a polynucleotide encoding such a peptide as disclosed herein in an expressible form;
(c) an APC or an exosome presenting a peptide of the present invention on its surface; and
(d) a cytotoxic T cell of the present invention.

Alternatively, the present invention further provides an active ingredient for use in either or both of the treatment and prevention of a cancer or tumor, such active ingredient selected from among:
(a) a peptide of the present invention;
(b) a polynucleotide encoding such a peptide as disclosed herein in an expressible form;
(c) an APC or an exosome presenting a peptide of the present invention on its surface; and
(d) a cytotoxic T cell of the present invention.

Alternatively, the present invention further provides a method or process for manufacturing a pharmaceutical composition or agent for either or both of the treatment and prevention of a cancer or tumor, wherein the method or process includes the step of formulating a pharmaceutically or physiologically acceptable carrier with an active ingredient selected from among:
(a) a peptide of the present invention;
(b) a polynucleotide encoding such a peptide as disclosed herein in an expressible form;
(c) an APC or an exosome of the present invention; and
(d) a cytotoxic T cell of the present invention.

In another embodiment, the present invention also provides a method or process for manufacturing a pharmaceutical composition or agent for either or both of the treatment and prevention of a cancer or tumor, wherein the method or process includes the steps of admixing an active ingredient with a pharmaceutically or physiologically acceptable carrier, wherein the active ingredient is selected from among:
(a) a peptide of the present invention;
(b) a polynucleotide encoding such a peptide as disclosed herein in an expressible form;
(c) an APC or an exosome of the present invention; and
(d) a cytotoxic T cell of the present invention.

In another embodiment, the present invention also provides the method for either or both of the treatment and prevention of cancer or tumor, wherein the method comprises the step of administering to a subject at least one active ingredient selected from among:
(a) a peptide of the present invention;
(b) a polynucleotide encoding such a peptide as disclosed herein in an expressible form;
(c) an APC or an exosome of the present invention; and
(d) a cytotoxic T cell of the present invention.

According to the present invention, peptides having an amino acid sequence selected from among SEQ ID NOs: 5, 14, 64, 73, 77, 79, 97, 103 and 120 have been found to be HLA-A2 restricted epitope peptides and thus serve as candidates that may induce specific immune response against cancer expressing HLA-A2 and MPHOSPH1 in a subject. Therefore, the pharmaceutical agents or compositions of the present invention that include any of these peptides, with the amino acid sequence of SEQ ID NOs: 5, 14, 64, 73, 77, 79, 97, 103 or 120, are particularly suited for the administration to subjects whose HLA antigen is HLA-A2. Particularly preferred example of these peptides is the peptide having an amino acid sequence of SEQ ID NO: 120 that was confirmed to have the ability to induce CTLs targeting cancer cells expressing HLA-A2 antigen and MPHOSPH1. Accordingly, in preferred embodiments, the pharmaceutical agents or compositions of the present invention will include the peptide having an amino acid sequence of SEQ ID NO: 120 or a modified version thereof, or include a polynucleotide encoding such peptide. The same applies to pharmaceutical agents or compositions that include polynucleotides encoding any of these peptides (i.e., the polynucleotides of the present invention).

Cancers to be treated by the pharmaceutical agents or compositions of the present invention include any cancer in which MPHOSPH1 is expressed (e.g., is overexpressed), examples of which include, but not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

The pharmaceutical agents or compositions of the present invention may contain in addition to the aforementioned active ingredients, such as other peptides that have the ability to induce CTLs against cancerous cells, other polynucleotides encoding the other peptides, other cells that present the other peptides, and the like. Examples of such "other" peptides having the ability to induce CTLs against cancerous cells include, but are not limited to, cancer specific antigens (e.g., identified TAAs).

If necessary, the pharmaceutical agents or compositions of the present invention may optionally include other therapeutic substances as an additional active ingredient, so long as the substance does not inhibit the antitumoral effect of the active ingredient of the present invention (i.e., the peptide, polynucleotide, exosome, APC, CTL of the present invention). For example, formulations may include anti-inflammatory substances, pain killers, chemotherapeutics, and the like. In addition to other therapeutic substances in the medicament itself, the medicaments of the present invention may also be administered sequentially or concurrently with the one or more other pharmacologic agents or compositions. The amounts of medicament and pharmacologic agent or composition depend, for example, on what type of pharmacologic agent(s) or composition(s) is/are used, the disease being treated, and the scheduling and routes of administration.

Those of skill in the art will readily recognize that, in addition to the ingredients particularly mentioned herein, the pharmaceutical agents or compositions of the present invention may include other substances conventional in the art having regard to the type of formulation in question (e.g., fillers, binders, diluents, excipients, etc.).

In one embodiment of the present invention, the pharmaceutical agents or compositions of the present invention may be packaged in articles of manufacture, e.g., as kits containing materials useful for treating the pathological conditions of the disease to be treated, e.g., cancer. The article of manufacture may include a container of any of the present pharmaceutical agents or compositions with a label. Suitable containers include bottles, vials, and test tubes. The containers may be formed from a variety of materials, such as glass or plastic. The label on the container should indicate the agent or composition is used for treatment or prevention of one or more conditions of the disease. The label may also indicate directions for administration and so on.

In addition to the container described above, a kit including a pharmaceutical agent or composition of the present invention may optionally further include a second container housing a pharmaceutically-acceptable diluent. It may further include other materials desirable from a commercial and user standpoint, including other buffers, diluents, filters, needles, syringes, and package inserts with instructions for use.

The pharmaceutical agents or compositions of the present invention can, if desired, be packaged in a pack or dispenser device that can contain one or more unit dosage forms containing the active ingredient. The pack can, for example, include metal or plastic foil, such as a blister pack. The pack or dispenser device can be accompanied by instructions for administration.

(1) Pharmaceutical Compositions Containing the Peptides as the Active Ingredient:

The peptides of the present invention can be administered directly as a pharmaceutical agents or composition, or if necessary, that may be formulated by conventional formulation methods. In the latter case, in addition to the peptides of the present invention, carriers, excipients, and such that are ordinarily used for drugs can be included as appropriate without particular limitations. Examples of such carriers include, but are not limited to, sterilized water, physiological saline, phosphate buffer, culture fluid and such. Furthermore, the pharmaceutical substances, agents or compositions can contain as necessary, stabilizers, suspensions, preservatives, surfactants and such. The pharmaceutical agents or compositions of the present invention can be used for anticancer purposes.

The peptides of the present invention can be prepared in combination, which includes two or more of peptides of the present invention, to induce CTL in vivo. The peptides can be in a cocktail or can be conjugated to each other using standard techniques. For example, the peptides can be chemically linked or expressed as a single fusion polypeptide sequence that may have one or several amino acid(s) as a linker (e.g., Lysine linker: K. S. Kawamura et al. J. Immunol. 2002, 168: 5709-5715). The peptides in the combination can be the same or different. By administering the peptides of the present invention, the peptides are presented in high density by the HLA antigens on APCs, then CTLs that specifically react toward the complex formed between the displayed peptide and the HLA antigen are induced. Alternatively, APCs (e.g., DCs) may be removed from a subject and then stimulated by the peptides of the present invention to obtain APCs that present any of the peptides of the present invention on their cell surface. These APCs can be re-administered to the subject to induce CTLs in the subjects, and as a result, aggressiveness towards the tumor-associated endothelium can be increased.

The pharmaceutical agents or compositions of the present invention, that include any of the peptides of the present invention as active ingredients, can also include an adjuvant so that cellular immunity will be established effectively. Alternatively, the pharmaceutical agent or composition of the present invention can be administered with other active ingredients or can be administered by formulation into granules. An adjuvant refers to any compound, substance or composition that enhances the immune response against the protein when administered together (or successively) with the protein having immunological activity. An adjuvant that can be applied includes those described in the literature (Clin Microbiol Rev 1994, 7: 277-89). Exemplary adjuvants include aluminum phosphate, aluminum hydroxide, alum, cholera toxin, *salmonella* toxin, Incomplete Freund's adjuvant (IFA), Complete Freund's adjuvant (CFA), IS-COMatrix, GM-CSF, CpG, O/W emulsion, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an amine, salts with an organic acid (acetic acid, formic acid, propionic acid, fumaric acid, maleic acid, succinic acid, tartaric acid, citric acid, malic acid, oxalic acid, benzoic acid, methanesulfonic acid and so on) and salts with an inorganic acid (hydrochloric acid, phosphoric acid, hydrobromic acid, sulfuric acid and so on). As used herein, the phrase "pharmaceutically acceptable salt" refers to those salts that retain the biological effectiveness and properties of the compound and that are obtained by reaction with inorganic or organic acids or bases.

In some embodiments, the pharmaceutical agents or compositions of the present invention include a component which primes CTL. Lipids have been identified as substances capable of priming CTL in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

Examples of suitable methods of administration include, but are not necessarily limited to, oral, intradermal, subcutaneous, intramuscular, intraosseous, peritoneal, and intravenous injection, or such, and systemic administration or local administration to the vicinity of the targeted sites (i.e., direct injection). The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1,000 mg, for example, 0.01 mg to 100 mg, for example, 0.1 mg to 10 mg, and can be administered once in a few days to few months. One skilled in the art readily determine suitable and optimal dosages.

(2) Pharmaceutical Compositions Containing Polynucleotides as Active Ingredient:

The pharmaceutical agents or compositions of the present invention can also include polynucleotides encoding the peptide(s) disclosed herein in an expressible form. Herein, the phrase "in an expressible form" means that the polynucleotide, when introduced into a cell, will be expressed in vivo as a polypeptide that induces anti-tumor immunity. In an illustrative embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors. See also, e.g., Wolff et al., Science 1990, 247: 1465-8; U.S. Pat. Nos. 5,580,859; 5,589,466; 5,804,566; 5,739,118; 5,736,524; 5,679,647; and WO 98/04720). Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology that are applicable to the present invention are described by Ausubel et al., in Current Protocols in Molecular Biology, John Wiley & Sons, NY, 1993; and by Krieger, in Gene Transfer and Expression, A Laboratory Manual, Stockton Press, NY, 1990.

Like administration of peptides, administration of polynucleotides may be performed by oral, intradermal, subcutaneous, intravenous, intramuscular, intraosseous, and/or peritoneal injection, or such, and via systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, and can be administered once every a few days to once every few months. One skilled in the art can appropriately select the suitable dose.

X. METHODS USING PEPTIDES, EXOSOMES, APCS AND CTLS

The peptides and polynucleotides of the present invention can be used for preparing or inducing APCs and CTLs. The exosomes and APCs of the present invention can be also used for inducing CTLs. The peptides, polynucleotides, exosomes and APCs can be used in combination with any other compounds so long as the additional compounds do not inhibit CTL inducibility. Thus, any of the aforementioned pharmaceutical agents or compositions of the present invention can be used for inducing CTLs. In addition thereto, those including the peptides and polynucleotides can be also used for inducing APCs as explained below.

(1) Methods of Inducing Antigen-Presenting Cells (APCs):

The present invention provides methods of inducing APCs with CTL inducibility using the peptides or polynucleotides of the present invention.

The methods of the present invention include the step of contacting APCs with the peptides of the present invention in vitro, ex vivo or in vivo. For example, the method including the step of contacting APCs with the peptides of the present invention ex vivo can include steps of:

a: collecting APCs from a subject, and b: contacting the APCs of step a with the peptide of the present invention.

The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any one of peptide of the present invention can be used by itself or in combination with other peptides of the present invention or CTL inducible peptides derived from TAAs other than MPHOSPH1.

On the other hand, when the peptides of the present invention are administered to a subject, the APCs are contacted with the peptides in vivo, and consequently, the APCs with CTL inducibility are induced in the body of the subject. Thus, the method of the present invention includes administering the peptides of the present invention to a subject to induce APCs with CTL inducibility in the body of the subject. Similarly, when the polynucleotides of the present invention are administered to a subject in an expressible form, the peptides of the present invention are expressed and contacted with APCs in vivo, and consequently, APCs with CTL inducibility are induced in the body of the subject. Thus, the method of the present invention may also include administering the polynucleotides of the present invention to a subject to induce APCs with CTL inducibility in the body of the subject. The phrase "expressible form" is described above in section "IX. Pharmaceutical Compositions, (2) Pharmaceutical compositions containing polynucleotides as the active ingredient".

Furthermore, the method of the present invention may include introducing the polynucleotide of the present invention into an APCs to induce APCs with CTL inducibility. For example, the method can include steps of:

a: collecting APCs from a subject, and b: introducing a polynucleotide encoding the peptide of the present invention into an APC.

Step b can be performed as described above in section "VI. Antigen-presenting cells".

Alternatively, the present invention provides a method for preparing an antigen-presenting cell (APC) which specifically induces CTL activity against MPHOSPH1, wherein the method can include one of the following steps:

(a) contacting an APC with a peptide of the present invention in vitro, ex vivo or in vivo; and (b) introducing a polynucleotide encoding a peptide of the present invention into an APC.

Alternatively, the present invention provides methods for inducing an APC having CTL inducibility, wherein the methods include the step selected from among:

(a) contacting an APC with the peptide of the present invention;

(b) introducing the polynucleotide encoding the peptide of the present invention into an APC.

The methods of the present invention can be carried out in vitro, ex vivo or in vivo. Preferably, the methods of the present invention can be carried out in vitro or ex vivo. APCs used for induction of APCs having CTL inducibility can be preferably APCs expressing HLA-A2 antigen. Such APCs can be prepared by the methods well-known in the arts from peripheral blood mononuclear cells (PBMCs) obtained from a subject whose HLA antigen is HLA-A2. The APCs induced by the method of the present invention can be APCs that present a complex of the peptide of the present invention and HLA antigen (HLA-A2 antigen) in their surface. When APCs induced by the method of the present invention are administered to a subject in order to induce immune responses against cancer in the subject, the subject is preferably the same one from whom APCs are derived. However, the subject may be a different one from the APC donor so long as the subject has the same HLA type with the APC donor.

In another embodiment, the present invention provide agents or compositions for use in inducing an APC having CTL inducibility, and such agents or compositions include one or more peptides or polynucleotides of the present invention.

In another embodiment, the present invention provides for the use of the peptide of the present invention or the polynucleotide encoding the peptide in the manufacture of an agent or composition formulated for inducing APCs.

Alternatively, the present invention further provides the peptide of the present invention or the polypeptide encoding the peptide for use in inducing an APC having CTL inducibility.

(2) Methods of Inducing CTLs:

The present invention also provides methods for inducing CTLs using the peptides, polynucleotides, exosomes or APCs of the present invention.

The present invention also provides methods for inducing CTLs using a polynucleotide encoding both of TCR subunits or polynucleotides encoding each of TCR subunits, wherein the TCR can recognize (bind to) a complex of the peptide of the present invention and HLA antigen presented on a cell surface. Preferably, the methods for inducing CTLs may include at least one step selected from among:

a) contacting a CD8 positive T cell with an antigen-presenting cell and/or an exosome that presents on its surface a complex of an HLA antigen and a peptide of the preset invention; and b) introducing a polynucleotide encoding both of TCR subunits or polynucleotides encoding each of TCR subunits into a CD8 positive T cell, wherein the TCR can recognize (bind to) a complex of a peptide of the present invention and an HLA antigen presented on a cell surface.

When the peptides, the polynucleotides, APCs, or exosomes of the present invention are administered to a subject, CTLs are induced in the body of the subject, and the immune response targeting the cancer cells expressing MPHOSPH1 is enhanced. Thus, the methods of the present invention can include the step of administering the peptides, the polynucleotides, the APCs or exosomes of the present invention to a subject.

Alternatively, CTLs can be also induced by using them ex vivo or in vitro, and after inducing CTL, the activated CTLs can be returned to the subject. For example, the method can include steps of:

a: collecting APCs from a subject;

b: contacting the APCs of step a, with the peptide; and c: co-culturing the APCs of step b with CD8 positive T cells.

The APCs to be co-cultured with the CD8 positive T cells in above step c can also be prepared by transferring a polynucleotide of the present invention into APCs as described above in section "VI. Antigen-Presenting Cells", though the present invention is not limited thereto, and thus encompasses any APCs that effectively present on their surface a complex of an HLA antigen and a peptide of the present invention.

One may optionally utilize exosomes that presents on its surface a complex of an HLA antigen and the peptide of the present invention instead of the afore-mentioned APCs. Namely, the present invention can include the step of co-culturing exosomes presenting on their surface a complex of an HLA antigen and the peptide of the present invention. Such exosomes can be prepared by the methods described above in section "V. Exosomes".

APCs or exosomes used for induction of CTLs can be preferably APCs or exosomes that present on their surface a complex of the peptide of the present invention and HLA-A2 antigen.

Furthermore, a CTL can be induced by introducing a polynucleotide encoding both of the TCR subunits or polynucleotides encoding each of the TCR subunits into a CD8 positive T cell, wherein the TCR can bind to a complex of the peptide of the present invention and HLA antigen presented on a cell surface. Such transduction can be performed as described above in section "VIII. T Cell Receptor (TCR)".

The methods of the present invention can be carried out in vitro, ex vivo or in vivo. Preferably, the methods of the present invention can be carried out in vitro or ex vivo. CD8 positive T cells used for induction of CTLs can be prepared by well-known methods in the art from PBMCs obtained from a subject. In preferred embodiments, a donor for CD8 positive T cells can be a subject whose HLA antigen is HLA-A2. The CTLs induced by the methods of the present invention can be CTLs that can recognize cells presenting a complex of the peptide of the present invention and an HLA antigen on its surface. When CTLs induced by the method of the present invention are administered to a subject in order to induce immune responses against cancer in the subject, the subject is preferably the same one from whom CD8 positive T cells are derived. However, the subject may be a different one from the CD8 positive T cell donor so long as the subject has the same HLA type with the CD8 positive T cell donor.

In addition, the present invention provides a method or process for manufacturing a pharmaceutical agent or composition for inducing CTLs, wherein the method or process includes the step of admixing or formulating the peptide of the present invention with a pharmaceutically acceptable carrier.

In another embodiment, the present invention provides an agent or composition for inducing CTL, wherein the agent or composition comprises one or more peptide(s), one or more polynucleotide(s), or one or more APCs or exosomes of the present invention.

In another embodiment, the present invention provides the use of the peptide, polynucleotide, or APC or exosome of the present invention in the manufacture of an agent or composition formulated for inducing a CTL.

Alternatively, the present invention further provides the peptide, polynucleotide, or APC or exosome of the present invention for use in inducing a CTL.

(3) Methods of Inducing Immune Response:

Moreover, the present invention provides methods of inducing an immune response against diseases related to MPHOSPH1. Diseases contemplated include cancer, examples of which include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

The methods of the present invention may include the step of administering to a subject agent(s) or composition(s) containing any of the peptides of the present invention or polynucleotides encoding them. The method of the present invention may also contemplate the administration of exosomes or APCs presenting any of the peptides of the present invention. For details, see the item of "IX. Pharmaceutical Compositions", particularly the part describing the use of the pharmaceutical agents and compositions of the present invention as vaccines. In addition, the exosomes and APCs that can be employed for the present methods for inducing immune response are described in detail under the items of "V. Exosomes", "VI. Antigen-Presenting Cells (APCs)", and (1) and (2) of "X. Methods using Peptides, Exosomes, APCs and CTLs", supra.

In preferred embodiments, the subjects treated by the method of the present invention can be subjects whose HLA antigen is HLA-A2.

The present invention also provides a method or process for manufacturing a pharmaceutical agent or composition inducing immune response, wherein the method may include the step of admixing or formulating a polypeptide or polynucleotide of the present invention with a pharmaceutically acceptable carrier.

Alternatively, the method of the present invention may include the step of administrating a vaccine or a pharmaceutical composition of the present invention that contains:

(a) a peptide of the present invention;
(b) a nucleic acid (polynucleotide) encoding such a peptide as disclosed herein in an expressible form;
(c) an APC or an exosome presenting a peptide of the present invention on its surface; or
(d) a CTL of the present invention.

In the context of the present invention, a cancer expressing MPHOSPH1 can be treated with these active ingredients. Examples of such cancer include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor. Accordingly, prior to the administration of the vaccines or pharmaceutical compositions including the active ingredients, it is preferable to confirm whether the expression level of MPHOSPH1 in the cells or tissues to be treated is enhanced compared with normal cells of the same organ. Thus, in one embodiment, the present invention provides a method for treating cancer expressing MPHOSPH1, which method may include the steps of:

i) determining the expression level of MPHOSPH1 in cells or tissue(s) obtained from a subject with the cancer to be treated;
ii) comparing the expression level of MPHOSPH1 with normal control; and
iii) administrating at least one component selected from among steps (a) to (d) described above to a subject with cancer over-expressing MPHOSPH1 compared with normal control.

Alternatively, the present invention also provides a vaccine or pharmaceutical composition that includes at least one component selected from among (a) to (d) described above, for use in administrating to a subject having cancer over-expressing MPHOSPH1. In other words, the present invention further provides a method for identifying a subject to be treated with the MPHOSPH1 polypeptide of the present invention, such method including the step of determining an expression level of MPHOSPH1 in subject-derived cells or tissue(s), wherein an increase of the level compared to a normal control level of the gene indicates that the subject may have cancer which may be treated with the MPHOSPH1 polypeptide of the present invention. The method of identifying a subject to be treated cancer of the present invention are described in more detail below.

Any subject-derived cell or tissue can be used for the determination of MPHOSPH1 expression so long as it includes the objective transcription or translation product of MPHOSPH1. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous.

Further, if necessary, the cell may be purified from the obtained bodily tissues and fluids, and then used as the subjected-derived sample.

A subject to be treated by the present method is preferably a mammal. Illustrative mammals include, but are not limited to, e.g., human, non-human primate, mouse, rat, dog, cat, horse, and cow.

According to the present invention, the expression level of MPHOSPH1 in cells or tissues obtained from a subject may be determined. The expression level can be determined at the transcription (nucleic acid) product level, using methods known in the art. For example, the mRNA of MPHOSPH1 may be quantified using probes by hybridization methods (e.g., Northern hybridization). The detection may be carried out on a chip, an array or as such. The use of an array may be preferable for detecting the expression level of MPHOSPH1. Those skilled in the art can prepare such probes utilizing the sequence information of MPHOSPH1. For example, the cDNA of MPHOSPH1 may be used as the probes. If necessary, the probes may be labeled with a suitable label, such as dyes, fluorescent substances and isotopes, and the expression level of the gene may be detected as the intensity of the hybridized labels.

Furthermore, the transcription product of MPHOSPH1 (e.g., SEQ ID NO: 125) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of MPHOSPH1. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing substances, such as formamide.

A probe or primer of the present invention is typically a substantially purified oligonucleotide. The oligonucleotide typically includes a region of nucleotide sequence that hybridizes under stringent conditions to at least about 2000, 1000, 500, 400, 350, 300, 250, 200, 150, 100, 50, or 25, consecutive sense strand nucleotide sequence of a nucleic acid including a MPHOSPH1, or an anti sense strand nucleotide sequence of a nucleic acid including a MPHOSPH1, or of a naturally occurring mutant of these sequences. In particular, for example, in a preferred embodiment, an oligonucleotide having 5-50 in length can be used as a primer for amplifying the genes, to be detected. More preferably, mRNA or cDNA of a MPHOSPH1 gene can be detected with oligonucleotide probe or primer of a specific size, generally 15-30 b in length. The size may range from at least 10 nucleotides, at least 12 nucleotides, at least 15 nucleotides, at least 20 nucleotides, at least 25 nucleotides, at least 30 nucleotides and the probes and primers may range in size from 5-10 nucleotides, 10-15 nucleotides, 15-20 nucleotides, 20-25 nucleotides and 25-30 nucleotides. In preferred embodiments, length of the oligonucleotide probe or primer can be selected from 15-25. Assay procedures, devices, or reagents for the detection of gene by using such oligonucleotide probe or primer are well known (e.g. oligonucleotide microarray or PCR). In these assays, probes or primers can also include tag or linker sequences. Further, probes or primers can be modified with detectable label or affinity ligand to be captured. Alternatively, in hybridization based detection procedures, a polynucleotide having a few hundreds (e.g., about 100-200) bases to a few kilo (e.g., about 1000-2000) bases in length can also be used for a probe (e.g., northern blotting assay or cDNA microarray analysis).

Alternatively, the translation product may be detected for the diagnosis of the present invention. For example, the quantity of MPHOSPH1 protein (SEQ ID NO: 126) or the immunologically fragment thereof may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the MPHOSPH1 protein. Such antibodies against the peptides of the present invention and the fragments thereof are also provided by the present invention. Methods to prepare these kinds of antibodies for the detection of proteins are well known in the art, and any method may be employed in the present invention to prepare such antibodies and equivalents thereof.

As another method to detect the expression level of MPHOSPH1 gene based on its translation product, the intensity of staining may be measured via immunohistochemical analysis using an antibody against the MPHOSPH1 protein. Namely, in this measurement, strong staining indicates increased presence/level of the protein and, at the same time, high expression level of MPHOSPH1 gene.

The expression level of a target gene, e.g., the MPHOSPH1 gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells using a sample(s) previously collected and stored from a subject(s) whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of MPHOSPH1 gene in samples from subjects whose disease states are known. Furthermore, the control level can be derived from a database of expression patterns from previously tested cells. Moreover, according to an aspect of the present invention, the expression level of MPHOSPH1 gene in a biological sample may be compared to multiple control levels, determined from multiple reference samples. It is preferred to use a control level determined from a reference sample derived from a tissue type similar to that of the subject-derived biological sample. Moreover, it is preferred to use the standard value of the expression levels of MPHOSPH1 gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of MPHOSPH1 gene is increased as compared to the normal control level, or is similar/equivalent to the cancerous control level, the subject may be diagnosed with cancer to be treated.

The present invention also provides a method of (i) diagnosing whether a subject suspected to have cancer to be treated, and/or (ii) selecting a subject for cancer treatment, which method may include the steps of:

a) determining the expression level of MPHOSPH1 in cells or tissue(s) obtained from a subject who is suspected to have the cancer to be treated;

b) comparing the expression level of MPHOSPH1 with a normal control level;

c) diagnosing the subject as having the cancer to be treated, if the expression level of MPHOSPH1 is increased as compared to the normal control level; and d) selecting the subject for cancer treatment, if the subject is diagnosed as having the cancer to be treated, in step c).

Alternatively, such a method may include the steps of:

a) determining the expression level of MPHOSPH1 in cells or tissue(s) obtained from a subject who is suspected to have the cancer to be treated;

b) comparing the expression level of MPHOSPH1 with a cancerous control level;

c) diagnosing the subject as having the cancer to be treated, if the expression level of MPHOSPH1 is similar or equivalent to the cancerous control level; and d) selecting the subject for cancer treatment, if the subject is diagnosed as having the cancer to be treated, in step c).

The present invention also provides a diagnostic kit for diagnosing or determining a subject who is or is suspected to be suffering from or at risk for developing cancer that can be treated with the MPHOSPH1 polypeptide of the present invention, which may also find use in assessing and/or monitoring the efficacy or applicability of a cancer immunotherapy. Preferably, the cancer includes, but is not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor. More particularly, the kit preferably may include at least one reagent for detecting the expression of the MPHOSPH1 gene in a subject-derived cell, which reagent may be selected from the group of:

(a) a reagent for detecting an mRNA of the MPHOSPH1 gene;

(b) a reagent for detecting the MPHOSPH1 protein or the immunologically fragment thereof; and (c) a reagent for detecting the biological activity of the MPHOSPH1 protein.

Examples of reagents suitable for the detection of mRNA of the MPHOSPH1 gene may include nucleic acids that specifically bind to or identify the MPHOSPH1 mRNA, such as oligonucleotides that have a complementary sequence to a portion of the MPHOSPH1 mRNA. These kinds of oligonucleotides are exemplified by primers and probes that are specific to the MPHOSPH1 mRNA. These kinds of oligonucleotides may be prepared based on methods well known in the art. If needed, the reagent for detecting the MPHOSPH1 mRNA may be immobilized on a solid matrix. Moreover, more than one reagent for detecting the MPHOSPH1 mRNA may be included in the kit.

On the other hand, examples of reagents suitable for the detection of the MPHOSPH1 protein or the immunologically fragment thereof may include antibodies to the MPHOSPH1 protein or the immunologically fragment thereof. The antibody may be monoclonal or polyclonal. Furthermore, any fragment or modification (e.g., chimeric antibody, scFv, Fab, $F(ab')_2$, Fv, etc.) of the antibody may be used as the reagent, so long as the fragment or modified antibody retains the binding ability to the MPHOSPH1 protein or the immunologically fragment thereof. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the MPHOSPH1 protein may be included in the kit.

The kit may contain more than one of the aforementioned reagents. The kit can further include a solid matrix and reagent for binding a probe against a MPHOSPH1 gene or antibody against a MPHOSPH1 peptide, a medium and container for culturing cells, positive and negative control reagents, and a secondary antibody for detecting an antibody against a MPHOSPH1 peptide. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers may include bottles, vials, and test tubes. The containers may be formed from a variety of materials, such as glass or plastic.

In an embodiment of the present invention, when the reagent is a probe against the MPHOSPH1 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of MPHOSPH1 mRNA present in the sample. The detection sites may be configured in any suitably detectable shape and are typically in the shape of a bar or dot spanning the width of a test strip.

The kit of the present invention may further include a positive control sample or MPHOSPH1 standard sample. The positive control sample of the present invention may be prepared by collecting MPHOSPH1 positive samples and then assaying their MPHOSPH1 levels. Alternatively, a purified MPHOSPH1 protein or polynucleotide may be added to cells that do not express MPHOSPH1 to form the positive sample or the MPHOSPH1 standard sample. In the context of the present invention, purified MPHOSPH1 may be a recombinant protein. The MPHOSPH1 level of the positive control sample is, for example, more than the cut off value.

In one embodiment, the present invention further provides a diagnostic kit including, a protein or a partial protein thereof specifically recognized by the antibody of the present invention or the fragment thereof.

Examples of partial peptides of the present invention include polypeptides composed of at least 8, preferably 15, and more preferably 20 contiguous amino acids in the amino acid sequence of a protein of the present invention. Cancer can be diagnosed by detecting an antibody in a sample (e.g., blood, tissue) using a protein or a peptide (polypeptide) of the present invention. The method for preparing the protein of the present invention and peptides are as described above.

The methods for diagnosing cancer of the present invention can be performed by determining the difference between the amount of anti-MPHOSPH1 antibody and that in the corresponding control sample as describe above. The subject is suspected to be suffering from cancer, if cells or tissues of the subject contain antibodies against the expression products (MPHOSPH1) of the gene and the quantity of the anti-MPHOSPH1 antibody is determined to be more than the cut off value in level compared to that in normal control.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from the subject suspected to be suffering from cancer.

The present invention further provides methods and diagnostic agents for evaluating immunological response of subject by using peptide epitopes as described herein. In one embodiment of the invention, HLA-A2 restricted peptides as described herein may be used as reagents for evaluating or predicting an immune response of a subject. The immune response to be evaluated may be induced by contacting an immunogen with immunocompetent cells in vitro or in vivo. In certain embodiments, any substances or compositions that may result in the production of antigen specific CTLs that recognize and bind to the peptide epitope(s) may be employed as the reagent. The peptide reagents may need not to be used as the immunogen. Assay systems that are used for such an analysis include relatively recent technical developments such as tetramers, staining for intracellular lymphokines and interferon release assays, or ELISPOT assays. In preferred embodiments, the immunocompetent cells for evaluating an immunological response, may be selected from among peripheral blood, peripheral blood lymphocyte (PBL), and peripheral blood mononuclear cell (PBMC). Methods for collecting or isolating such immunocompetent cells are well known in the arts. In an alternate preferred embodiment, the immunocompetent cells to be contacted with peptide reagent include antigen presenting cells such as dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et al, J. Clin. Invest. 100: 503-513, 1997 and Penna et al., J Exp. Med. 174: 1565-1570, 1991) including peptides of the present invention. For example, patient PBMC samples obtained from individuals with a cancer to be treated can be analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele specific molecules present in the patient are selected for the analysis. The immunogenicity of the vaccine may be indicated by the presence of epitope-specific CTLs in the PBMC sample. The peptides of the invention may also be used to make antibodies, using techniques well known in the art (see, e.g., CURRENT PROTOCOLS IN IMMUNOLOGY, Wiley/Greene, NY; and Antibodies A Laboratory Manual, Harlow and Lane, Cold Spring Harbor Laboratory Press, 1989), which may find use as reagents to diagnose, detect or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein. For instance, the present invention provides a method for diagnosing or detecting a disorder characterized by quantity of a MPHOSPH1 immunogenic polypeptide. These methods involve determining quantity of a MPHOSPH1 peptide, or a complex of a MPHOSPH1 peptide and an HLA class I molecule in a biological sample. The expression of a peptide or complex of peptide and HLA class I molecule can be determined or detected by assaying with a binding partner for the peptide or complex. In an preferred embodiment, a binding partner for the peptide or complex may be an antibody recognizes and specifically bind to the peptide. The expression of MPHOSPH1 in a biological sample, such as a tumor biopsy, can also be tested by standard PCR amplification protocols using MPHOSPH1 primers. An example of tumor expression is presented herein and further disclosure of exemplary conditions and primers for MPHOSPH1 amplification can be found in WO2003/27322, the contents of which are incorporated by reference herein.

Preferably, the diagnostic methods involve contacting a biological sample isolated from a subject with an agent specific for the MPHOSPH1 peptide to detect the presence of the MPHOSPH1 peptide in the biological sample. As used herein, "contacting" means placing the biological sample in sufficient proximity to the agent and under the appropriate conditions of, e.g., concentration, temperature, time, ionic strength, to allow the specific interaction between the agent and MPHOSPH1 peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Optimal conditions for facilitating a specific interaction between a molecule and its cognate are described in U.S. Pat. No. 5,108,921, issued to Low et al., the contents of which are incorporated by reference herein.

The diagnostic method of the present invention can be performed in either or both of in vivo and in vitro. Accordingly, biological sample can be located in vivo or in vitro in the present invention. For example, the biological sample can be a tissue in vivo and the agent specific for the MPHOSPH1 immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor cells collected from a subject to be diagnosed or treated.

Alternatively, the diagnosis can be done, by a method which allows direct quantification of antigen-specific T cells by staining with Fluorescein-labeled HLA multimeric complexes (e.g., Altman, J. D. et al., 1996, Science 274: 94; Altman, J. D. et al., 1993, Proc. Natl. Acad. Sci. USA 90:10330). Staining for intracellular lymphokines, and interferon-gamma release assays or ELISPOT assays also has been provided. Multimer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

Accordingly, in some embodiments, the present invention provides a method for diagnosing or evaluating an immunological response of a subject administered at least one of the MPHOSPH1 peptides of the present invention, the method including the steps of:

(a) contacting an immunogen with immunocompetent cells under the condition suitable for induction of CTL specific to the immunogen;

(b) detecting or determining induction level of the CTL induced in step (a); and (c) correlating the immunological response of the subject with the CTL induction level.

In the context of the present invention, the immunogen preferably includes at least one of (a) a MPHOSPH1 peptide selected from among SEQ ID NOs: 5, 14, 64, 73, 77, 79, 97, 103 and 120 and (b) peptides having such amino acid sequences in which such amino acid sequences have been modified with 1, 2 or more amino acid substitution(s). In the meantime, conditions suitable of induction of immunogen specific CTL are well known in the art. For example, immunocompetent cells may be cultured in vitro under the presence of immunogen(s) to induce immunogen specific CTL. In order to induce immunogen specific CTLs, any stimulating factors may be added to the cell culture. For example, IL-2 is preferable stimulating factors for the CTL induction.

In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol. Alternatively, the step of evaluation or monitoring of immunological response to the cancer therapy may at the completion of the therapy protocol.

According to the present invention, enhanced induction of immunogen specific CTL as compared with a control indicates that the subject to be evaluated or diagnosed immunologically responded to the immunogen(s) that has/have been administered. Suitable controls for evaluating the immunological response may include, for example, a CTL induction level when the immunocompetent cells are contacted with no peptide, or control peptide(s) having amino acid sequences other than any MPHOSPH1 peptides. (e.g. random amino acid sequence). In a preferred embodiment, the immunological response of the subject is evaluated in a sequence specific manner, by comparison with an immunological response between each immunogen administered to the subject. In particular, even when a mixture of some kinds of MPHOSPH1 peptides is administered to the subject, immunological response might vary depending on the peptides. In that case, by comparison of the immunological response between each peptide, peptides to which the subject show higher response can be identified.

XI. ANTIBODIES

The present invention further provides antibodies that bind to peptides of the present invention. Preferred antibodies specifically bind to a peptide of the present invention and will not bind (or will bind weakly) to other peptide. Alternatively, antibodies may bind to peptides of the invention as well as the homologs thereof. Antibodies against peptides of the invention can find use in cancer diagnostic and prognostic assays, as well as imaging methodologies. Similarly, such antibodies can find use in the treatment, diagnosis, and/or prognosis of other cancers, to the extent MPHOSPH1 is also expressed or over-expressed in a cancer patient. Moreover, intracellularly expressed antibodies (e.g., single chain antibodies) may therapeutically find use in treating cancers in which the expression of MPHOSPH1 is involved, examples of which include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

The present invention also provides various immunological assays for the detection and/or quantification of an MPHOSPH1 protein (SEQ ID NO: 126) or a fragment thereof, including a polypeptide composed of amino acid sequences selected from among SEQ ID NOs: 5, 14, 64, 73, 77, 79, 97, 103 and 120. Such assays may include one or more anti-MPHOSPH1 antibodies capable of recognizing and binding a MPHOSPH1 protein or fragments thereof, as appropriate. In the context of the present invention, anti-MPHOSPH1 antibodies binding to an MPHOSPH1 polypeptide will preferably recognize a polypeptide composed of amino acid sequences selected from among SEQ ID NOs: 5, 14, 64, 73, 77, 79, 97, 103 and 120 to the exclusion of other peptides. The binding specificity of antibody can be confirmed by means of an inhibition test. That is, when the binding between an antibody to be analyzed and full-length of MPHOSPH1 polypeptide is inhibited under presence of any fragment polypeptides having an amino acid sequence selected from among SEQ ID NOs: 5, 14, 64, 73, 77, 79, 97, 103 and 120, the antibody is deemed to specifically bind to the fragment. In the context of the present invention, such immunological assays are performed within various immunological assay formats well known in the art, including but not limited to, various types of radio-immunoassays, immunochromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers expressing MPHOSPH1 are also provided by the invention, including, but not limited to, radioscintigraphic imaging methods using labeled antibodies of the present invention. Such assays can clinically find use in the detection, monitoring, and prognosis of MPHOSPH1 expressing cancers, examples of which include, but are not limited to, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

The present invention also provides antibodies that bind to a peptide of the present invention. An antibody of the present invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the present invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, complete and partial peptides of a protein may serve as an immunization antigen. Examples of suitable partial peptides include, for example, the amino (N)-terminal or carboxy (C)-terminal fragment of a peptide of the present invention.

Herein, an antibody is defined as a protein that reacts with either the full length or a fragment of a MPHOSPH1 peptide. In a preferred embodiment, an antibody of the present invention will recognize fragment peptides of MPHOSPH1 that have an amino acid sequence selected from among SEQ ID NOs: 5, 14, 64, 73, 77, 79, 97, 103 and 120. Methods for synthesizing oligopeptide are well known in the arts. After the synthesis, peptides may be optionally purified prior to use as immunogen. In the present invention, the oligopeptide (e.g., 9- or 10mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the present invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, though preferably the compatibility with parental cells used for cell fusion is taken into account. In general, animals of Rodentia, Lagomorpha or Primate family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies for use in the context of the present invention, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, wherein a non-human animal is immunized with an antigen for preparing hybridoma, human lymphocytes such as those infected by EB virus may be immunized with a peptide, peptide expressing cells or their lysates in vitro. Then, the immunized lymphocytes may be fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas may then subsequently be transplanted into the abdominal cavity of a mouse and the ascites extracted. The obtained monoclonal antibodies can be purified by, for example, ammonium sulfate precipitation, a protein A or protein G column, DEAE ion exchange chromatography or an affinity column to which the peptide of the present invention is coupled. An antibody of the present invention can be used not only for purification and detection of a peptide of the present invention, but also as a candidate for agonists and antagonists of a peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

An antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Examples of suitable chromatography techniques, with the exception of affinity chromatography includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the peptide of the invention, by exposing the antibody of the invention to a sample assumed to contain the peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. VECTORS AND HOST CELLS

The present invention also provides vectors encoding a peptide of the present invention and host cells into which a polynucleotide encoding a peptide of the present invention is introduced. A vector of the present invention finds utility as a polynucleotide carrier, especially a DNA, of the present invention in host cell, to express the peptide of the present invention, or to administer the polynucleotide of the present invention for gene therapy.

When E. coli is selected as the host cell and the vector is amplified and produced in a large amount in E. coli (e.g., JM109, DH5 alpha, HB101 or XL1Blue), the vector should have an "ori" suitable for amplification in E. coli and a marker gene suitable for selected transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in E. coli should have the above characteristics to be amplified in E. coli. When E. coli, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the E. coli is the pelB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from Bacillus subtilis (e.g., pPL608, pKTH50) can be used for producing the polypeptide of the present invention.

In order to express the vector in animal cells, such as CHO, COS or NIH3T3 cells, the vector should carry a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Hereinafter, the present invention is described in more detail with reference to the Examples. However, while the following materials, methods and examples may serve to assist one of ordinary skill in making and using certain embodiments of the present invention, there are only intended to illustrate aspects of the present invention and thus in no way to limit the scope of the present invention. As one of ordinary skill in the art will readily recognize, methods and materials similar or equivalent to those described herein can be used in the practice or testing of the present invention.

EXAMPLES

Materials and Methods

Cell Lines

T2, HLA-A*0201-positive B-lymphoblastoid cell line, HLA-A*0206-positive B-lymphoblastoid cell line, HT1376, J82, COS7 and UM-UC3 were purchased from ATCC. MKN-45 was purchased from JCRB.

Candidate Selection of Peptides Derived from MPHOSPH1

9-mer and 10-mer peptides derived from MPHOSPH1 that bind to HLA-A*0201 molecule were predicted using binding prediction software "BIMAS" (http://www-bimas-.cit.nih.gov/molbio/hla_bind) (Parker et al., J Immunol 1994, 152(1): 163-75; Kuzushima et al., Blood 2001, 98(6): 1872-81). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide at 20 mg/ml and stored at −80 degrees C.

In Vitro CTL Induction

Monocyte-derived dendritic cells (DCs) were used as antigen-presenting cells to induce cytotoxic T lymphocyte (CTL) that responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells isolated from a normal volunteer (HLA-A*0201 positive) by Ficoll-Paque plus (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 microgram/ml of each of the synthesized peptides in the presence of 3 microgram/ml of beta 2-microglobulin for 3 hr at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X ray-irradiated (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTL was tested against peptide-pulsed T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 microliter/well of AIM-V Medium containing 5% AS. 50 microliter/well of IL-2 were added to the medium 10 days later to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon(IFN)-gamma enzyme-linked immunospot (ELISPOT) assay and IFN-gamma enzyme-linked immunosorbent assay (ELISA) were performed. Peptide-pulsed T2 ($1 \times 10^4$/well) was prepared as stimulator cells. Cultured cells in 48-well plate, CTL lines and CTL clones were used as responder cells. IFN-gamma ELISPOT assay and IFN-gamma ELISA assay were performed under manufacture procedure.

CTL Ability to Recognize the Target Cell Line that Endogenously Expressed MPHOSPH1 and HLA-A*0201

The CTL clone was examined for its ability to recognize the target cell that endogenously expressed MPHOSPH1 and HLA-A*0201. Established CTL clone was cultured with target cell lines ($5 \times 10^4$/well) for two overnight. After incubation, IFN-gamma in the culture media was measured by ELISA. IFN-gamma ELISA was performed under the manufacturer's procedure.

Cytotoxic Activity

The CTL clones were examined for their ability to kill the tumor cells endogenously expressing MPHOSPH1 and HLA-A*0201. Target cells (tumor cell lines) were labeled with 100 micro-Ci of $Na_2^{51}CrO_4$ (Perkin Elmer) for 1 hr in $CO_2$ incubator. Peptide-pulsed target cells were prepared by incubating the cells with 20 microgram/ml of the peptide for 16 hrs before labeling. Target cells labeled with $^{51}Cr$ were rinsed and mixed with CTL clones in a final volume of 200 microliter in 96-well round-bottom microtiter plates. The plates were centrifuged (4 minutes at 800 rpm) to increase cell-to-cell contact and placed into $CO_2$ incubator. After 4 hrs of incubation, 50 microliter of the supernatant was collected from each well and the radioactivity was determined with a gamma counter (PerkinElmer). The percentage of specific cytotoxicity was determined by calculating the percentage of specific $^{51}Cr$-release by the following formula: {(cpm of the test sample release−cpm of the spontaneous release)/(cpm of the maximum release−cpm of the spontaneous release)}×100. Spontaneous release was determined by incubating the target cells alone, in the absence of effector cells. The maximum release was obtained by incubating the targets with 1N HCl. All measurements were done in duplicate.

Establishment of the Cells Forcibly Expressing Either or Both of the Target Gene and HLA-A0206

The cDNA encoding an open reading frame of target genes or HLA-A*0206 was amplified by PCR. The PCR-amplified product was cloned into expression vector. The plasmids were transfected into COS7, which is the target gene and HLA-A*0206-null cell line, using lipofectamine 2000 (Invitrogen) according to the manufacturer's procedure. After 2 days from transfection, the transfected cells were harvested with versene (Invitrogen) and used as the stimulator cells (5×10⁴ cells/well) for CTL activity assay.

CTL Ability to Recognize the Target Cell Line that Endogenously Expressed MPHOSPH1 and HLA-A*0206

The CTL clone were examined for its ability to recognize the target cell that endogenously expressed MPHOSPH1 and HLA-A*0206. Established CTL line and clone were cultured with target cell lines (5×10⁴/well) for two overnight. After incubation, IFN-gamma in the culture media was measured by ELISA. IFN-gamma ELISA was performed under the manufacturer's procedure.

Results

Enhanced MPHOSPH1 Expression in Cancers

The wide gene expression profile data obtained from various cancers using cDNA-microarray revealed that MPHOSPH1 (GenBank Accession No. NM_016195; SEQ ID No: 125) expression was specifically elevated in cancer tissues as compared with corresponding normal tissue. MPHOSPH1 expression was validly elevated in 30 out of 31 Bladder cancer, 8 out of 36 Breast cancer, 18 out of 18 Cervical cancer, 5 out of 17 Cholangiocellular carcinoma, 25 out of 31 CML, 6 out of 11 Colorectal cancer, 6 out of 14 Gastric cancer, 5 out of 5 NSCLC, 7 out of 7 Lymphoma, 6 out of 10 Osteosarcoma, 7 out of 22 Prostate cancer, 10 out of 18 Renal cancer and 15 out of 21 Soft tissue tumor (Table 1).

TABLE 1

Ratio of cases observed up-regulation of MPHOSPH1 in cancerous tissue as compared with normal corresponding tissue.

| Cancer/Tumor | Ratio |
| --- | --- |
| Bladder cancer | 30/31 |
| Breast cancer | 8/36 |
| Cervical cancer | 18/18 |
| Cholangiocellular carcinoma | 5/17 |
| CML | 25/31 |
| Colorectal cancer | 6/11 |
| Gastric cancer | 6/14 |
| NSCLC | 5/5 |
| Lymphoma | 7/7 |
| Osteosarcoma | 6/10 |
| Prostate cancer | 7/22 |
| Renal cancer | 10/18 |
| Soft tissue tumor | 15/21 |

Prediction of HLA-A02 Binding Peptides Derived from MPHOSPH1

Tables 2a and 2b show the HLA-A02 binding 9mer and 10mer peptides of MPHOSPH1 in the order of high binding affinity. A total of 47 peptides having potential HLA-A02 binding ability were selected and examined to determine the epitope peptides.

TABLE 2a

HLA-A02 binding 9 mer peptides derived from MPHOSPH1

| Start Position | amino acid sequence | score | SEQ ID NO |
| --- | --- | --- | --- |
| 575 | KLLDLIEDL | 1278.3 | 1 |
| 282 | YIYDLFVPV | 1096.6 | 2 |

TABLE 2a-continued

HLA-A02 binding 9 mer peptides derived from MPHOSPH1

| Start Position | amino acid sequence | score | SEQ ID NO |
| --- | --- | --- | --- |
| 298 | KMLRLSQDV | 650.5 | 3 |
| 218 | ALLRQIKEV | 591.9 | 4 |
| 850 | FLLTIENEL | 363.6 | 5 |
| 1108 | ALSELTQGV | 285.2 | 6 |
| 331 | KLGIKHQSV | 243.4 | 7 |
| 1689 | TLQKFGDFL | 218.8 | 8 |
| 1251 | KLTDAKKQI | 149.7 | 9 |
| 638 | RLAIFKDLV | 129.5 | 10 |
| 1467 | QLTEKDSDL | 87.6 | 11 |
| 1195 | NLQDMKHLL | 87.6 | 12 |
| 270 | SVWVSFFEI | 83.5 | 13 |
| 129 | FQGCIMQPV | 74.6 | 14 |
| 839 | VLQENNEGL | 73.0 | 15 |
| 1094 | TLDVQIQHV | 64.0 | 16 |
| 1019 | AIWEECKEI | 48.8 | 17 |
| 1696 | FLQHSPSIL | 40.3 | 18 |
| 528 | DLMEDEDLV | 38.8 | 19 |
| 406 | SLLTLGKCI | 38.6 | 20 |
| 1400 | KLTNLQDEL | 36.6 | 21 |
| 170 | GILPRTLNV | 35.4 | 22 |
| 171 | ILPRTLNVL | 34.2 | 23 |
| 786 | KICSERKRV | 33.5 | 24 |
| 880 | SLSEKKNLT | 30.6 | 25 |
| 944 | LMHTKIDEL | 29.6 | 26 |
| 1422 | WLEEKMMLI | 29.0 | 27 |
| 466 | TLNVLKFSA | 28.8 | 28 |
| 1539 | KLQTEPLST | 26.1 | 29 |
| 132 | CIMQPVKDL | 25.0 | 30 |
| 1260 | KQVQKEVSV | 24.7 | 31 |
| 1184 | KLKEEITQL | 24.7 | 32 |
| 888 | TLSKEVQQI | 24.0 | 33 |
| 280 | NEYIYDLFV | 23.8 | 34 |
| 552 | LLDEDLDKT | 23.4 | 35 |
| 461 | LAYDETLNV | 21.5 | 36 |
| 980 | NLPNTQLDL | 21.4 | 37 |
| 409 | TLGKCINVL | 20.1 | 38 |
| 175 | TLNVLFDSL | 19.9 | 39 |

TABLE 2a-continued

HLA-A02 binding 9 mer peptides derived from MPHOSPH1

| Start Position | amino acid sequence | score | SEQ ID NO |
|---|---|---|---|
| 923 | KLSNEIETA | 19.6 | 40 |
| 1389 | KEHENNTDV | 19.4 | 41 |
| 987 | DLLGNDYLV | 19.3 | 42 |
| 920 | KIMKLSNEI | 18.6 | 43 |
| 1703 | ILQSKAKKI | 17.7 | 44 |
| 512 | ILNVKRATI | 17.7 | 45 |
| 1124 | KELETILET | 17.7 | 46 |
| 453 | IVNISQCYL | 17.5 | 47 |
| 771 | LICNETVEV | 16.3 | 48 |
| 623 | TLLQEREIL | 15.9 | 49 |
| 560 | TLEENKAFI | 15.1 | 50 |
| 1415 | YNADRKKWL | 14.5 | 51 |
| 307 | KGYSFIKDL | 13.7 | 52 |
| 133 | IMQPVKDLL | 12.9 | 53 |
| 1594 | KMAVKHPGC | 12.6 | 54 |
| 365 | SEMSRVIRV | 11.5 | 55 |
| 1191 | QLTNNLQDM | 11.4 | 56 |
| 871 | QIVHFQQEL | 11.2 | 57 |
| 245 | NISEFEESI | 11.0 | 58 |
| 484 | TLNSSQEKL | 10.5 | 59 |
| 764 | SLIINNKLI | 10.4 | 60 |
| 587 | LINEKKEKL | 10.0 | 61 |
| 263 | MANSIKFSV | 9.525 | 62 |
| 1354 | VLEAKLEEV | 8.528 | 63 |
| 846 | GLRAFLLTI | 6.93 | 64 |
| 83 | ILDSQTVVL | 5.956 | 65 |
| 1562 | VLDSCEVST | 5.067 | 66 |
| 15 | YVFSADPIA | 3.033 | 67 |
| 1741 | YTSEISSPI | 2.733 | 68 |
| 959 | SQISNIDLL | 2.441 | 69 |
| 82 | HILDSQTVV | 2.022 | 70 |

TABLE 2b

HLA-A02 binding 10 mer peptides derived from MPHOSPH1

| Start Position | amino acid sequence | score | SEQ ID NO |
|---|---|---|---|
| 1274 | KLLRiKINEL | 636.3 | 71 |
| 551 | KLLDeDLDKT | 445.9 | 72 |
| 460 | YLAYdETLNV | 319.9 | 73 |
| 943 | KLMHtKIDEL | 311.8 | 74 |
| 262 | NMANsIKFSV | 291.3 | 75 |
| 178 | VLFDsLQERL | 269.9 | 76 |
| 770 | KLICnETVEV | 243.4 | 77 |
| 34 | KLDLsREFSL | 173.5 | 78 |
| 407 | LLTLgKCINV | 118.2 | 79 |
| 1714 | TMSSsKLSNV | 115.5 | 80 |
| 1353 | QVLEaKLEEV | 104.0 | 81 |
| 880 | SLSEkKNLTL | 87.6 | 82 |
| 235 | TLYGsLTNSL | 68.4 | 83 |
| 1019 | AIWEeCKEIV | 65.4 | 84 |
| 552 | LLDEdLDKTL | 59.6 | 85 |
| 1093 | VTLDvQIQHV | 57.3 | 86 |
| 559 | KTLEeNKAFI | 42.3 | 87 |
| 1332 | KIIEdMRMTL | 42.2 | 88 |
| 152 | GLTNsGKTYT | 41.0 | 89 |
| 830 | NIAEiEDIRV | 39.2 | 90 |
| 586 | KLINeKKEKL | 36.6 | 91 |
| 182 | SLQErLYTKM | 30.6 | 92 |
| 1043 | QQIEkLQAEV | 28.9 | 93 |
| 870 | KQIVhFQQEL | 28.8 | 94 |
| 1318 | QQYErACKDL | 28.4 | 95 |
| 452 | MIVNiSQCYL | 27.5 | 96 |
| 923 | KLSNeIETAT | 26.1 | 97 |
| 1257 | KQIKqVQKEV | 24.7 | 98 |
| 980 | NLPNtQLDLL | 24.1 | 99 |
| 985 | QLDLIGNDYL | 23.0 | 100 |
| 1427 | MMLItQAKEA | 22.6 | 101 |
| 1523 | QIMDiKPKRI | 21.8 | 102 |
| 1484 | QLVAaLEIQL | 21.4 | 103 |
| 466 | TLNVlKFSAI | 19.8 | 104 |
| 511 | KILNvKRATI | 18.6 | 105 |
| 1340 | TLEEqEQTQV | 18.3 | 106 |
| 372 | RVSElSLCDL | 17.6 | 107 |
| 1561 | VVLDsCEVST | 16.8 | 108 |
| 309 | YSFTkDLQWT | 14.7 | 109 |

TABLE 2b-continued

HLA-A02 binding 10 mer peptides derived from MPHOSPH1

| Start Position | amino acid sequence | score | SEQ ID NO |
|---|---|---|---|
| 353 | SIFTvKILQI | 12.2 | 110 |
| 1094 | TLDVqIQHVV | 11.4 | 111 |
| 1688 | GTLQkFGDFL | 11.2 | 112 |
| 311 | FIKD1QWIQV | 10.7 | 113 |
| 1079 | TLIQqLKEEL | 10.5 | 114 |
| 1128 | TILEtQKVEC | 10.4 | 115 |
| 1487 | AALEiQLKAL | 10.4 | 116 |
| 170 | GILPrTLNVL | 10.2 | 117 |
| 503 | SLDSNSNSK1 | 4.173 | 118 |
| 1107 | RALSELTQGV | 3.574 | 119 |
| 282 | YIYDLFVPVS | 2.216 | 120 |
| 160 | YTFQGTEENI | 1.208 | 121 |
| 174 | RTLNVLFDSL | 1.022 | 122 |
| 82 | HILDSQTVVL | 0.621 | 123 |
| 128 | FFQGCIMQPV | 0.511 | 124 |

Start position indicates the number of amino acid residue from the N-terminus of MPHOSPH1. Binding score is derived from "BIMAS".

CTL Induction with the Predicted Peptides from MPHOSPH1 Restricted with HLA-A*0201

CTLs for those peptides derived from MPHOSPH1 were generated according to the protocols as described in "Materials and Methods". Peptide specific CTL activity was detected by IFN-gamma ELISPOT assay (FIG. 1). The well number #7 stimulated with MPHOSPH1-A02-9-850 (SEQ ID NO: 5) (a), #5 stimulated with MPHOSPH1-A02-9-129 (SEQ ID NO: 14) (b), #5 stimulated with MPHOSPH1-A02-9-846 (SEQ ID NO: 64) (c), #2 stimulated with MPHOSPH1-A02-10-460 (SEQ ID NO: 73) (d), #1 stimulated with MPHOSPH1-A02-10-770 (SEQ ID NO: 77) (e), #1 stimulated with MPHOSPH1-A02-10-407 (SEQ ID NO: 79) (f), #4 stimulated with MPHOSPH1-A02-10-923 (SEQ ID NO: 97) (g), #5 stimulated with MPHOSPH1-A02-10-1484 (SEQ ID NO: 103) (h) and #8 stimulated with MPHOSPH1-A02-10-282 (SEQ ID NO: 120) (i) demonstrated potent IFN-gamma production as compared to the control wells. On the other hand, no specific CTL activity was detected by stimulation with other peptides shown in Table 2 a and b, despite those peptides had possible binding activity with HLA-A*0201. As a typical case of negative data, no specific IFN-gamma production was observed from the CTL stimulated with MPHOSPH1-A02-9-575 (SEQ ID NO: 1) (j). Taken together, these results suggest that 10 selected peptides derived from MPHOSPH1 could induce potent CTLs.

Establishment of CTL Line and Clone Against MPHOSPH1 Derived Peptide

The cells in the well number #7 stimulated with MPHOSPH1-A02-9-850 (SEQ ID NO: 5) (a), #5 stimulated with MPHOSPH1-A02-9-129 (SEQ ID NO: 14) (b), #5 stimulated with MPHOSPH1-A02-9-846 (SEQ ID NO: 64) (c), #2 stimulated with MPHOSPH1-A02-10-460 (SEQ ID NO: 73) (d), #1 stimulated with MPHOSPH1-A02-10-770 (SEQ ID NO: 77) (e), #1 stimulated with MPHOSPH1-A02-10-407 (SEQ ID NO: 79) (f), #4 stimulated with MPHOSPH1-A02-10-923 (SEQ ID NO: 97) (g), #5 stimulated with MPHOSPH1-A02-10-1484 (SEQ ID NO: 103) (h) and #8 stimulated with MPHOSPH1-A02-10-282 (SEQ ID NO: 120) (i), which showed peptide specific CTL activity in IFN-gamma ELISPOT assay were expanded and established the CTL lines (FIG. 2). CTL activity of these CTL lines was measured by IFN-gamma ELISA. CTL lines demonstrated potent IFN-gamma production against T2 cells pulsed with the corresponding peptide as compared to T2 cells without peptide pulse. Furthermore, the CTL clones were established by limiting dilution from the CTL lines as described in "Materials and Methods", and IFN-gamma production from the CTL clones against T2 cells pulsed with corresponding peptide was measured by IFN-gamma ELISA. Potent IFN-gamma production was observed from the CTL clones stimulated with MPHOSPH1-A02-9-850 (SEQ ID NO: 5) (a), MPHOSPH1-A02-9-846 (SEQ ID NO: 64) (b), MPHOSPH1-A02-10-460 (SEQ ID NO: 73) (c), MPHOSPH1-A02-10-770 (SEQ ID NO: 77) (d) and MPHOSPH1-A02-10-282 (SEQ ID NO: 120) (e) (FIG. 3).

Specific CTL Activity Against Target Cells Expressing MPHOSPH1 and HLA-A*0201

The established CTL clone was examined for the ability to recognize target cells that express MPHOSPH1 and HLA-A*0201 molecule. The CTL clone stimulated with MPHOSPH1-A02-10-282 (SEQ ID NO: 120) showed potent CTL activity against J82 cells which both express MPHOSPH1 and HLA-A*0201. On the other hand, no significant specific CTL activity was detected against HT1376 cells which express MPHOSPH1 but not HLA-A*0201 and T2 cells which express HLA-A*0201 but not MPHOSPH1 (FIG. 4). Thus, this data clearly demonstrates that MPHOSPH1-A02-10-282 (SEQ ID NO: 120) peptide was endogenously processed and expressed on the target cells with HLA-A*0201 molecule and was recognized by the CTLs.

Cytotoxic Activity Against Tumor Cell Line Expressing MPHOSPH1 and HLA-A*0201

Figure 5:
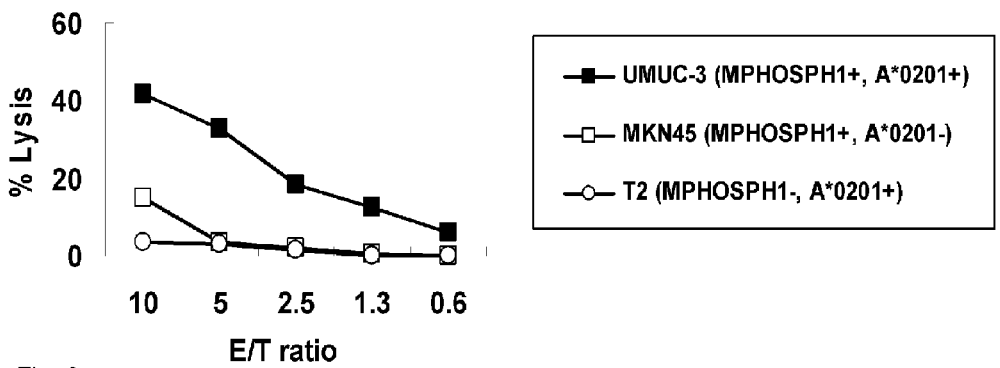
FIG. 5 is a line graph depicting cytotoxic activity of CTL against the tumor cell lines. UMUC-3 cells which express both MPHOSPH1 and HLA-A*0201, MKN45 cells which express MPHOSPH1 but not HLA-A*0201 and T2 that expressed HLA-A*0201 but not MPHOSPH1 were used as target cells. The CTL clone established with MPHOSPH1-A02-10-282 (SEQ ID NO: 120) showed potent cytotoxic activity against UMUC-3 cells. On the other hand, no significant specific CTL activity was detected against MKN45 and T2 cells. E/T ratio indicates the ratio of the number of the effector cells (CTL clone) and the target cells.

The established CTL clones were examined for their ability to recognize and kill tumor cell lines that expressed MPHOSPH1 and HLA-A*0201. The CTL clone stimulated with MPHOSPH1-A02-10-282 (SEQ ID NO: 120) showed potent cytotoxic activity against UMUC-3 cells which both express MPHOSPH1 and HLA-A*0201. On the other hand, no significant cytotoxic activity was detected with both CTL clones against MKN45 cells which express MPHOSPH1 but not HLA-A*0201 and T2 cells which express HLA-A*0201 but not MPHOSPH1 (FIG. 5). These results indicate that MPHOSPH1-A02-10-282 (SEQ ID NO: 120) peptide derived from MPHOSPH1 may be available to apply the cancer vaccines for patients with MPHOSPH1 expressing tumors.

Specific CTL Activity Against Target Cells Expressing MPHOSPH1 and HLA-A*0206

Figure 6:
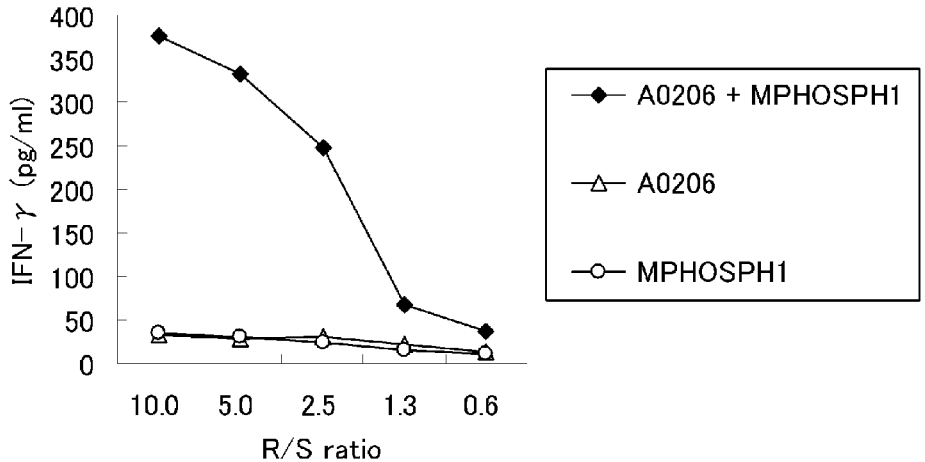
FIG. 6 is a line graph depicting cytotoxic activity of CTL against the target cells that express MPHOSPH1 and HLA-A*0206. COS7 cells transfected with HLA-A*0206 or the full length MPHOSPH1 gene were prepared as the controls. The CTL line established with MPHOSPH1-A02-10-282 (SEQ ID NO: 120) showed specific CTL activity against COS7 cells transfected with both MPHOSPH1 and HLA-A*0206 (black lozenge). On the other hand, no significant specific CTL activity was detected against target cells expressing either HLA-A*0206 (triangle) or MPHOSPH1 (circle).

The established CTL line raised against MPHOSPH1-A02-10-282 (SEQ ID NO: 120) peptide was examined for the ability to recognize target cells that express MPHOSPH1 and HLA-A*0206 molecule. COS7 cells transfected with both the full length of MPHOSPH1 and HLA-A*0206 gene (a specific model for the target cells that express MPHOSPH1 and HLA-A*0206 gene) were prepared as a stimulator cells, and COS7 cells transfected with either full length of MPHOSPH1 or HLA-A*0206 were used as the controls. In FIG. 6, the CTL clone stimulated with MPHOSPH1-A02-10-282 (SEQ ID NO: 120) showed potent CTL activity against COS7 cells expressing both MPHOSPH1 and HLA-A*0206. On the other hand, no significant specific CTL activity was detected against the controls. Thus, these data clearly demonstrate that MPHOSPH1-A02-10-282 (SEQ ID NO: 120) peptide is endogenously processed and expressed on the target cells with HLA-A*0206 molecule and was recognized by the CTLs.

Homology Analysis of Antigen Peptides

The CTLs stimulated with MPHOSPH1-A02-9-850 (SEQ ID NO: 5), MPHOSPH1-A02-9-129 (SEQ ID NO: 14), MPHOSPH1-A02-9-846 (SEQ ID NO: 64), MPHOSPH1-A02-10-460 (SEQ ID NO: 73), MPHOSPH1-A02-10-770 (SEQ ID NO: 77), MPHOSPH1-A02-10-407 (SEQ ID NO: 79), MPHOSPH1-A02-10-923 (SEQ ID NO: 97), MPHOSPH1-A02-10-1484 (SEQ ID NO: 103) and MPHOSPH1-A02-10-282 (SEQ ID NO: 120) showed significant and specific CTL activity. This result may be due to the fact that the sequence of MPHOSPH1-A02-9-850 (SEQ ID NO: 5), MPHOSPH1-A02-9-129 (SEQ ID NO: 14), MPHOSPH1-A02-9-846 (SEQ ID NO: 64), MPHOSPH1-A02-10-460 (SEQ ID NO: 73), MPHOSPH1-A02-10-770 (SEQ ID NO: 77), MPHOSPH1-A02-10-407 (SEQ ID NO: 79), MPHOSPH1-A02-10-923 (SEQ ID NO: 97), MPHOSPH1-A02-10-1484 (SEQ ID NO: 103) and MPHOSPH1-A02-10-282 (SEQ ID NO: 120) are homologous to peptide derived from other molecules that are known to sensitize the human immune system. To exclude this possibility, homology analyses were performed for these peptide sequences using as queries the BLAST algorithm (http://www.ncbi.nlm.nih.gov/blast/blast.cgi) which revealed no sequence with significant homology. The results of homology analyses indicate that the sequence of MPHOSPH1-A02-9-850 (SEQ ID NO: 5), MPHOSPH1-A02-9-129 (SEQ ID NO: 14), MPHOSPH1-A02-9-846 (SEQ ID NO: 64), MPHOSPH1-A02-10-460 (SEQ ID NO: 73), MPHOSPH1-A02-10-770 (SEQ ID NO: 77), MPHOSPH1-A02-10-407 (SEQ ID NO: 79), MPHOSPH1-A02-10-923 (SEQ ID NO: 97), MPHOSPH1-A02-10-1484 (SEQ ID NO: 103) and MPHOSPH1-A02-10-282 (SEQ ID NO: 120) are unique and thus, there is little possibility, to our best knowledge, that this molecules raise unintended immunologic response to some unrelated molecule.

In conclusion, the novel HLA-A*0201 epitope peptides derived from MPHOSPH1 identified herein may find utility in the field of cancer immunotherapy.

INDUSTRIAL APPLICABILITY

The present invention provides new TAAs, particularly those derived from MPHOSPH1, that may induce potent and specific anti-tumor immune responses and thus have applicability to a wide variety of cancer types. Such TAAs can find use as peptide vaccines against diseases associated with MPHOSPH1, e.g., cancer, more particularly, bladder cancer, breast cancer, cervical cancer, cholangiocellular carcinoma, CML, colorectal cancer, gastric cancer, NSCLC, lymphoma, osteosarcoma, prostate cancer, renal cancer and soft tissue tumor.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. An isolated peptide of less than 15 amino acids that comprises an amino acid sequence in which 1 or 2 amino acid(s) are substituted, inserted, and/or added in the amino acid sequence as shown in SEQ ID NO: 120, and wherein the peptide has cytotoxic T lymphocyte (CTL) inducibility.

2. The isolated peptide of claim 1, wherein the peptide has one or both of the following characteristics:
   (a) the second amino acid from the N-terminus of the amino acid sequence as shown in SEQ ID NO: 120 is substituted with the amino acid selected from the group consisting of leucine and methionine; and
   (b) the C-terminal amino acid of the amino acid sequence as shown in SEQ ID NO: 120 is substituted with the amino acid selected from the group consisting of valine and leucine.

3. A composition for inducing a CTL, wherein the composition comprises a peptide of the following (a) or (b):
   (a) a peptide of less than 15 amino acids that comprises the amino acid sequence as shown in SEQ ID NO: 120;
   (b) a peptide of less than 15 amino acids that comprises an amino acid sequence in which 1 or 2 amino acid(s) are substituted, inserted, and/or added in the amino acid sequence as shown in SEQ ID NO: 120, and wherein the peptide has cytotoxic T lymphocyte (CTL) inducibility in combination with an adjuvant.

4. The composition of claim 3, wherein the peptide consists of the amino acid sequence as shown in SEQ ID NO: 120.

5. A composition for inducing an antigen-presenting cell (APC) having CTL inducibility, wherein the composition comprises a peptide of the following (a) or (b):
   (a) a peptide of less than 15 amino acids that comprises the amino acid sequence as shown in SEQ ID NO: 120;
   (b) a peptide of less than 15 amino acids that comprises an amino acid sequence in which 1 or 2 amino acid(s) are substituted, inserted, and/or added in the amino acid sequence as shown in SEQ ID NO: 120, and wherein the peptide has cytotoxic T lymphocyte (CTL) inducibility in combination with an adjuvant.

6. The composition of claim 5, wherein the peptide consists of the amino acid sequence as shown in SEQ ID NO: 120.

7. A pharmaceutical composition comprising a peptide of the following (a) or (b):
   (a) a peptide of less than 15 amino acids that comprises the amino acid sequence as shown in SEQ ID NO: 120;
   (b) a peptide of less than 15 amino acids that comprises an amino acid sequence in which 1 or 2 amino acid(s) are substituted, inserted, and/or added in the amino acid sequence as shown in SEQ ID NO: 120, and wherein the peptide has cytotoxic T lymphocyte CTL inducibility in combination with an adjuvant.

8. The pharmaceutical composition of claim 7, wherein the peptide consists of the amino acid sequence as shown in SEQ ID NO: 120.

9. A method for inducing an antigen-presenting cell (APC) having CTL inducibility, said method comprising contacting an APC with a peptide in vitro, ex vivo or in vivo wherein the peptide is:
   (a) a peptide of less than 15 amino acids that comprises the amino acid sequence as shown in SEQ ID NO: 120; or
   (b) a peptide of less than 15 amino acids that comprises an amino acid sequence in which 1 or 2 amino acid(s) are substituted, inserted, and/or added in the amino acid sequence as shown in SEQ ID NO: 120, and wherein the peptide has cytotoxic T lymphocyte (CTL) inducibility.

10. A method for inducing a CTL, said method comprising a step selected from the group consisting of:
   (i) co-culturing a CD8 positive T cell with an APC that presents on its surface a complex of an HLA antigen and a peptide; and
   (ii) co-culturing a CD8 positive T cell with an exosome that presents on its surface a complex of an HLA antigen and the peptide of
wherein the peptide is:
(a) a peptide of less than 15 amino acids that comprises the amino acid sequence as shown in SEQ ID NO: 120; or
(b) a peptide of less than 15 amino acids that comprises an amino acid sequence in which 1 or 2 amino acid(s) are substituted, inserted, and/or added in the amino acid sequence as shown in SEQ ID NO: 120, and wherein the peptide has cytotoxic T lymphocyte (CTL) inducibility.

* * * * *

SEQUENCE LISTING

```
<160> NUMBER OF SEQ ID NOS: 130

<210> SEQ ID NO 1
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 1

Lys Leu Leu Asp Leu Ile Glu Asp Leu
1               5

<210> SEQ ID NO 2
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 2

Tyr Ile Tyr Asp Leu Phe Val Pro Val
1               5

<210> SEQ ID NO 3
<211> LENGTH: 9
<212> TYPE: PRT
<213> ORGANISM: Artificial Sequence
<220> FEATURE:
```

<223> OTHER INFORMATION: a peptide derived from MPHOSPH1

<400> SEQUENCE: 3

Lys Met Leu Arg Leu Ser Gln Asp Val
1               5

<210> SEQ ID NO 4
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 4

Ala Leu Leu Arg Gln Ile Lys Glu Val
1               5

<210> SEQ ID NO 5
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 5

Phe Leu Leu Thr Ile Glu Asn Glu Leu
1               5

<210> SEQ ID NO 6
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 6

Ala Leu Ser Glu Leu Thr Gln Gly Val
1               5

<210> SEQ ID NO 7
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 7

Lys Leu Gly Ile Lys His Gln Ser Val
1               5

<210> SEQ ID NO 8
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 8

Thr Leu Gln Lys Phe Gly Asp Phe Leu
1               5

<210> SEQ ID NO 9
<211> LENGTH: 9
<212> TYPE: PRT
<213> ORGANISM: Artificial Sequence
<220> FEATURE:
<223> OTHER INFORMATION: a peptide derived from MPHOSPH1

```
<400> SEQUENCE: 9

Lys Leu Thr Asp Ala Lys Lys Gln Ile
1               5

<210> SEQ ID NO 10
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 10

Arg Leu Ala Ile Phe Lys Asp Leu Val
1               5

<210> SEQ ID NO 11
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 11

Gln Leu Thr Glu Lys Asp Ser Asp Leu
1               5

<210> SEQ ID NO 12
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 12

Asn Leu Gln Asp Met Lys His Leu Leu
1               5

<210> SEQ ID NO 13
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 13

Ser Val Trp Val Ser Phe Phe Glu Ile
1               5

<210> SEQ ID NO 14
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 14

Phe Gln Gly Cys Ile Met Gln Pro Val
1               5

<210> SEQ ID NO 15
<211> LENGTH: 9
<212> TYPE: PRT
<213> ORGANISM: Artificial Sequence
<220> FEATURE:
<223> OTHER INFORMATION: a peptide derived from MPHOSPH1
```

```
<400> SEQUENCE: 15

Val Leu Gln Glu Asn Asn Glu Gly Leu
1               5

<210> SEQ ID NO 16
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 16

Thr Leu Asp Val Gln Ile Gln His Val
1               5

<210> SEQ ID NO 17
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 17

Ala Ile Trp Glu Glu Cys Lys Glu Ile
1               5

<210> SEQ ID NO 18
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 18

Phe Leu Gln His Ser Pro Ser Ile Leu
1               5

<210> SEQ ID NO 19
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 19

Asp Leu Met Glu Asp Glu Asp Leu Val
1               5

<210> SEQ ID NO 20
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 20

Ser Leu Leu Thr Leu Gly Lys Cys Ile
1               5

<210> SEQ ID NO 21
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 21
```

```
Lys Leu Thr Asn Leu Gln Asp Glu Leu
1               5

<210> SEQ ID NO 22
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 22

Gly Ile Leu Pro Arg Thr Leu Asn Val
1               5

<210> SEQ ID NO 23
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 23

Ile Leu Pro Arg Thr Leu Asn Val Leu
1               5

<210> SEQ ID NO 24
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 24

Lys Ile Cys Ser Glu Arg Lys Arg Val
1               5

<210> SEQ ID NO 25
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 25

Ser Leu Ser Glu Lys Lys Asn Leu Thr
1               5

<210> SEQ ID NO 26
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 26

Leu Met His Thr Lys Ile Asp Glu Leu
1               5

<210> SEQ ID NO 27
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 27
```

```
Trp Leu Glu Glu Lys Met Met Leu Ile
1               5

<210> SEQ ID NO 28
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 28

Thr Leu Asn Val Leu Lys Phe Ser Ala
1               5

<210> SEQ ID NO 29
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 29

Lys Leu Gln Thr Glu Pro Leu Ser Thr
1               5

<210> SEQ ID NO 30
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 30

Cys Ile Met Gln Pro Val Lys Asp Leu
1               5

<210> SEQ ID NO 31
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 31

Lys Gln Val Gln Lys Glu Val Ser Val
1               5

<210> SEQ ID NO 32
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 32

Lys Leu Lys Glu Glu Ile Thr Gln Leu
1               5

<210> SEQ ID NO 33
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 33

Thr Leu Ser Lys Glu Val Gln Gln Ile
```

```
1               5

<210> SEQ ID NO 34
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 34

Asn Glu Tyr Ile Tyr Asp Leu Phe Val
1               5

<210> SEQ ID NO 35
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 35

Leu Leu Asp Glu Asp Leu Asp Lys Thr
1               5

<210> SEQ ID NO 36
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 36

Leu Ala Tyr Asp Glu Thr Leu Asn Val
1               5

<210> SEQ ID NO 37
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 37

Asn Leu Pro Asn Thr Gln Leu Asp Leu
1               5

<210> SEQ ID NO 38
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 38

Thr Leu Gly Lys Cys Ile Asn Val Leu
1               5

<210> SEQ ID NO 39
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 39

Thr Leu Asn Val Leu Phe Asp Ser Leu
1               5
```

```
<210> SEQ ID NO 40
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 40

Lys Leu Ser Asn Glu Ile Glu Thr Ala
1               5

<210> SEQ ID NO 41
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 41

Lys Glu His Glu Asn Asn Thr Asp Val
1               5

<210> SEQ ID NO 42
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 42

Asp Leu Leu Gly Asn Asp Tyr Leu Val
1               5

<210> SEQ ID NO 43
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 43

Lys Ile Met Lys Leu Ser Asn Glu Ile
1               5

<210> SEQ ID NO 44
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 44

Ile Leu Gln Ser Lys Ala Lys Lys Ile
1               5

<210> SEQ ID NO 45
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 45

Ile Leu Asn Val Lys Arg Ala Thr Ile
1               5
```

<210> SEQ ID NO 46
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 46

Lys Glu Leu Glu Thr Ile Leu Glu Thr
1               5

<210> SEQ ID NO 47
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 47

Ile Val Asn Ile Ser Gln Cys Tyr Leu
1               5

<210> SEQ ID NO 48
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 48

Leu Ile Cys Asn Glu Thr Val Glu Val
1               5

<210> SEQ ID NO 49
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 49

Thr Leu Leu Gln Glu Arg Glu Ile Leu
1               5

<210> SEQ ID NO 50
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 50

Thr Leu Glu Glu Asn Lys Ala Phe Ile
1               5

<210> SEQ ID NO 51
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 51

Tyr Asn Ala Asp Arg Lys Lys Trp Leu
1               5

```
<210> SEQ ID NO 52
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 52

Lys Gly Tyr Ser Phe Ile Lys Asp Leu
1               5

<210> SEQ ID NO 53
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 53

Ile Met Gln Pro Val Lys Asp Leu Leu
1               5

<210> SEQ ID NO 54
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 54

Lys Met Ala Val Lys His Pro Gly Cys
1               5

<210> SEQ ID NO 55
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 55

Ser Glu Met Ser Arg Val Ile Arg Val
1               5

<210> SEQ ID NO 56
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 56

Gln Leu Thr Asn Asn Leu Gln Asp Met
1               5

<210> SEQ ID NO 57
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 57

Gln Ile Val His Phe Gln Gln Glu Leu
1               5

<210> SEQ ID NO 58
```

```
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 58

Asn Ile Ser Glu Phe Glu Glu Ser Ile
1               5

<210> SEQ ID NO 59
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 59

Thr Leu Asn Ser Ser Gln Glu Lys Leu
1               5

<210> SEQ ID NO 60
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 60

Ser Leu Ile Ile Asn Asn Lys Leu Ile
1               5

<210> SEQ ID NO 61
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 61

Leu Ile Asn Glu Lys Lys Glu Lys Leu
1               5

<210> SEQ ID NO 62
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 62

Met Ala Asn Ser Ile Lys Phe Ser Val
1               5

<210> SEQ ID NO 63
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 63

Val Leu Glu Ala Lys Leu Glu Glu Val
1               5

<210> SEQ ID NO 64
<211> LENGTH: 9
```

```
<212> TYPE: PRT
<213> ORGANISM: Artificial Sequence
<220> FEATURE:
<223> OTHER INFORMATION: a peptide derived from MPHOSPH1

<400> SEQUENCE: 64

Gly Leu Arg Ala Phe Leu Leu Thr Ile
1               5

<210> SEQ ID NO 65
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 65

Ile Leu Asp Ser Gln Thr Val Val Leu
1               5

<210> SEQ ID NO 66
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 66

Val Leu Asp Ser Cys Glu Val Ser Thr
1               5

<210> SEQ ID NO 67
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 67

Tyr Val Phe Ser Ala Asp Pro Ile Ala
1               5

<210> SEQ ID NO 68
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 68

Tyr Thr Ser Glu Ile Ser Ser Pro Ile
1               5

<210> SEQ ID NO 69
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 69

Ser Gln Ile Ser Asn Ile Asp Leu Leu
1               5

<210> SEQ ID NO 70
<211> LENGTH: 9
<212> TYPE: PRT
```

<213> ORGANISM: Artificial Sequence
<220> FEATURE:
<223> OTHER INFORMATION: a peptide derived from MPHOSPH1

<400> SEQUENCE: 70

His Ile Leu Asp Ser Gln Thr Val Val
1               5

<210> SEQ ID NO 71
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 71

Lys Leu Leu Arg Ile Lys Ile Asn Glu Leu
1               5                   10

<210> SEQ ID NO 72
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 72

Lys Leu Leu Asp Glu Asp Leu Asp Lys Thr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 73

Tyr Leu Ala Tyr Asp Glu Thr Leu Asn Val
1               5                   10

<210> SEQ ID NO 74
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 74

Lys Leu Met His Thr Lys Ile Asp Glu Leu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 75

Asn Met Ala Asn Ser Ile Lys Phe Ser Val
1               5                   10

<210> SEQ ID NO 76
<211> LENGTH: 10
<212> TYPE: PRT
<213> ORGANISM: Artificial Sequence

```
<220> FEATURE:
<223> OTHER INFORMATION: a peptide derived from MPHOSPH1

<400> SEQUENCE: 76

Val Leu Phe Asp Ser Leu Gln Glu Arg Leu
1               5                   10

<210> SEQ ID NO 77
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 77

Lys Leu Ile Cys Asn Glu Thr Val Glu Val
1               5                   10

<210> SEQ ID NO 78
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 78

Lys Leu Asp Leu Ser His Glu Phe Ser Leu
1               5                   10

<210> SEQ ID NO 79
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 79

Leu Leu Thr Leu Gly Lys Cys Ile Asn Val
1               5                   10

<210> SEQ ID NO 80
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 80

Thr Met Ser Ser Ser Lys Leu Ser Asn Val
1               5                   10

<210> SEQ ID NO 81
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 81

Gln Val Leu Glu Ala Lys Leu Glu Glu Val
1               5                   10

<210> SEQ ID NO 82
<211> LENGTH: 10
<212> TYPE: PRT
<213> ORGANISM: Artificial Sequence
<220> FEATURE:
```

<223> OTHER INFORMATION: a peptide derived from MPHOSPH1

<400> SEQUENCE: 82

Ser Leu Ser Glu Lys Lys Asn Leu Thr Leu
1               5                   10

<210> SEQ ID NO 83
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 83

Thr Leu Tyr Gly Ser Leu Thr Asn Ser Leu
1               5                   10

<210> SEQ ID NO 84
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 84

Ala Ile Trp Glu Glu Cys Lys Glu Ile Val
1               5                   10

<210> SEQ ID NO 85
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 85

Leu Leu Asp Glu Asp Leu Asp Lys Thr Leu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 86

Val Thr Leu Asp Val Gln Ile Gln His Val
1               5                   10

<210> SEQ ID NO 87
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 87

Lys Thr Leu Glu Glu Asn Lys Ala Phe Ile
1               5                   10

<210> SEQ ID NO 88
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 88

Lys Ile Ile Glu Asp Met Arg Met Thr Leu
1               5                   10

<210> SEQ ID NO 89
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 89

Gly Leu Thr Asn Ser Gly Lys Thr Tyr Thr
1               5                   10

<210> SEQ ID NO 90
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 90

Asn Ile Ala Glu Ile Glu Asp Ile Arg Val
1               5                   10

<210> SEQ ID NO 91
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 91

Lys Leu Ile Asn Glu Lys Lys Glu Lys Leu
1               5                   10

<210> SEQ ID NO 92
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 92

Ser Leu Gln Glu Arg Leu Tyr Thr Lys Met
1               5                   10

<210> SEQ ID NO 93
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 93

Gln Gln Ile Glu Lys Leu Gln Ala Glu Val
1               5                   10

<210> SEQ ID NO 94
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 94

Lys Gln Ile Val His Phe Gln Gln Glu Leu
1               5                   10

<210> SEQ ID NO 95
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 95

Gln Gln Tyr Glu Arg Ala Cys Lys Asp Leu
1               5                   10

<210> SEQ ID NO 96
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 96

Met Ile Val Asn Ile Ser Gln Cys Tyr Leu
1               5                   10

<210> SEQ ID NO 97
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 97

Lys Leu Ser Asn Glu Ile Glu Thr Ala Thr
1               5                   10

<210> SEQ ID NO 98
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 98

Lys Gln Ile Lys Gln Val Gln Lys Glu Val
1               5                   10

<210> SEQ ID NO 99
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 99

Asn Leu Pro Asn Thr Gln Leu Asp Leu Leu
1               5                   10

<210> SEQ ID NO 100
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 100

```
Gln Leu Asp Leu Leu Gly Asn Asp Tyr Leu
 1               5                  10

<210> SEQ ID NO 101
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 101

Met Met Leu Ile Thr Gln Ala Lys Glu Ala
 1               5                  10

<210> SEQ ID NO 102
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 102

Gln Ile Met Asp Ile Lys Pro Lys Arg Ile
 1               5                  10

<210> SEQ ID NO 103
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 103

Gln Leu Val Ala Ala Leu Glu Ile Gln Leu
 1               5                  10

<210> SEQ ID NO 104
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 104

Thr Leu Asn Val Leu Lys Phe Ser Ala Ile
 1               5                  10

<210> SEQ ID NO 105
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 105

Lys Ile Leu Asn Val Lys Arg Ala Thr Ile
 1               5                  10

<210> SEQ ID NO 106
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 106
```

```
Thr Leu Glu Glu Gln Glu Gln Thr Gln Val
1               5                   10
```

<210> SEQ ID NO 107
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 107

```
Arg Val Ser Glu Leu Ser Leu Cys Asp Leu
1               5                   10
```

<210> SEQ ID NO 108
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 108

```
Val Val Leu Asp Ser Cys Glu Val Ser Thr
1               5                   10
```

<210> SEQ ID NO 109
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 109

```
Tyr Ser Phe Ile Lys Asp Leu Gln Trp Ile
1               5                   10
```

<210> SEQ ID NO 110
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 110

```
Ser Ile Phe Thr Val Lys Ile Leu Gln Ile
1               5                   10
```

<210> SEQ ID NO 111
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 111

```
Thr Leu Asp Val Gln Ile Gln His Val Val
1               5                   10
```

<210> SEQ ID NO 112
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 112

Gly Thr Leu Gln Lys Phe Gly Asp Phe Leu

<210> SEQ ID NO 113
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 113

Phe Ile Lys Asp Leu Gln Trp Ile Gln Val
1               5                   10

<210> SEQ ID NO 114
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 114

Thr Leu Ile Gln Gln Leu Lys Glu Glu Leu
1               5                   10

<210> SEQ ID NO 115
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 115

Thr Ile Leu Glu Thr Gln Lys Val Glu Cys
1               5                   10

<210> SEQ ID NO 116
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 116

Ala Ala Leu Glu Ile Gln Leu Lys Ala Leu
1               5                   10

<210> SEQ ID NO 117
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 117

Gly Ile Leu Pro Arg Thr Leu Asn Val Leu
1               5                   10

<210> SEQ ID NO 118
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 118

Ser Leu Asp Ser Asn Ser Asn Ser Lys Ile
1               5                   10

<210> SEQ ID NO 119
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 119

Arg Ala Leu Ser Glu Leu Thr Gln Gly Val
1               5                   10

<210> SEQ ID NO 120
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 120

Tyr Ile Tyr Asp Leu Phe Val Pro Val Ser
1               5                   10

<210> SEQ ID NO 121
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 121

Tyr Thr Phe Gln Gly Thr Glu Glu Asn Ile
1               5                   10

<210> SEQ ID NO 122
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 122

Arg Thr Leu Asn Val Leu Phe Asp Ser Leu
1               5                   10

<210> SEQ ID NO 123
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 123

His Ile Leu Asp Ser Gln Thr Val Val Leu
1               5                   10

<210> SEQ ID NO 124
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 124

Phe Phe Gln Gly Cys Ile Met Gln Pro Val
1               5                   10

<210> SEQ ID NO 125
<211> LENGTH: 6319
<212> TYPE: DNA
<213> ORGANISM: Homo sapiens
<220> FEATURE:
<221> NAME/KEY: CDS
<222> LOCATION: (73)..(5415)

<400> SEQUENCE: 125

```
attgtttgaa tttgaaaacg gtaacatcgc agtgctgctc gcgggtctgg ctagtcaggc        60
gaagtttgca ga atg gaa tct aat ttt aat caa gag gga gta cct cga cca       111
              Met Glu Ser Asn Phe Asn Gln Glu Gly Val Pro Arg Pro
                1               5                  10 tct tat gtt ttt agt gct gac cca att gca agg cct tca gaa ata aat        159
Ser Tyr Val Phe Ser Ala Asp Pro Ile Ala Arg Pro Ser Glu Ile Asn
    15                  20                  25 ttc gat ggc att aag ctt gat ctg tct cat gaa ttt tcc tta gtt gct        207
Phe Asp Gly Ile Lys Leu Asp Leu Ser His Glu Phe Ser Leu Val Ala
30                  35                  40                  45 cca aat act gag gca aac agt ttc gaa tct aaa gat tat ctc cag gtt        255
Pro Asn Thr Glu Ala Asn Ser Phe Glu Ser Lys Asp Tyr Leu Gln Val
                50                  55                  60 tgt ctt cga ata aga cca ttt aca cag tca gaa aaa gaa ctt gag tct        303
Cys Leu Arg Ile Arg Pro Phe Thr Gln Ser Glu Lys Glu Leu Glu Ser
            65                  70                  75 gag ggc tgt gtg cat att ctg gat tca cag act gtt gtg ctg aaa gag        351
Glu Gly Cys Val His Ile Leu Asp Ser Gln Thr Val Val Leu Lys Glu
        80                  85                  90 cct caa tgc atc ctt ggt cgg tta agt gaa aaa agc tca ggg cag atg        399
Pro Gln Cys Ile Leu Gly Arg Leu Ser Glu Lys Ser Ser Gly Gln Met
    95                  100                 105 gca cag aaa ttc agt ttt tcc aag gtt ttt ggc cca gca act aca cag        447
Ala Gln Lys Phe Ser Phe Ser Lys Val Phe Gly Pro Ala Thr Thr Gln
110                 115                 120                 125 aag gaa ttc ttt cag ggt tgc att atg caa cca gta aaa gac ctc ttg        495
Lys Glu Phe Phe Gln Gly Cys Ile Met Gln Pro Val Lys Asp Leu Leu
                130                 135                 140 aaa gga cag agt cgt ctg att ttt act tac ggg cta acc aat tca gga        543
Lys Gly Gln Ser Arg Leu Ile Phe Thr Tyr Gly Leu Thr Asn Ser Gly
            145                 150                 155 aaa aca tat aca ttt caa ggg aca gaa gaa aat att ggc att ctg cct        591
Lys Thr Tyr Thr Phe Gln Gly Thr Glu Glu Asn Ile Gly Ile Leu Pro
        160                 165                 170 cga act ttg aat gta tta ttt gat agt ctt caa gaa aga ctg tat aca        639
Arg Thr Leu Asn Val Leu Phe Asp Ser Leu Gln Glu Arg Leu Tyr Thr
    175                 180                 185 aag atg aac ctt aaa cca cat aga tcc aga gaa tac tta agg tta tca        687
Lys Met Asn Leu Lys Pro His Arg Ser Arg Glu Tyr Leu Arg Leu Ser
190                 195                 200                 205 tca gaa caa gag aaa gaa gaa att gct agc aaa agt gca ttg ctt cgg        735
Ser Glu Gln Glu Lys Glu Glu Ile Ala Ser Lys Ser Ala Leu Leu Arg
                210                 215                 220 caa att aaa gag gtt act gtg cat aat gat agt gat gat act ctt tat        783
Gln Ile Lys Glu Val Thr Val His Asn Asp Ser Asp Asp Thr Leu Tyr
            225                 230                 235 gga agt tta act aac tct ttg aat atc tca gag ttt gaa gaa tcc ata        831
Gly Ser Leu Thr Asn Ser Leu Asn Ile Ser Glu Phe Glu Glu Ser Ile
        240                 245                 250 aaa gat tat gaa caa gcc aac ttg aat atg gct aat agt ata aaa ttt        879
Lys Asp Tyr Glu Gln Ala Asn Leu Asn Met Ala Asn Ser Ile Lys Phe
```

-continued

```
                255                 260                 265
tct gtg tgg gtt tct ttc ttt gaa att tac aat gaa tat att tat gac      927
Ser Val Trp Val Ser Phe Phe Glu Ile Tyr Asn Glu Tyr Ile Tyr Asp
270                 275                 280                 285 tta ttt gtt cct gta tca tct aaa ttc caa aag aga aag atg ctg cgc      975
Leu Phe Val Pro Val Ser Ser Lys Phe Gln Lys Arg Lys Met Leu Arg
                290                 295                 300 ctt tcc caa gac gta aag ggc tat tct ttt ata aaa gat cta caa tgg     1023
Leu Ser Gln Asp Val Lys Gly Tyr Ser Phe Ile Lys Asp Leu Gln Trp
            305                 310                 315 att caa gta tct gat tcc aaa gaa gcc tat aga ctt tta aaa cta gga     1071
Ile Gln Val Ser Asp Ser Lys Glu Ala Tyr Arg Leu Leu Lys Leu Gly
        320                 325                 330 ata aag cac cag agt gtt gcc ttc aca aaa ttg aat aat gct tcc agt     1119
Ile Lys His Gln Ser Val Ala Phe Thr Lys Leu Asn Asn Ala Ser Ser
    335                 340                 345 aga agt cac agc ata ttc act gtt aaa ata tta cag att gaa gat tct     1167
Arg Ser His Ser Ile Phe Thr Val Lys Ile Leu Gln Ile Glu Asp Ser
350                 355                 360                 365 gaa atg tct cgt gta att cga gtc agt gaa tta tct tta tgt gat ctt     1215
Glu Met Ser Arg Val Ile Arg Val Ser Glu Leu Ser Leu Cys Asp Leu
                370                 375                 380 gct ggt tca gaa cga act atg aag aca cag aat gaa ggt gaa agg tta     1263
Ala Gly Ser Glu Arg Thr Met Lys Thr Gln Asn Glu Gly Glu Arg Leu
                385                 390                 395 aga gag act ggg aat atc aac act tct tta ttg act ctg gga aag tgt     1311
Arg Glu Thr Gly Asn Ile Asn Thr Ser Leu Leu Thr Leu Gly Lys Cys
            400                 405                 410 att aac gtc ttg aag aat agt gaa aag tca aag ttt caa cag cat gtg     1359
Ile Asn Val Leu Lys Asn Ser Glu Lys Ser Lys Phe Gln Gln His Val
        415                 420                 425 cct ttc cgg gaa agt aaa ctg act cac tat ttt caa agt ttt ttt aat     1407
Pro Phe Arg Glu Ser Lys Leu Thr His Tyr Phe Gln Ser Phe Phe Asn
    430                 435                 440                 445 ggt aaa ggg aaa att tgt atg att gtc aat atc agc caa tgt tat tta     1455
Gly Lys Gly Lys Ile Cys Met Ile Val Asn Ile Ser Gln Cys Tyr Leu
                450                 455                 460 gcc tat gat gaa aca ctc aat gta ttg aag ttc tcc gcc att gca caa     1503
Ala Tyr Asp Glu Thr Leu Asn Val Leu Lys Phe Ser Ala Ile Ala Gln
                465                 470                 475 aaa gtt tgt gtc cca gac act tta aat tcc tct caa gag aaa tta ttt     1551
Lys Val Cys Val Pro Asp Thr Leu Asn Ser Ser Gln Glu Lys Leu Phe
            480                 485                 490 gga cct gtc aaa tct tct caa gat gta tca cta gac agt aat tca aac     1599
Gly Pro Val Lys Ser Ser Gln Asp Val Ser Leu Asp Ser Asn Ser Asn
        495                 500                 505 agt aaa ata tta aat gta aaa aga gcc acc att tca tgg gaa aat agt     1647
Ser Lys Ile Leu Asn Val Lys Arg Ala Thr Ile Ser Trp Glu Asn Ser
510                 515                 520                 525 cta gaa gat ttg atg gaa gac gag gat ttg gtt gag gag cta gaa aac     1695
Leu Glu Asp Leu Met Glu Asp Glu Asp Leu Val Glu Glu Leu Glu Asn
                530                 535                 540 gct gaa gaa act caa aat gtg gaa act aaa ctt ctt gat gaa gat cta     1743
Ala Glu Glu Thr Gln Asn Val Glu Thr Lys Leu Leu Asp Glu Asp Leu
                545                 550                 555 gat aaa aca tta gag gaa aat aag gct ttc att agc cac gag gag aaa     1791
Asp Lys Thr Leu Glu Glu Asn Lys Ala Phe Ile Ser His Glu Glu Lys
            560                 565                 570 aga aaa ctg ttg gac tta ata gaa gac ttg aaa aaa aaa ctg ata aat     1839
```

```
Arg Lys Leu Leu Asp Leu Ile Glu Asp Leu Lys Lys Leu Ile Asn
    575             580             585 gaa aaa aag gaa aaa tta acc ttg gaa ttt aaa att cga gaa gaa gtt    1887
Glu Lys Lys Glu Lys Leu Thr Leu Glu Phe Lys Ile Arg Glu Glu Val
590             595             600             605 aca cag gag ttt act cag tat tgg gct caa cgg gaa gct gac ttt aag    1935
Thr Gln Glu Phe Thr Gln Tyr Trp Ala Gln Arg Glu Ala Asp Phe Lys
                610             615             620 gag act ctg ctt caa gaa cga gag ata tta gaa gaa aat gct gaa cgt    1983
Glu Thr Leu Leu Gln Glu Arg Glu Ile Leu Glu Glu Asn Ala Glu Arg
            625             630             635 cgt ttg gct atc ttc aag gat ttg gtt ggt aaa tgt gac act cga gaa    2031
Arg Leu Ala Ile Phe Lys Asp Leu Val Gly Lys Cys Asp Thr Arg Glu
        640             645             650 gaa gca gcg aaa gac att tgt gcc aca aaa gtt gaa act gaa gaa gct    2079
Glu Ala Ala Lys Asp Ile Cys Ala Thr Lys Val Glu Thr Glu Glu Ala
    655             660             665 act gct tgt tta gaa cta aag ttt aat caa att aaa gct gaa tta gct    2127
Thr Ala Cys Leu Glu Leu Lys Phe Asn Gln Ile Lys Ala Glu Leu Ala
670             675             680             685 aaa acc aaa gga gaa tta atc aaa acc aaa gaa gag tta aaa aag aga    2175
Lys Thr Lys Gly Glu Leu Ile Lys Thr Lys Glu Glu Leu Lys Lys Arg
                690             695             700 gaa aat gaa tca gat tca ttg att caa gag ctt gag aca tct aat aag    2223
Glu Asn Glu Ser Asp Ser Leu Ile Gln Glu Leu Glu Thr Ser Asn Lys
            705             710             715 aaa ata att aca cag aat caa aga att aaa gaa ttg ata aat ata att    2271
Lys Ile Ile Thr Gln Asn Gln Arg Ile Lys Glu Leu Ile Asn Ile Ile
        720             725             730 gat caa aaa gaa gat act atc aac gaa ttt cag aac cta aag tct cat    2319
Asp Gln Lys Glu Asp Thr Ile Asn Glu Phe Gln Asn Leu Lys Ser His
    735             740             745 atg gaa aac aca ttt aaa tgc aat gac aag gct gat aca tct tct tta    2367
Met Glu Asn Thr Phe Lys Cys Asn Asp Lys Ala Asp Thr Ser Ser Leu
750             755             760             765 ata ata aac aat aaa ttg att tgt aat gaa aca gtt gaa gta cct aag    2415
Ile Ile Asn Asn Lys Leu Ile Cys Asn Glu Thr Val Glu Val Pro Lys
                770             775             780 gac agc aaa tct aaa atc tgt tca gaa aga aaa aga gta aat gaa aat    2463
Asp Ser Lys Ser Lys Ile Cys Ser Glu Arg Lys Arg Val Asn Glu Asn
            785             790             795 gaa ctt cag caa gat gaa cca cca gca aag aaa ggg tct atc cat gtt    2511
Glu Leu Gln Gln Asp Glu Pro Pro Ala Lys Lys Gly Ser Ile His Val
        800             805             810 agt tca gct atc act gaa gac caa aag aaa agt gaa gaa gtg cga ccg    2559
Ser Ser Ala Ile Thr Glu Asp Gln Lys Lys Ser Glu Glu Val Arg Pro
    815             820             825 aac att gca gaa att gaa gac atc aga gtt tta caa gaa aat aat gaa    2607
Asn Ile Ala Glu Ile Glu Asp Ile Arg Val Leu Gln Glu Asn Asn Glu
830             835             840             845 gga ctg aga gca ttt tta ctc act att gag aat gaa ctt aaa aat gaa    2655
Gly Leu Arg Ala Phe Leu Leu Thr Ile Glu Asn Glu Leu Lys Asn Glu
                850             855             860 aag gaa gaa aaa gca gaa tta aat aaa cag att gtt cat ttt cag cag    2703
Lys Glu Glu Lys Ala Glu Leu Asn Lys Gln Ile Val His Phe Gln Gln
            865             870             875 gaa ctt tct ctt tct gaa aaa aag aat tta act tta agt aaa gag gtc    2751
Glu Leu Ser Leu Ser Glu Lys Lys Asn Leu Thr Leu Ser Lys Glu Val
        880             885             890
```

| | | |
|---|---|---|
| caa caa att cag tca aat tat gat att gca att gct gaa tta cat gtg<br>Gln Gln Ile Gln Ser Asn Tyr Asp Ile Ala Ile Ala Glu Leu His Val<br>     895                             900                      905 | | 2799 |
| cag aaa agt aaa aat caa gaa cag gag gaa aag atc atg aaa ttg tca<br>Gln Lys Ser Lys Asn Gln Glu Gln Glu Glu Lys Ile Met Lys Leu Ser<br>910                         915                      920                   925 | | 2847 |
| aat gag ata gaa act gct aca aga agc att aca aat aat gtt tca caa<br>Asn Glu Ile Glu Thr Ala Thr Arg Ser Ile Thr Asn Asn Val Ser Gln<br>                      930                      935                      940 | | 2895 |
| ata aaa tta atg cac acg aaa ata gac gaa cta cgt act ctt gat tca<br>Ile Lys Leu Met His Thr Lys Ile Asp Glu Leu Arg Thr Leu Asp Ser<br>             945                      950                      955 | | 2943 |
| gtt tct cag att tca aac ata gat ttg ctc aat ctc agg gat ctg tca<br>Val Ser Gln Ile Ser Asn Ile Asp Leu Leu Asn Leu Arg Asp Leu Ser<br>     960                            965                      970 | | 2991 |
| aat ggt tct gag gag gat aat ttg cca aat aca cag tta gac ctt tta<br>Asn Gly Ser Glu Glu Asp Asn Leu Pro Asn Thr Gln Leu Asp Leu Leu<br>975                       980                      985 | | 3039 |
| ggt aat gat tat ttg gta agt aag caa gtt aaa gaa tat cga att caa<br>Gly Asn Asp Tyr Leu Val Ser Lys Gln Val Lys Glu Tyr Arg Ile Gln<br>990                       995                     1000                1005 | | 3087 |
| gaa ccc aat agg gaa aat tct ttc cac tct agt att gaa gct att<br>Glu Pro Asn Arg Glu Asn Ser Phe His Ser Ser Ile Glu Ala Ile<br>               1010                    1015                1020 | | 3132 |
| tgg gaa gaa tgt aaa gag att gtg aag gcc tct tcc aaa aaa agt<br>Trp Glu Glu Cys Lys Glu Ile Val Lys Ala Ser Ser Lys Lys Ser<br>               1025                    1030                1035 | | 3177 |
| cat cag att gag gaa ctg gaa caa caa att gaa aaa ttg cag gca<br>His Gln Ile Glu Glu Leu Glu Gln Gln Ile Glu Lys Leu Gln Ala<br>               1040                    1045                1050 | | 3222 |
| gaa gta aaa ggc tat aag gat gaa aac aat aga cta aag gag aag<br>Glu Val Lys Gly Tyr Lys Asp Glu Asn Asn Arg Leu Lys Glu Lys<br>               1055                    1060                1065 | | 3267 |
| gag cat aaa aac caa gat gac cta cta aaa gaa aaa gaa act ctt<br>Glu His Lys Asn Gln Asp Asp Leu Leu Lys Glu Lys Glu Thr Leu<br>               1070                    1075                1080 | | 3312 |
| ata cag cag ctg aaa gaa gaa ttg caa gaa aaa aat gtt act ctt<br>Ile Gln Gln Leu Lys Glu Glu Leu Gln Glu Lys Asn Val Thr Leu<br>               1085                    1090                1095 | | 3357 |
| gat gtt caa ata cag cat gta gtt gaa gga aag aga gcg ctt tca<br>Asp Val Gln Ile Gln His Val Val Glu Gly Lys Arg Ala Leu Ser<br>               1100                    1105                1110 | | 3402 |
| gaa ctt aca caa ggt gtt act tgc tat aag gca aaa ata aag gaa<br>Glu Leu Thr Gln Gly Val Thr Cys Tyr Lys Ala Lys Ile Lys Glu<br>               1115                    1120                1125 | | 3447 |
| ctt gaa aca att tta gag act cag aaa gtt gaa tgt agt cat tca<br>Leu Glu Thr Ile Leu Glu Thr Gln Lys Val Glu Cys Ser His Ser<br>               1130                    1135                1140 | | 3492 |
| gcc aag tta gaa caa gac att ttg gaa aag gaa tct atc atc tta<br>Ala Lys Leu Glu Gln Asp Ile Leu Glu Lys Glu Ser Ile Ile Leu<br>               1145                    1150                1155 | | 3537 |
| aag cta gaa aga aat ttg aag gaa ttt caa gaa cat ctt cag gat<br>Lys Leu Glu Arg Asn Leu Lys Glu Phe Gln Glu His Leu Gln Asp<br>               1160                    1165                1170 | | 3582 |
| tct gtc aaa aac acc aaa gat tta aat gta aag gaa ctc aag ctg<br>Ser Val Lys Asn Thr Lys Asp Leu Asn Val Lys Glu Leu Lys Leu<br>               1175                    1180                1185 | | 3627 |
| aaa gaa gaa atc aca cag tta aca aat aat ttg caa gat atg aaa<br>Lys Glu Glu Ile Thr Gln Leu Thr Asn Asn Leu Gln Asp Met Lys<br>               1190                    1195                1200 | | 3672 |

```
cat tta ctt caa tta  aaa gaa gaa gaa  gaa acc aac agg caa                    3717
His Leu Leu Gln Leu  Lys Glu Glu Glu  Glu Thr Asn Arg Gln
            1205                 1210                 1215 gaa aca gaa aaa ttg  aaa gag gaa ctc  tct gca agc tct gct cgt                3762
Glu Thr Glu Lys Leu  Lys Glu Glu Leu  Ser Ala Ser Ser Ala Arg
            1220                 1225                 1230 acc cag aat ctg aaa  gca gat ctt cag  agg aag gaa gaa gat tat                3807
Thr Gln Asn Leu Lys  Ala Asp Leu Gln  Arg Lys Glu Glu Asp Tyr
            1235                 1240                 1245 gct gac ctg aaa gag  aaa ctg act gat  gcc aaa aag cag att aag                3852
Ala Asp Leu Lys Glu  Lys Leu Thr Asp  Ala Lys Lys Gln Ile Lys
            1250                 1255                 1260 caa gta cag aaa gag  gta tct gta atg  cgt gat gag gat aaa tta                3897
Gln Val Gln Lys Glu  Val Ser Val Met  Arg Asp Glu Asp Lys Leu
            1265                 1270                 1275 ctg agg att aaa att  aat gaa ctg gag  aaa aag aaa aac cag tgt                3942
Leu Arg Ile Lys Ile  Asn Glu Leu Glu  Lys Lys Lys Asn Gln Cys
            1280                 1285                 1290 tct cag gaa tta gat  atg aaa cag cga  acc att cag caa ctc aag                3987
Ser Gln Glu Leu Asp  Met Lys Gln Arg  Thr Ile Gln Gln Leu Lys
            1295                 1300                 1305 gag cag tta aat aat  cag aaa gtg gaa  gaa gct ata caa cag tat                4032
Glu Gln Leu Asn Asn  Gln Lys Val Glu  Glu Ala Ile Gln Gln Tyr
            1310                 1315                 1320 gag aga gca tgc aaa  gat cta aat gtt  aaa gag aaa ata att gaa                4077
Glu Arg Ala Cys Lys  Asp Leu Asn Val  Lys Glu Lys Ile Ile Glu
            1325                 1330                 1335 gac atg cga atg aca  cta gaa gaa cag  gaa caa act cag gta gaa                4122
Asp Met Arg Met Thr  Leu Glu Glu Gln  Glu Gln Thr Gln Val Glu
            1340                 1345                 1350 cag gat caa gtg ctt  gag gct aaa tta  gag gaa gtt gaa agg ctg                4167
Gln Asp Gln Val Leu  Glu Ala Lys Leu  Glu Glu Val Glu Arg Leu
            1355                 1360                 1365 gcc aca gaa ttg gaa  aaa tgg aag gaa  aaa tgc aat gat ttg gaa                4212
Ala Thr Glu Leu Glu  Lys Trp Lys Glu  Lys Cys Asn Asp Leu Glu
            1370                 1375                 1380 acc aaa aac aat caa  agg tca aat aaa  gaa cat gag aac aac aca                4257
Thr Lys Asn Asn Gln  Arg Ser Asn Lys  Glu His Glu Asn Asn Thr
            1385                 1390                 1395 gat gtg ctt gga aag  ctc act aat ctt  caa gat gag tta cag gag                4302
Asp Val Leu Gly Lys  Leu Thr Asn Leu  Gln Asp Glu Leu Gln Glu
            1400                 1405                 1410 tct gaa cag aaa tat  aat gct gat aga  aag aaa tgg tta gaa gaa                4347
Ser Glu Gln Lys Tyr  Asn Ala Asp Arg  Lys Lys Trp Leu Glu Glu
            1415                 1420                 1425 aaa atg atg ctt atc  act caa gcg aaa  gaa gca gag aat ata cga                4392
Lys Met Met Leu Ile  Thr Gln Ala Lys  Glu Ala Glu Asn Ile Arg
            1430                 1435                 1440 aat aaa gag atg aaa  aaa tat gct gag  gac agg gag cgt ttt ttt                4437
Asn Lys Glu Met Lys  Lys Tyr Ala Glu  Asp Arg Glu Arg Phe Phe
            1445                 1450                 1455 aag caa cag aat gaa  atg gaa ata ctg  aca gcc cag ctg aca gag                4482
Lys Gln Gln Asn Glu  Met Glu Ile Leu  Thr Ala Gln Leu Thr Glu
            1460                 1465                 1470 aaa gat agt gac ctt  caa aag tgg cga  gaa gaa cga gat caa ctg                4527
Lys Asp Ser Asp Leu  Gln Lys Trp Arg  Glu Glu Arg Asp Gln Leu
            1475                 1480                 1485 gtt gca gct tta gaa  ata cag cta aaa  gca ctg ata tcc agt aat                4572
Val Ala Ala Leu Glu  Ile Gln Leu Lys  Ala Leu Ile Ser Ser Asn
```

|     |     |     |     |     |     |     |     |     |     |     |     |     |     |     |      |
|---|---|---|---|---|---|---|---|---|---|---|---|---|---|---|---|
|     |     |     |     | 1490 |     |     |     |     | 1495 |     |     |     |     | 1500 |      |
| gta | cag | aaa | gat | aat | gaa | att | gaa | caa | cta | aaa | agg | atc | ata | tca | 4617 |
| Val | Gln | Lys | Asp | Asn | Glu | Ile | Glu | Gln | Leu | Lys | Arg | Ile | Ile | Ser |      |
|     |     |     |     | 1505 |     |     |     |     | 1510 |     |     |     |     | 1515 |      |
| gag | act | tct | aaa | ata | gaa | aca | caa | atc | atg | gat | atc | aag | ccc | aaa | 4662 |
| Glu | Thr | Ser | Lys | Ile | Glu | Thr | Gln | Ile | Met | Asp | Ile | Lys | Pro | Lys |      |
|     |     |     |     | 1520 |     |     |     |     | 1525 |     |     |     |     | 1530 |      |
| cgt | att | agt | tca | gca | gat | cct | gac | aaa | ctt | caa | act | gaa | cct | cta | 4707 |
| Arg | Ile | Ser | Ser | Ala | Asp | Pro | Asp | Lys | Leu | Gln | Thr | Glu | Pro | Leu |      |
|     |     |     |     | 1535 |     |     |     |     | 1540 |     |     |     |     | 1545 |      |
| tcg | aca | agt | ttt | gaa | att | tcc | aga | aat | aaa | ata | gag | gat | gga | tct | 4752 |
| Ser | Thr | Ser | Phe | Glu | Ile | Ser | Arg | Asn | Lys | Ile | Glu | Asp | Gly | Ser |      |
|     |     |     |     | 1550 |     |     |     |     | 1555 |     |     |     |     | 1560 |      |
| gta | gtc | ctt | gac | tct | tgt | gaa | gtg | tca | aca | gaa | aat | gat | caa | agc | 4797 |
| Val | Val | Leu | Asp | Ser | Cys | Glu | Val | Ser | Thr | Glu | Asn | Asp | Gln | Ser |      |
|     |     |     |     | 1565 |     |     |     |     | 1570 |     |     |     |     | 1575 |      |
| act | cga | ttt | cca | aaa | cct | gag | tta | gag | att | caa | ttt | aca | cct | tta | 4842 |
| Thr | Arg | Phe | Pro | Lys | Pro | Glu | Leu | Glu | Ile | Gln | Phe | Thr | Pro | Leu |      |
|     |     |     |     | 1580 |     |     |     |     | 1585 |     |     |     |     | 1590 |      |
| cag | cca | aac | aaa | atg | gca | gtg | aaa | cac | cct | ggt | tgt | acc | aca | cca | 4887 |
| Gln | Pro | Asn | Lys | Met | Ala | Val | Lys | His | Pro | Gly | Cys | Thr | Thr | Pro |      |
|     |     |     |     | 1595 |     |     |     |     | 1600 |     |     |     |     | 1605 |      |
| gtg | aca | gtt | aag | att | ccc | aag | gct | cgg | aag | agg | aag | agt | aat | gaa | 4932 |
| Val | Thr | Val | Lys | Ile | Pro | Lys | Ala | Arg | Lys | Arg | Lys | Ser | Asn | Glu |      |
|     |     |     |     | 1610 |     |     |     |     | 1615 |     |     |     |     | 1620 |      |
| atg | gag | gag | gac | ttg | gtg | aaa | tgt | gaa | aat | aag | aag | aat | gct | aca | 4977 |
| Met | Glu | Glu | Asp | Leu | Val | Lys | Cys | Glu | Asn | Lys | Lys | Asn | Ala | Thr |      |
|     |     |     |     | 1625 |     |     |     |     | 1630 |     |     |     |     | 1635 |      |
| ccc | aga | act | aat | ttg | aaa | ttt | cct | att | tca | gat | gat | aga | aat | tct | 5022 |
| Pro | Arg | Thr | Asn | Leu | Lys | Phe | Pro | Ile | Ser | Asp | Asp | Arg | Asn | Ser |      |
|     |     |     |     | 1640 |     |     |     |     | 1645 |     |     |     |     | 1650 |      |
| tct | gtc | aaa | aag | gaa | caa | aag | gtt | gcc | ata | cgt | cca | tca | tct | aag | 5067 |
| Ser | Val | Lys | Lys | Glu | Gln | Lys | Val | Ala | Ile | Arg | Pro | Ser | Ser | Lys |      |
|     |     |     |     | 1655 |     |     |     |     | 1660 |     |     |     |     | 1665 |      |
| aaa | aca | tat | tct | tta | cgg | agt | cag | gca | tcc | ata | att | ggt | gta | aac | 5112 |
| Lys | Thr | Tyr | Ser | Leu | Arg | Ser | Gln | Ala | Ser | Ile | Ile | Gly | Val | Asn |      |
|     |     |     |     | 1670 |     |     |     |     | 1675 |     |     |     |     | 1680 |      |
| ctg | gcc | act | aag | aaa | aaa | gaa | gga | aca | cta | cag | aaa | ttt | gga | gac | 5157 |
| Leu | Ala | Thr | Lys | Lys | Lys | Glu | Gly | Thr | Leu | Gln | Lys | Phe | Gly | Asp |      |
|     |     |     |     | 1685 |     |     |     |     | 1690 |     |     |     |     | 1695 |      |
| ttc | tta | caa | cat | tct | ccc | tca | att | ctt | caa | tca | aaa | gca | aag | aag | 5202 |
| Phe | Leu | Gln | His | Ser | Pro | Ser | Ile | Leu | Gln | Ser | Lys | Ala | Lys | Lys |      |
|     |     |     |     | 1700 |     |     |     |     | 1705 |     |     |     |     | 1710 |      |
| ata | att | gaa | aca | atg | agc | tct | tca | aag | ctc | tca | aat | gta | gaa | gca | 5247 |
| Ile | Ile | Glu | Thr | Met | Ser | Ser | Ser | Lys | Leu | Ser | Asn | Val | Glu | Ala |      |
|     |     |     |     | 1715 |     |     |     |     | 1720 |     |     |     |     | 1725 |      |
| agt | aaa | gaa | aat | gtg | tct | caa | cca | aaa | cga | gcc | aaa | cgg | aaa | tta | 5292 |
| Ser | Lys | Glu | Asn | Val | Ser | Gln | Pro | Lys | Arg | Ala | Lys | Arg | Lys | Leu |      |
|     |     |     |     | 1730 |     |     |     |     | 1735 |     |     |     |     | 1740 |      |
| tac | aca | agt | gaa | att | tca | tct | cct | att | gat | ata | tca | ggc | caa | gtg | 5337 |
| Tyr | Thr | Ser | Glu | Ile | Ser | Ser | Pro | Ile | Asp | Ile | Ser | Gly | Gln | Val |      |
|     |     |     |     | 1745 |     |     |     |     | 1750 |     |     |     |     | 1755 |      |
| att | tta | atg | gac | cag | aaa | atg | aag | gag | agt | gat | cac | cag | att | atc | 5382 |
| Ile | Leu | Met | Asp | Gln | Lys | Met | Lys | Glu | Ser | Asp | His | Gln | Ile | Ile |      |
|     |     |     |     | 1760 |     |     |     |     | 1765 |     |     |     |     | 1770 |      |
| aaa | cga | cga | ctt | cga | aca | aaa | aca | gcc | aaa | taa | atcacttatg |  |  |  | 5425 |
| Lys | Arg | Arg | Leu | Arg | Thr | Lys | Thr | Ala | Lys |     |     |     |     |     |      |
|     |     |     |     | 1775 |     |     |     |     | 1780 |     |     |     |     |     |      | gaaatgttta atataaattt tatagtcata gtcattggaa cttgcatcct gtattgtaaa  5485

-continued

```
tataaatgta tatattatgc attaaatcac tctgcatata gattgctgtt ttatacatag    5545
tataatttta attcaataaa tgagtcaaaa tttgtatatt tttataaggc tttttttataa   5605 tagcttcttt caaactgtat ttccctatta tctcagacat tggatcagtg aagatcctag    5665
gaaagaggct gttattctca tttattttgc tatacaggat gtaataggtc aggtatttgg    5725
tttacttata tttaacaatg tcttatgaat ttttttttact ttatctgtta tacaactgat   5785
tttacatatc tgtttggatt atagctagga tttggagaat aagtgtgtac agatcacaaa    5845
acatgtatat acattattta gaaaagatct caagtcttta attagaatgt ctcacttatt    5905
ttgtaaacat tttgtgggta catagtacat gtatatattt acggggtatg tgagatgttt    5965
tgacacaggc atgcaatgtg aaatacgtgt atcatggaga atgaggtatc catcccctca    6025 agcattttc ctttgaatta cagataatcc aattacattc tttagatcat ttaaaaatat     6085
acaagtaagt tattattgat tatagtcact ctattgtgct atcagatagt agatcattct    6145
ttttatctta tttgtttttg tacccattaa ccatccccac ctcccctgc aaccgtcagt    6205 accccttacca gccactggta accattcttc tactctgtat gcccatgagg tcaattgatt    6265
ttatttttag atcccataaa taaatgagaa catgcagtct ttgtcaaaaa aaaa          6319
```

<210> SEQ ID NO 126
<211> LENGTH: 1780
<212> TYPE: PRT
<213> ORGANISM: Homo sapiens

<400> SEQUENCE: 126

```
Met Glu Ser Asn Phe Asn Gln Glu Gly Val Pro Arg Pro Ser Tyr Val
1               5                   10                  15

Phe Ser Ala Asp Pro Ile Ala Arg Pro Ser Glu Ile Asn Phe Asp Gly
            20                  25                  30

Ile Lys Leu Asp Leu Ser His Glu Phe Ser Leu Val Ala Pro Asn Thr
        35                  40                  45

Glu Ala Asn Ser Phe Glu Ser Lys Asp Tyr Leu Gln Val Cys Leu Arg
    50                  55                  60

Ile Arg Pro Phe Thr Gln Ser Glu Lys Glu Leu Glu Ser Glu Gly Cys
65                  70                  75                  80

Val His Ile Leu Asp Ser Gln Thr Val Val Leu Lys Glu Pro Gln Cys
                85                  90                  95

Ile Leu Gly Arg Leu Ser Glu Lys Ser Ser Gly Gln Met Ala Gln Lys
            100                 105                 110

Phe Ser Phe Ser Lys Val Phe Gly Pro Ala Thr Thr Gln Lys Glu Phe
        115                 120                 125

Phe Gln Gly Cys Ile Met Gln Pro Val Lys Asp Leu Leu Lys Gly Gln
    130                 135                 140

Ser Arg Leu Ile Phe Thr Tyr Gly Leu Thr Asn Ser Gly Lys Thr Tyr
145                 150                 155                 160

Thr Phe Gln Gly Thr Glu Glu Asn Ile Gly Ile Leu Pro Arg Thr Leu
                165                 170                 175

Asn Val Leu Phe Asp Ser Leu Gln Glu Arg Leu Tyr Thr Lys Met Asn
            180                 185                 190

Leu Lys Pro His Arg Ser Arg Glu Tyr Leu Arg Leu Ser Ser Glu Gln
        195                 200                 205

Glu Lys Glu Glu Ile Ala Ser Lys Ser Ala Leu Leu Arg Gln Ile Lys
    210                 215                 220
```

-continued

Glu Val Thr Val His Asn Asp Ser Asp Asp Thr Leu Tyr Gly Ser Leu
225                 230                 235                 240

Thr Asn Ser Leu Asn Ile Ser Glu Phe Glu Ser Ile Lys Asp Tyr
            245                 250                 255

Glu Gln Ala Asn Leu Asn Met Ala Asn Ser Ile Lys Phe Ser Val Trp
        260                 265                 270

Val Ser Phe Phe Glu Ile Tyr Asn Glu Tyr Ile Tyr Asp Leu Phe Val
    275                 280                 285

Pro Val Ser Ser Lys Phe Gln Lys Arg Lys Met Leu Arg Leu Ser Gln
290                 295                 300

Asp Val Lys Gly Tyr Ser Phe Ile Lys Asp Leu Gln Trp Ile Gln Val
305                 310                 315                 320

Ser Asp Ser Lys Glu Ala Tyr Arg Leu Leu Lys Leu Gly Ile Lys His
                325                 330                 335

Gln Ser Val Ala Phe Thr Lys Leu Asn Asn Ala Ser Ser Arg Ser His
            340                 345                 350

Ser Ile Phe Thr Val Lys Ile Leu Gln Ile Glu Asp Ser Glu Met Ser
        355                 360                 365

Arg Val Ile Arg Val Ser Glu Leu Ser Leu Cys Asp Leu Ala Gly Ser
370                 375                 380

Glu Arg Thr Met Lys Thr Gln Asn Glu Gly Glu Arg Leu Arg Glu Thr
385                 390                 395                 400

Gly Asn Ile Asn Thr Ser Leu Leu Thr Leu Gly Lys Cys Ile Asn Val
                405                 410                 415

Leu Lys Asn Ser Glu Lys Ser Lys Phe Gln Gln His Val Pro Phe Arg
            420                 425                 430

Glu Ser Lys Leu Thr His Tyr Phe Gln Ser Phe Phe Asn Gly Lys Gly
        435                 440                 445

Lys Ile Cys Met Ile Val Asn Ile Ser Gln Cys Tyr Leu Ala Tyr Asp
    450                 455                 460

Glu Thr Leu Asn Val Leu Lys Phe Ser Ala Ile Ala Gln Lys Val Cys
465                 470                 475                 480

Val Pro Asp Thr Leu Asn Ser Ser Gln Glu Lys Leu Phe Gly Pro Val
                485                 490                 495

Lys Ser Ser Gln Asp Val Ser Leu Asp Ser Asn Ser Asn Ser Lys Ile
            500                 505                 510

Leu Asn Val Lys Arg Ala Thr Ile Ser Trp Glu Asn Ser Leu Glu Asp
        515                 520                 525

Leu Met Glu Asp Glu Asp Leu Val Glu Glu Leu Glu Asn Ala Glu Glu
    530                 535                 540

Thr Gln Asn Val Glu Thr Lys Leu Leu Asp Glu Asp Leu Asp Lys Thr
545                 550                 555                 560

Leu Glu Glu Asn Lys Ala Phe Ile Ser His Glu Glu Lys Arg Lys Leu
                565                 570                 575

Leu Asp Leu Ile Glu Asp Leu Lys Lys Lys Leu Ile Asn Glu Lys Lys
            580                 585                 590

Glu Lys Leu Thr Leu Glu Phe Lys Ile Arg Glu Glu Val Thr Gln Glu
        595                 600                 605

Phe Thr Gln Tyr Trp Ala Gln Arg Glu Ala Asp Phe Lys Glu Thr Leu
    610                 615                 620

Leu Gln Glu Arg Glu Ile Leu Glu Glu Asn Ala Glu Arg Arg Leu Ala
625                 630                 635                 640

Ile Phe Lys Asp Leu Val Gly Lys Cys Asp Thr Arg Glu Glu Ala Ala

-continued

```
                645                 650                 655
Lys Asp Ile Cys Ala Thr Lys Val Glu Thr Glu Glu Ala Thr Ala Cys
            660                 665                 670

Leu Glu Leu Lys Phe Asn Gln Ile Lys Ala Glu Leu Ala Lys Thr Lys
            675                 680                 685

Gly Glu Leu Ile Lys Thr Lys Glu Glu Leu Lys Lys Arg Glu Asn Glu
            690                 695                 700

Ser Asp Ser Leu Ile Gln Glu Leu Glu Thr Ser Asn Lys Lys Ile Ile
705                 710                 715                 720

Thr Gln Asn Gln Arg Ile Lys Glu Leu Ile Asn Ile Asp Gln Lys
                725                 730                 735

Glu Asp Thr Ile Asn Glu Phe Gln Asn Leu Lys Ser His Met Glu Asn
            740                 745                 750

Thr Phe Lys Cys Asn Asp Lys Ala Asp Thr Ser Ser Leu Ile Ile Asn
                755                 760                 765

Asn Lys Leu Ile Cys Asn Glu Thr Val Glu Val Pro Lys Asp Ser Lys
770                 775                 780

Ser Lys Ile Cys Ser Glu Arg Lys Arg Val Asn Glu Asn Glu Leu Gln
785                 790                 795                 800

Gln Asp Glu Pro Pro Ala Lys Lys Gly Ser Ile His Val Ser Ser Ala
                805                 810                 815

Ile Thr Glu Asp Gln Lys Lys Ser Glu Glu Val Arg Pro Asn Ile Ala
            820                 825                 830

Glu Ile Glu Asp Ile Arg Val Leu Gln Glu Asn Asn Glu Gly Leu Arg
            835                 840                 845

Ala Phe Leu Leu Thr Ile Glu Asn Glu Leu Lys Asn Glu Lys Glu Glu
850                 855                 860

Lys Ala Glu Leu Asn Lys Gln Ile Val His Phe Gln Gln Glu Leu Ser
865                 870                 875                 880

Leu Ser Glu Lys Lys Asn Leu Thr Leu Ser Lys Glu Val Gln Gln Ile
                885                 890                 895

Gln Ser Asn Tyr Asp Ile Ala Ile Ala Glu Leu His Val Gln Lys Ser
            900                 905                 910

Lys Asn Gln Glu Gln Glu Glu Lys Ile Met Lys Leu Ser Asn Glu Ile
            915                 920                 925

Glu Thr Ala Thr Arg Ser Ile Thr Asn Asn Val Ser Gln Ile Lys Leu
            930                 935                 940

Met His Thr Lys Ile Asp Glu Leu Arg Thr Leu Asp Ser Val Ser Gln
945                 950                 955                 960

Ile Ser Asn Ile Asp Leu Leu Asn Leu Arg Asp Leu Ser Asn Gly Ser
                965                 970                 975

Glu Glu Asp Asn Leu Pro Asn Thr Gln Leu Asp Leu Leu Gly Asn Asp
            980                 985                 990

Tyr Leu Val Ser Lys Gln Val Lys  Glu Tyr Arg Ile Gln  Glu Pro Asn
                995                 1000                1005

Arg Glu  Asn Ser Phe His Ser  Ser Ile Glu Ala Ile  Trp Glu Glu
            1010                1015                1020

Cys Lys  Glu Ile Val Lys Ala  Ser Ser Lys Ser  His Gln Ile
        1025                1030                1035

Glu Glu  Leu Glu Gln Gln Ile  Glu Lys Leu Gln Ala  Glu Val Lys
            1040                1045                1050

Gly Tyr  Lys Asp Glu Asn Asn  Arg Leu Lys Glu Lys  Glu His Lys
        1055                1060                1065
```

```
Asn Gln Asp Asp Leu Leu Lys Glu Lys Glu Thr Leu Ile Gln Gln
    1070                1075                1080

Leu Lys Glu Glu Leu Gln Glu Lys Asn Val Thr Leu Asp Val Gln
    1085                1090                1095

Ile Gln His Val Val Glu Gly Lys Arg Ala Leu Ser Glu Leu Thr
    1100                1105                1110

Gln Gly Val Thr Cys Tyr Lys Ala Lys Ile Lys Glu Leu Glu Thr
    1115                1120                1125

Ile Leu Glu Thr Gln Lys Val Glu Cys Ser His Ser Ala Lys Leu
    1130                1135                1140

Glu Gln Asp Ile Leu Glu Lys Glu Ser Ile Ile Leu Lys Leu Glu
    1145                1150                1155

Arg Asn Leu Lys Glu Phe Gln Glu His Leu Gln Asp Ser Val Lys
    1160                1165                1170

Asn Thr Lys Asp Leu Asn Val Lys Glu Leu Lys Leu Lys Glu Glu
    1175                1180                1185

Ile Thr Gln Leu Thr Asn Asn Leu Gln Asp Met Lys His Leu Leu
    1190                1195                1200

Gln Leu Lys Glu Glu Glu Glu Glu Thr Asn Arg Gln Glu Thr Glu
    1205                1210                1215

Lys Leu Lys Glu Glu Leu Ser Ala Ser Ser Ala Arg Thr Gln Asn
    1220                1225                1230

Leu Lys Ala Asp Leu Gln Arg Lys Glu Glu Asp Tyr Ala Asp Leu
    1235                1240                1245

Lys Glu Lys Leu Thr Asp Ala Lys Lys Gln Ile Lys Gln Val Gln
    1250                1255                1260

Lys Glu Val Ser Val Met Arg Asp Glu Asp Lys Leu Leu Arg Ile
    1265                1270                1275

Lys Ile Asn Glu Leu Glu Lys Lys Lys Asn Gln Cys Ser Gln Glu
    1280                1285                1290

Leu Asp Met Lys Gln Arg Thr Ile Gln Gln Leu Lys Glu Gln Leu
    1295                1300                1305

Asn Asn Gln Lys Val Glu Glu Ala Ile Gln Gln Tyr Glu Arg Ala
    1310                1315                1320

Cys Lys Asp Leu Asn Val Lys Glu Lys Ile Ile Glu Asp Met Arg
    1325                1330                1335

Met Thr Leu Glu Glu Gln Glu Gln Thr Gln Val Glu Gln Asp Gln
    1340                1345                1350

Val Leu Glu Ala Lys Leu Glu Glu Val Glu Arg Leu Ala Thr Glu
    1355                1360                1365

Leu Glu Lys Trp Lys Glu Lys Cys Asn Asp Leu Glu Thr Lys Asn
    1370                1375                1380

Asn Gln Arg Ser Asn Lys Glu His Glu Asn Asn Thr Asp Val Leu
    1385                1390                1395

Gly Lys Leu Thr Asn Leu Gln Asp Glu Leu Gln Glu Ser Glu Gln
    1400                1405                1410

Lys Tyr Asn Ala Asp Arg Lys Lys Trp Leu Glu Glu Lys Met Met
    1415                1420                1425

Leu Ile Thr Gln Ala Lys Glu Ala Glu Asn Ile Arg Asn Lys Glu
    1430                1435                1440

Met Lys Lys Tyr Ala Glu Asp Arg Glu Arg Phe Phe Lys Gln Gln
    1445                1450                1455
```

```
Asn Glu Met Glu Ile Leu Thr Ala Gln Leu Thr Glu Lys Asp Ser
    1460                1465                1470

Asp Leu Gln Lys Trp Arg Glu Arg Asp Gln Leu Val Ala Ala
    1475                1480                1485

Leu Glu Ile Gln Leu Lys Ala Leu Ile Ser Ser Asn Val Gln Lys
    1490                1495                1500

Asp Asn Glu Ile Glu Gln Leu Lys Arg Ile Ile Ser Glu Thr Ser
    1505                1510                1515

Lys Ile Glu Thr Gln Ile Met Asp Ile Lys Pro Lys Arg Ile Ser
    1520                1525                1530

Ser Ala Asp Pro Asp Lys Leu Gln Thr Glu Pro Leu Ser Thr Ser
    1535                1540                1545

Phe Glu Ile Ser Arg Asn Lys Ile Glu Asp Gly Ser Val Val Leu
    1550                1555                1560

Asp Ser Cys Glu Val Ser Thr Glu Asn Asp Gln Ser Thr Arg Phe
    1565                1570                1575

Pro Lys Pro Glu Leu Glu Ile Gln Phe Thr Pro Leu Gln Pro Asn
    1580                1585                1590

Lys Met Ala Val Lys His Pro Gly Cys Thr Thr Pro Val Thr Val
    1595                1600                1605

Lys Ile Pro Lys Ala Arg Lys Arg Lys Ser Asn Glu Met Glu Glu
    1610                1615                1620

Asp Leu Val Lys Cys Glu Asn Lys Lys Asn Ala Thr Pro Arg Thr
    1625                1630                1635

Asn Leu Lys Phe Pro Ile Ser Asp Asp Arg Asn Ser Ser Val Lys
    1640                1645                1650

Lys Glu Gln Lys Val Ala Ile Arg Pro Ser Ser Lys Lys Thr Tyr
    1655                1660                1665

Ser Leu Arg Ser Gln Ala Ser Ile Ile Gly Val Asn Leu Ala Thr
    1670                1675                1680

Lys Lys Lys Glu Gly Thr Leu Gln Lys Phe Gly Asp Phe Leu Gln
    1685                1690                1695

His Ser Pro Ser Ile Leu Gln Ser Lys Ala Lys Lys Ile Ile Glu
    1700                1705                1710

Thr Met Ser Ser Ser Lys Leu Ser Asn Val Glu Ala Ser Lys Glu
    1715                1720                1725

Asn Val Ser Gln Pro Lys Arg Ala Lys Arg Lys Leu Tyr Thr Ser
    1730                1735                1740

Glu Ile Ser Ser Pro Ile Asp Ile Ser Gly Gln Val Ile Leu Met
    1745                1750                1755

Asp Gln Lys Met Lys Glu Ser Asp His Gln Ile Ile Lys Arg Arg
    1760                1765                1770

Leu Arg Thr Lys Thr Ala Lys
    1775                1780

<210> SEQ ID NO 127
<211> LENGTH: 22
<212> TYPE: DNA
<213> ORGANISM: Artificial Sequence
<220> FEATURE:
<223> OTHER INFORMATION: A primer sequence

<400> SEQUENCE: 127
gtctaccagg cattcgcttc at                                              22
```

```
<210> SEQ ID NO 128
<211> LENGTH: 24
<212> TYPE: DNA
<213> ORGANISM: Artificial Sequence
<220> FEATURE:
<223> OTHER INFORMATION: A primer sequence

<400> SEQUENCE: 128
tcagctggac cacagccgca gcgt                                              24

<210> SEQ ID NO 129
<211> LENGTH: 21
<212> TYPE: DNA
<213> ORGANISM: Artificial Sequence
<220> FEATURE:
<223> OTHER INFORMATION: A primer sequence

<400> SEQUENCE: 129
tcagaaatcc tttctcttga c                                                 21

<210> SEQ ID NO 130
<211> LENGTH: 24
<212> TYPE: DNA
<213> ORGANISM: Artificial Sequence
<220> FEATURE:
<223> OTHER INFORMATION: A primer sequence

<400> SEQUENCE: 130
ctagcctctg gaatcctttc tctt                                              24
```